(12) United States Patent
Kawamoto et al.

(10) Patent No.: US 8,101,618 B2
(45) Date of Patent: Jan. 24, 2012

(54) 1,4-SUBSTITUTED PIPERAZINE DERIVATIVES

(75) Inventors: Hiroshi Kawamoto, Tsukuba (JP);
Toshifumi Kimura, Tsukkuba (JP);
Hisashi Ohta, Tsukkuba (JP); Akio Sato, Ushiku (JP); Atsushi Satoh, Tsukkuba (JP); Gentaroh Suzuki, Tsukkuba (JP)

(73) Assignee: MSD K.K., Chiyoda-Ku (JP)

( * ) Notice: Subject to any disclaimer, the term of this patent is extended or adjusted under 35 U.S.C. 154(b) by 1144 days.

(21) Appl. No.: 11/887,671

(22) PCT Filed: Apr. 5, 2006

(86) PCT No.: PCT/JP2006/307691
§ 371 (c)(1),
(2), (4) Date: Sep. 28, 2007

(87) PCT Pub. No.: WO2006/109817
PCT Pub. Date: Oct. 19, 2006

(65) Prior Publication Data
US 2009/0062293 A1     Mar. 5, 2009

(30) Foreign Application Priority Data
Apr. 6, 2005 (JP) ................................ 2005-109517

(51) Int. Cl.
| | |
|---|---|
| *A61K 31/496* | (2006.01) |
| *C07D 401/04* | (2006.01) |
| *C07D 413/04* | (2006.01) |
| *C07D 413/14* | (2006.01) |
| *A61K 31/501* | (2006.01) |
| *A61K 31/506* | (2006.01) |
| *C07D 213/74* | (2006.01) |
| *C07D 263/58* | (2006.01) |
| *C07D 277/42* | (2006.01) |
| *C07D 403/04* | (2006.01) |

(52) U.S. Cl. ........... 514/253.09; 514/253.1; 514/252.02; 514/252.19; 514/254.03; 514/254.04; 514/254.05; 544/364; 544/238; 544/295; 544/368; 544/369

(58) Field of Classification Search ........................ None
See application file for complete search history.

(56) References Cited

U.S. PATENT DOCUMENTS

| 6,093,716 | A | * | 7/2000 | Davis et al. | .............. | 514/252.18 |
| 7,683,065 | B2 | * | 3/2010 | Wilson et al. | ............. | 514/253.01 |
| 2004/0132726 | A1 | | 7/2004 | Arora et al. | | |

FOREIGN PATENT DOCUMENTS

| EP | 1764362 | 3/2007 |
| WO | WO 91/09849 | 7/1991 |
| WO | WO 03/093236 | 11/2003 |

OTHER PUBLICATIONS

CA registry No. 260367-81-5, Mar. 29, 2000 (entry date in Registry File on STN).*
Z. Ma et al., Synthesis of Acylates of Niridazole and It's Analogs as Schistosomicides, Yaoxue Xuebaio, 1989, vol. 24., No. 6, pp. 476-480.
J. Ji et al., "Selective Amination of Polyhalopyridines Catalylzed by a Palladium-Xantphos Complex" Organic Letters, 2003, vol. 5, No. 24, pp. 4611-4614.
D. L. Romero et al., Discovery, Synthesis, and Bioactivity of Bis (heteroaryl) Piperazines. 1. A novel Class of Non-Nucleoside HIV-1 Reverse Transcriptase Inhibitors, J. of Medicinal Chemitry, 1994, vol. 37, No. 7, pp. 999-1014.
Y. Hong et al., Palladium Catalyzed Amination of 2-Chloro-1, 3-Azole Derivatives: Mild Entry to Potent H1-Antihistamininc Norastemizole Tetrahedron Letters, 1997, vol. 38, No. 32, pp. 5607-5610.
L. L. Joyce et al., Copper- and Palladium-Catalyzed Intramolecular C-S Bond Formation: A Convenient Synthesis of 2-Aminobenzothiazoles, Chemical Communications, 2004, No. 4, pp. 446-447.

* cited by examiner

*Primary Examiner* — Emily Bernhardt
(74) *Attorney, Agent, or Firm* — J. Eric Thies; Gerard M. Devlin

(57) ABSTRACT

A compound represented by the formula (I):

$$R^3-R^2-N\underset{(R^4)_m}{\overset{X_1}{\bigcirc}}N-\overset{X_1}{\underset{}{\Vert}}-X_2-R^1 \qquad (I)$$

or a pharmaceutically acceptable salt thereof, wherein:
$R^1$ represents a branched lower alkyl group having from 3 to 9 carbon atoms or the like;
$R^2$ represents a 6-membered heteroaryl group having 1 or 2 nitrogen atoms or the like;
$R^3$ represents a hydrogen atom, an alkanoylamino group or the like;
$R^4$ represents a hydrogen atom, a lower alkyl group or the like;
$X_1$ represents an oxygen atom or a sulfur atom;
$X_2$ represents an oxygen atom or a single bond; and
m indicates an integer of from 0 to 4.

This compound has a metabotropic glutamate receptor 1 inhibitory effect, and therefore is useful for the treatment of a brain disorder such as convulsion, acute pain, inflammatory pain, chronic pain, cerebral infraction or transient cerebral ischemic attack, a mental dysfunction such as schizophrenia, and a disease such as anxiety and drug addition.

6 Claims, No Drawings

1,4-SUBSTITUTED PIPERAZINE DERIVATIVES

CROSS REFERENCE TO RELATED APPLICATIONS

This application is a U.S. National Phase application under 35 U.S.C. §371 of PCT Application No. PCT/JP2006/307691, filed Apr. 5, 2006, which claims priority under 35 U.S.C. §119 from Japanese Application No. JP2005-109517, filed Apr. 6, 2005.

TECHNICAL FIELD

The present invention relates to a piperazine derivative useful in the field of medicine. The compound acts as a metabotropic glutamate receptor I inhibitor and is useful as a remedy and/or a preventive for brain disorders such as convulsion, acute pain, inflammatory pain, chronic pain, cerebral infraction or transient cerebral ischemic attack, mental dysfunctions such as schizophrenia, and diseases such as anxiety and drug addiction.

BACKGROUND ART

Glutamic acid is a neurotransmitter that mediates excitation transmission in the central nervous system. In addition to having various functions for neurotransmission, glutamic acid participates in many other important brain functions such as life and death, and differentiation and propagation of neurocytes, development of neurocytes and gliacytes, and plastic change in neurotransmission efficiency of matured or developed brains (for example, see Annual Review of Biophysics and Biomolecular Structure, Vol. 23. p. 319 (1994)).

Through pharmaceutical and molecular-biological studies, the glutamic acid receptor in the central nervous system of mammals is grouped into two, an ion channel-type glutamic acid receptor and a metabotropic glutamic acid receptor (hereinafter referred to as "mGluR"). The ion channel-type glutamic acid receptor comprises a complex of different subunit proteins, and it is an ion channel that is opened and shut through ligand bonding. On the other hand, mGluR conjugates with GTP-binding protein, and it acts through intracellular second messenger production or ion channel activity control via GTP-binding protein (for example, see Brain Research Reviews, Vol. 26, p. 230 (1998)).

In previous studies, it is reported that mGluR includes eight different subtypes of mGluR 1 to 8. These are grouped into three subgroups, depending on their amino acid sequence homology, signal transmission and pharmaceutical properties. Regarding their function for intracellular signal transmission, those of group I (mGluR 1 and 5) activate phospholipase C, and those of group II (mGluR 2 and 3) and group III (mGluR 4, 6, 7 and 8) act for adenylate cyclase activity control to thereby retard cyclic adenosine monophosphate (cAMP) accumulation through forskolin stimulation. Those of group II are selectively activated by LY354740 described in references (for example, Journal of Medicinal Chemistry, Vol. 42, p. 1027 (1999)); and those of group III are by L-AP4. Except mGluR 6 that specifically exists in the retina, the other receptors are expressed broadly in brain and nervous systems, each showing characteristic intracerabral distribution therein, and it is believed that these receptors individually play their own different physiological roles (for example, see Neurochemistry International, Vol. 24, p. 439 (1994) and European Journal of Pharmacology, Vol. 375, p. 277 (1999)).

Heretofore various reports are known relating to the role of mGluR in nervous systems. A part of the relationship between mGluR1 and various diseases is shown in the following (1) to (7).

(1) It is reported that a selective agonist for group I, 3,5-dihydroxyphenylglycine (hereinafter referred to as DHPG) causes convulsion when administered to a cerebral ventricle (for example, see Journal of Neuroscience Research, Vol. 51, p. 339 (1998)).

On the other hand, it is reported that, in a test with an mGluR1 selective antagonist, RS-1-aminoindane-1,5-dicarboxylic acid (hereinafter referred to as AIDA) shows a does-dependent anticonvulsive effect in a pentylenetetrazole-induced convulsive model generally used for evaluation of anticonvulsant potency (for example, see Neuropharmacology, Vol. 37, p. 1465 (1998)), and in addition to it, the compound shows an inhibitory effect to sound stimulation-induced convulsion in a genetic convulsive mouse and rat (for example, see European Journal of Pharmacology, Vol. 368, p. 17 (1999)). Further, it is reported that another selective antagonist, LY456236 shortens the convulsion continuance time and lowers the degree of convulsion in a tronsillar nucleus kindling rat known as a human convulsive model (for example, see Neuropharmacology, Vol. 43, p. 308 (2002)). The above suggest the anticonvulsive effect of mGluR1 antagonists.

(2) It is reported that, when DHPG is administered into the spinal cavity of a rat, it causes abnormal pain and pain supersensitivity to mechanical stimulation or causes pain supersensitivity to thermal stimulation (for example, see Neuroreport, Vol. 9, p. 1169 (1998)).

On the other hand, in investigations with antagonists, it is reported that, when AIDA is administered into a brain, it increases the pain threshold value (for example, see The Journal of Pharmacology & Experimental Therapeutics, Vol. 281, p. 721 (1997)), and that AIDA administration into the spinal cavity of continuous pain models such as a spinal cord damaged pain supersensitive model (for example, see Journal of Neurotrauma, Vol. 19, p. 23 (2002)) and an arthritic model (for example, see The Journal of Pharmacology & Experimental Therapeutics, Vol. 300, p. 149 (2002)) shows an analgesic effect. These informations suggest that the possibility that mGluR1 antagonists have an analgesic effect to not only continuous acute pain but also to inflammatory pain and chronic pain.

(3) The following reports suggest a protective effect for cerebral disorders such as cerebral infraction or transient cerebral ischemic attack. AIDA's effect of inhibiting delayed neuronal cell death in the hippocampus recognized in a transient whole brain ischemia-reperfusion model (for example, see Neuropharmacology, Vol. 38, p. 1607 (1999) and Neuroscience Letters, Vol. 293, p. 1 (2000)); cerebral cortical infraction volume reduction in a rat subdural hemorrhage model by an mGluR1 selective antagonist (3aS,6aS)-6a-naphtalen-2-ylmethyl-5-methylidene-hexahydro-cyclopenta[c]furan-1-one (hereinafter referred to as "BAY36-7620") (for example, see European Journal of Pharmacology, Vol. 428, p. 203 (2001)); and infraction whole volume reduction in a rat midbrain/cerebral artery ligated model by another selective antagonist R128494 (for example, see Neuropharmacology, Vol. 43, p. 295 (2002)).

(4) Administration of DHPG to a cerebral nucleus accumbens increases spontaneous motor activity, and its effect is similar to the reaction in administration of a dopamine receptor stimulant (for example, see European Journal of Neuroscience, Vol. 13, p. 2157 (2001)).

A description is given, saying that DHPG administration to a cerebral nucleus accumbens caused prepulse inhibition disorder recognized in experimental animal models and schizophrenics (for example, see Psychopharmacology, Vol. 141, p. 405 (1999)). These reactions caused by DHPG are all similar to the reaction recognized by a dopamine receptor stimulant such as typically apomorphine or a dopamine releasant such as amphetamine or methamphetamine. On the other hand, already-existing psychotropic drugs are considered to express their effect by inhibiting excessively excited dopamine nerves. Accordingly, the fact that DHPG showed a reaction similar to a dopamine stimulative action suggests the participation of mGluR1 and mGluR5 in nucleus accumbens in metal dysfunction, and its antagonist suggests a possibility of relieving the symptoms.

(5) In a Vogel-type conflict test with rats generally used in an evaluation system capable of detecting antianxiety effect of drugs, it is reported that a selective antagonist R128494 increased water drinking action accompanied by punishment (for example, see Neuropharmacology, Vol. 43, p. 295 (2002)). This result suggests a possibility that the mGluR1 antagonist has an antianxiety effect.

(6) The above-mentioned references (for example, European Journal of Pharmacology, Vol. 428, p. 203 (2001)) say that an mGluR1 selective antagonist, BAY36-7620 inhibits intracerebral self-stimulation promoted by an NMDA receptor antagonist MK-801. It has been clinically clarified that most NMDA receptor antagonists cause addiction, and the test system may be considered as a model that partly reflects MK-801 addiction. Accordingly, the above-mentioned reports suggest the possibility that mGluR1 veceptor selective antagonists may be a remedy for drug addiction.

(7) In a test where an extracellular potential is recorded using a rat brain slice that contains the subthalamic nucleus, DHPG local application showed increase in the action potential frequency (for example, see Brain Research, Vol. 766, p. 162 (1997)), and therefore, it is suggested that mGluR1 or mGluR5 may activate a subthalamic nucleus. It is well known that the subthalamic nucleus excitation is a characteristic of Parkinson's disease. Accordingly, there may be a possibility that an mGluR1 selective antagonist may be useful as a remedy for Parkinson's disease.

(8) Gastroesophageal reflux disease (GERD) is a most popular upper gastrointestinal tract disorder. The current drug therapy for it is for inhibition of gastric acid secretion or gastric acid neutralization in esophagus. Heretofore, it has been considered that the essential mechanism relating to reflux would be chronic stress depression of lower esophageal sphincter. However, it has become shown that almost all reflux episodes may be caused by relaxation occurring by the others than transient lower esophageal sphincter relaxations (TLESRs), or that is, swallowing (for example, see Gastroenterol Clin. North Am., Vol. 19, pp. 517-535 (1990)). Further, it has been known that gastric acid secretion in GERD patients is normal.

Lower esophageal sphincter (LES) may intermittently relax. As a result, during sphincter relaxation, one may temporarily lose a mechanical barrier and gastric juice may run into esophagus. This phenomenon is defined as "reflux".

The term TLESRs indicating transient lower esophageal sphincter relaxations is defined according to Gastroenterology, Vol. 109(2), pp. 601-610 (1995).

The term "reflux" is defined as gastric juice capable of running into esophagus from stomach. This is because in that condition, one may temporarily lose its mechanical barrier.

The term "GERD" indicating gastroesophageal reflux disease is defined according to Baillière's Clinical Gastroenterology, Vol. 14, pp. 759-774 (2000).

From the above-mentioned physiological and pathophysiological meanings, an mGluR1 antagonist is considered as useful for prevention or treatment of gastrointestinal disorders.

As compounds structurally relating to the compounds of formula (I), those of the following formula are described (for example, see WO91/09849):

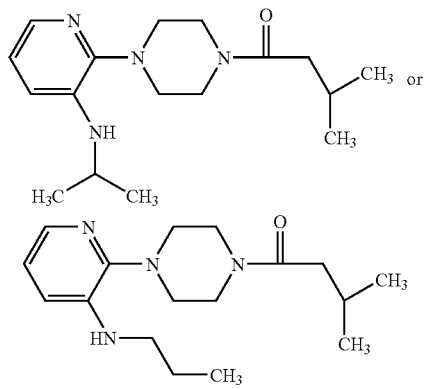

However, in these compounds, an alkylamino group bonds to the pyridine ring bonding to the nitrogen atom of the piperazine ring; but in the compounds of the present invention, an alkanoylamino group or a 5- or 6-membered heteroaryl group bonds to the pyridine ring. Accordingly, they differ in their structures.

In addition, it is merely said that the compounds of the above-mentioned formulae are useful as a remedy for AIDS, and there is known neither description nor suggestion indicating that these compounds may act as an mGluR1 antagonist and may be useful as a remedy and/or a preventive for brain disorders such as convulsion, acute pain, inflammatory pain, chronic pain, cerebral infraction or transient cerebral ischemic attack, mental dysfunctions such as schizophrenia, and diseases such as anxiety, drug addiction, Parkinson's disease or gastrointestinal disorders.

In addition, there is known no reference showing that compounds of a formula (I):

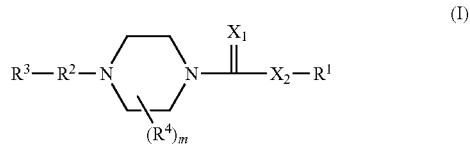

(wherein the symbols have the same meanings as above) or their pharmaceutically acceptable salts may act as an mGluR1 antagonist; and there is known no description suggesting it.

Further, there is known no reference showing that the compounds of formula (I) or their pharmaceutically acceptable salts may be useful for treatment and/or prevention of brain disorders such as convulsion, acute pain, inflammatory pain, chronic pain, cerebral infraction or transient cerebral ischemic attack, mental dysfunctions such as schizophrenia, and diseases such as anxiety, drug addiction and/or Parkinson's disease; and there is known no description suggesting it.

DISCLOSURE OF THE INVENTION

An object of the invention is to provide a novel 1,4-substituted piperazine derivative having an mGluR1 inhibitory effect.

The present inventors have assiduously studied for the purpose of developing a compound having an mGluR1 inhibitory effect and have found that the compounds of the invention are effective as those having an mGluR1 inhibitory effect; and on the basis of this finding, the inventors have completed the present invention.

Specifically, the invention relates to the following:

(1) A compound of a formula (I):

$$R^3-R^2-N\underset{(R^4)_m}{\overset{\phantom{X}}{\bigcirc}}N\overset{X_1}{=}X_2-R^1 \qquad (I)$$

or a pharmaceutically acceptable salt thereof, wherein:

$R^1$ represents a branched lower alkyl group having from 3 to 9 carbon atoms;

said branched alkyl groups may bond to each other to form a cycloalkyl group;

$R^2$ represents a 6-membered heteroaryl group having 1 or 2 nitrogen atoms, or represents a 5-membered heteroaryl group having, in the ring, from 1 to 3 hetero atoms selected from a group consisting of a nitrogen atom, a sulfur atom and an oxygen atom, in which at least one hetero atom is a nitrogen atom;

$R^3$ represents a hydrogen atom, an alkanoylamino group, a lower alkoxycarbonylamino group, a lower alkoxycarbonyl group, a carbamoyl group, a lower alkylsulfonylamino group, a nitro group, a lower alkyl group, a lower alkoxy group, an amino group, a halogen atom or a cyano group, said lower alkyl group may be substituted with a hydroxy group or a halogen atom; or represents a 6-membered heteroaryl group having 1 or 2 nitrogen atoms or a 5-membered heteroaryl group having, in the ring, from 1 to 4 hetero atoms selected from a group consisting of a nitrogen atom, a sulfur atom and an oxygen atom, which may optionally have a substituent selected from a substituent group α, or $R^2$ and $R^3$, taken together, represent a group of a formula (II):

$$(R^5)_m-\underset{Y}{\overset{N}{\bigcirc\!\!\!\bigcirc}} \qquad (II)$$

wherein:

Y represents a nitrogen atom, a sulfur atom or an oxygen atom;

$R^5$ represents a lower alkyl group, a lower alkoxy group or a halogen atom);

$R^4$ represents a hydrogen atom or a lower alkyl group; said lower alkyl group may be substituted with a halogen atom;

$X_1$ represents an oxygen atom or a sulfur atom;

$X_2$ represents an oxygen atom or a single bond;

m indicates an integer of from 0 to 4;

provided that the compound of formula (I) does not include 1-(3,3-dimethyl-1-oxobutyl)-4-(2-pyridinyl)-piperazine, 1-(3-methyl-1-oxobutyl)-4-(2-pyridinyl)-piperazine, 1-(3-methyl-1-oxobutyl)-4-(2-pyrimidinyl)-piperazine, 1-(3,3-dimethyl-1-oxobutyl)-4-(2-pyrimidinyl)-piperazine, 1-(3,3-dimethyl-1-oxobutyl)-4-[4-(trifluoromethyl)-2-pyridinyl]-piperazine, 1,1-dimethylethyl 4-[5-(hydroxymethyl)-1,2,4-oxadiazol-3-yl]-1-piperazinecarboxylate, 1,1-dimethylethyl 4-[5-(3-chloro-2-thienyl)-1,2,4-oxadiazol-3-yl]-1-piperazinecarboxylate, 1,1-dimethylethyl 4-[5-(3-bromo-2-furanyl)-1,2,4-oxadiazol-3-yl]-1-piperazinecarboxylate, and 1,1-dimethylethyl 4-[5-(chloromethyl)-1,2,4-oxadiazol-3-yl]-1-piperazinecarboxylate substituent group α:

a lower alkoxycarbonyl group, a lower alkylsulfanyl group, a lower alkyl group optionally substituted with a halogen atom, a lower alkoxy group or a hydroxy group, a hydroxy group, a cycloalkyl group, an amino group, an oxo group, a mono-lower alkylamino group and a di-lower alkylamino group; said di-lower alkyl groups may bond to each other to form a 5- to 7-membered ring;

(2) A compound of a formula (I):

$$R^3-R^2-N\underset{(R^4)_m}{\overset{\phantom{X}}{\bigcirc}}N\overset{X_1}{=}X_2-R^1 \qquad (I)$$

or a pharmaceutically acceptable salt thereof, wherein:

$R^1$ represents a branched lower alkyl group having from 3 to 9 carbon atoms; said branched alkyl groups may bond to each other to form a cycloalkyl group;

$R^2$ represents a 6-membered heteroaryl group having 1 or 2 nitrogen atoms, or represents a 5-membered heteroaryl group having, in the ring, from 1 to 3 hetero atoms selected from a group consisting of a nitrogen atom, a sulfur atom and an oxygen atom, in which at least one hetero atom is a nitrogen atom;

$R^3$ represents a hydrogen atom, an alkanoylamino group, a lower alkoxycarbonylamino group, a lower alkoxycarbonyl group, a carbamoyl group, a lower alkylsulfonylamino group, a nitro group, a lower alkyl group, a lower alkoxy group, an amino group, a halogen atom or a cyano group;

said lower alkyl group may be substituted with a hydroxy group or a halogen atom; or represents a 6-membered heteroaryl group having 1 or 2 nitrogen atoms or a 5-membered heteroaryl group having, in the ring, from 1 to 4 hetero atoms selected from a group consisting of a nitrogen atom, a sulfur atom and an oxygen atom, which may optionally have a substituent selected from a substituent group α, or $R^2$ and $R^3$, taken together, represent a group of a formula (II):

$$(R^5)_m-\underset{Y}{\overset{N}{\bigcirc\!\!\!\bigcirc}} \qquad (II)$$

wherein Y represents a nitrogen atom, a sulfur atom or an oxygen atom; $R^5$ represents a lower alkyl group, a lower alkoxy group or a halogen atom;

R⁴ represents a hydrogen atom or a lower alkyl group (the lower alkyl group may be substituted with a halogen atom);

X₁ represents an oxygen atom or a sulfur atom;

X₂ represents an oxygen atom or a single bond;

m indicates an integer of from 0 to 4;

provided that the compound of formula (I) does not include 1-(3,3-dimethyl-1-oxobutyl)-4-(2-pyridinyl)-piperazine, 1-(3-methyl-1-oxobutyl)-4-(2-pyridinyl)-piperazine, 1-(3-methyl-1-oxobutyl)-4-(2-pyrimidinyl)-piperazine, 1-(3,3-dimethyl-1-oxobutyl)-4-(2-pyrimidinyl)-piperazine, 1-(3,3-dimethyl-1-oxobutyl)-4-[4-(trifluoromethyl)-2-pyridinyl]-piperazine, and those of formula (I) where X₂ is an oxygen atom and R¹ is a tert-butyl group;

substituent group α:

a lower alkoxycarbonyl group, a lower alkylsulfanyl group, a lower alkyl group optionally substituted with a halogen atom, a lower alkoxy group or a hydroxy group, a hydroxy group, a cycloalkyl group, an amino group, an oxo group, a mono-lower alkylamino group and a di-lower alkylamino group; said di-lower alkyl groups may bond to each other to form a 5- to 7-membered ring;

(3) The compound according to above (2) or a pharmaceutically acceptable salt thereof, wherein X₁ is an oxygen atom;

(4) The compound according to above. (2) or a pharmaceutically acceptable salt thereof, wherein:

X₁ is an oxygen atom;

R² is a 6-membered heteroaryl group having 1 or 2 nitrogen atoms; and

R³ is a hydrogen atom, an alkanoylamino group, a lower alkoxycarbonylamino group, a lower alkoxycarbonyl group, a carbamoyl group, a lower alkylsulfonylamino group, a nitro group, a lower alkyl group, a lower alkoxy group, an amino group, a halogen atom or a cyano group;

said lower alkyl group may be substituted with a hydroxy group or a halogen atom; or represents a 5-membered heteroaryl group having, in the ring, from 1 to 4 hetero atoms selected from a group consisting of a nitrogen atom, a sulfur atom and an oxygen atom, which may have a substituent selected from the substituent group a;

(5) The compound according to above (2) or a pharmaceutically acceptable salt thereof, wherein:

X₁ is an oxygen atom;

R² is a 6-membered heteroaryl group having 1 or 2 nitrogen atoms; and

R³ is a hydrogen atom, an alkanoylamino group, a lower alkoxycarbonylamino group, a lower alkoxycarbonyl group, a carbamoyl group, a lower alkylsulfonylamino group, a nitro group, a lower alkyl group, a lower alkoxy group, an amino group, a halogen atom or a cyano group;

said lower alkyl group may be substituted with a hydroxy group or a halogen atom;

(6) The compound according to above (2) or a pharmaceutically acceptable salt thereof, wherein:

X₁ is an oxygen atom;

R² is a 6-membered heteroaryl group having 1 or 2 nitrogen atoms; and

R³ is a 5-membered heteroaryl group having, in the ring, from 1 to 4 hetero atoms selected from a group consisting of a nitrogen atom, a sulfur atom and an oxygen atom, which may have a substituent selected from the substituent group a;

(7) The compound according to above (2) or a pharmaceutically acceptable salt thereof, wherein:

X₁ is an oxygen atom;

R² is a 6-membered heteroaryl group having 1 or 2 nitrogen atoms; and

R³ is an oxadiazolyl group, a thiadiazolyl group, a triazolyl group, a tetrazolyl group or a thiazolyl group, which may have a substituent selected from the substituent group a;

(8) The compound according to above (2) or a pharmaceutically acceptable salt thereof, wherein:

X₁ is an oxygen atom;

R² and R³, taken together, represent a group of a formula (II):

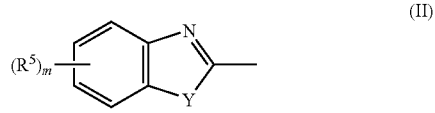

wherein:

Y represents a nitrogen atom, a sulfur atom or an oxygen atom; and

R⁵ represents a lower alkyl group, a lower alkoxy group or a halogen atom;

(9) The compound according to above (2) or a pharmaceutically acceptable salt thereof, wherein:

X₁ is an oxygen atom; and

R³ is a 5-membered heteroaryl group having, in the ring, from 1 to 4 hetero atoms selected from a group consisting of a nitrogen atom, a sulfur atom and an oxygen atom, in which at least one hetero atom is a nitrogen atom;

(10) The compound according to above (2) or a pharmaceutically acceptable salt thereof, wherein X₁ is an oxygen atom, and R³ is an oxadiazolyl group, a triazolyl group or a pyridinyl group;

(11) The compound or its pharmaceutically acceptable salt of above (2), wherein the compound of formula (I) is:

2,2-dimethylpropyl 4-(4-methylpyridin-2-yl)-1-piperazinecarboxylate, 2,2-dimethylpropyl 4-(4-cyanopyridin-2-yl)-1-piperazinecarboxylate, 2,2-dimethylpropyl 4-(benzoxazol-2-yl)-1-piperazinecarboxylate, 2,2-dimethylpropyl 4-(6-chloropyrimidin-4-yl)-1-piperazinecarboxylate, 2,2-dimethylpropyl 4-[4-(methoxycarbonyl)pyridin-2-yl]-1-piperazinecarboxylate, 2,2-dimethylpropyl 4-(4-methoxypyridin-2-yl)-1-piperazinecarboxylate, 2,2-dimethylpropyl 4-(6-chloropyridazin-3-yl)-1-piperazinecarboxylate, 2,2-dimethylpropyl 4-(4-nitropyridin-2-yl)-1-piperazinecarboxylate, 2,2-dimethylpropyl 4-(5-chloropyridin-2-yl)-1-piperazinecarboxylate, 2,2-dimethylpropyl 4-(6-methylpyridin-2-yl)-1-piperazinecarboxylate, 2,2-dimethylpropyl 4-(6-methoxypyridin-2-yl)-1-piperazinecarboxylate, 2,2-dimethylpropyl 4-[4-(trifluoromethyl)pyridin-2-yl]-1-piperazinecarboxylate, 2,2-dimethylpropyl 4-(5-methylpyridin-2-yl)-1-piperazinecarboxylate, 2,2-dimethylpropyl 4-(4,6-dimethylpyrimidin-2-yl)-1-piperazinecarboxylate, 2,2-dimethylpropyl 4-(thiazol-2-yl)-1-piperazinecarboxylate, 2,2-dimethylpropyl 4-(6-chloropyridin-2-yl)-1-piperazinecarboxylate, 2,2-dimethylpropyl 4-(3-methylpyridin-2-yl)-1-piperazinecarboxylate,
2,2-dimethylpropyl 4-(pyridin-2-yl)-1-piperazinecarboxylate,
2,2-dimethylpropyl 4-(pyrimidin-2-yl)-1-piperazinecarboxylate,
2,2-dimethylpropyl 4-(4-aminopyridin-2-yl)-1-piperazinecarboxy late,
2,2-dimethylpropyl 4-[4-(acetylamino)pyridin-2-yl]-1-piperazinecarboxylate,
2,2-dimethylpropyl 4-{4-[(methoxycarbonyl)amino]pyridin-2-yl}-1-piperazinecarboxylate,
2,2-dimethylpropyl 4-[4-(propionylamino)pyridin-2-yl]-1-piperazinecarboxylate,
2,2-dimethylpropyl 4-[4-(hydroxymethyl)pyridin-2-yl]-1-piperazinecarboxylate
2,2-dimethylpropyl 4-(pyrimidin-4-yl)-1-piperazinecarboxylate,
2,2-dimethylpropyl 4-(4-{5-[(1S)-1-hydroxyethyl]-1,2,4-oxadiazol-3-yl}pyridin-2-yl)-1-piperazinecarboxylate,
2,2-dimethylpropyl 4-(4-{5-[(1R)-1-hydroxyethyl]-1,2,4-oxadiazol-3-yl}pyridin-2-yl)-1-piperazinecarboxylate,
2,2-dimethylpropyl 4-[4-(5-methyl-1,2,4-oxadiazol-3-yl)pyridin-2-yl]-1-piperazinecarboxylate,
2,2-dimethylpropyl 4-[4-(5-methoxy-1,2,4-oxadiazol-3-yl)pyridin-2-yl]-1-piperazinecarboxylate,
2,2-dimethylpropyl 4-[4-(5-cyclopropyl-1,2,4-oxadiazol-3-yl)pyridin-2-yl]-1-piperazinecarboxylate,
2,2-dimethylpropyl 4-{4-[5-(methoxycarbonyl)-1,2,4-oxadiazol-3-yl]pyridin-2-yl}-1-piperazinecarboxylate,
2,2-dimethylpropyl 4-{4-[5-(trichloromethyl)-1,2,4-oxadiazol-3-yl]pyridin-2-yl}-1-piperazinecarboxylate,
2,2-dimethylpropyl 4-{4-[5-(trifluoromethyl)-1,2,4-oxadiazol-3-yl]pyridin-2-yl}-1-piperazinecarboxylate,
2,2-dimethylpropyl 4-[4-(5-methoxy-1,2,4-oxadiazol-3-yl)pyridin-2-yl]-1-piperazinecarboxylate,
2,2-dimethylpropyl 4-[4-(1,2,4-oxadiazol-3-yl)pyridin-2-yl]-1-piperazinecarboxylate,
2,2-dimethylpropyl 4-[4-(5-carbamoyl-1,2,4-oxadiazol-3-yl)pyridin-2-yl]-1-piperazinecarboxy late,
2,2-dimethylpropyl 4-{4-[5-(dimethylamino)-1,2,4-oxadiazol-3-yl]pyridin-2-yl}-1-piperazinecarboxy late,
2,2-dimethylpropyl 4-[4-(5-amino-1,2,4-oxadiazol-3-yl)pyridin-2-yl]-1-piperazinecarboxylate,
2,2-dimethylpropyl 4-{4-[5-(methylamino)-1,2,4-oxadiazol-3-yl]pyridin-2-yl}-1-piperazinecarboxylate,
2,2-dimethylpropyl 4-[4-(5-piperidinyl-1,2,4-oxadiazol-3-yl)pyridin-2-yl]-1-piperazinecarboxylate,
2,2-dimethylpropyl 4-[4-(3-methyl-1,2,4-oxadiazol-5-yl)pyridin-2-yl]-1-piperazinecarboxylate,
2,2-dimethylpropyl 4-{4-[5-(methylamino)-1,2,4-thiadiazol-3-yl]pyridin-2-yl}-1-piperazinecarboxylate,
2,2-dimethylpropyl 4-[4-(5-methyl-1,2,4-triazol-3-yl)pyridin-2-yl]-1-piperazinecarboxylate,
2,2-dimethylpropyl 4-[4-(tetrazol-5-yl)pyridin-2-yl]-1-piperazinecarboxylate,
2,2-dimethylpropyl 4-{4-[5-(methylthio)-1,2,4-oxadiazol-3-yl]pyridin-2-yl}-1-piperazinecarboxylate,
2,2-dimethylpropyl 4-(2-methylthiazol-4-yl)-1-piperazinecarboxylate, tert-butyl 4-(5-tert-butyl-1,2,4-oxadiazol-3-yl)-1-piperazinecarboxylate,
tert-butyl 4-(5-phenyl-1,2,4-oxadiazol-3-yl)-1-piperazinecarboxylate,
tert-butyl 4-[5-(2,2-dimethylpropyl)-1,2,4-oxadiazol-3-yl]-1-piperazinecarboxylate,
tert-butyl 4-[5-(2-chlorophenyl)-1,2,4-oxadiazol-3-yl]-1-piperazinecarboxylate,
tert-butyl 4-(5-tert-butyl-1,2,4-triazol-3-yl)-1-piperazinecarboxylate,
tert-butyl 4-[5-(pyridin-3-yl)-1,2,4-oxadiazol-3-yl]-1-piperazinecarboxylate,
1-(4,4-dimethylpentanoyl)-4-(4-cyanopyridin-2-yl)piperazine,
1-(4,4-dimethylpentanoyl)-4-(4-cyanopyrimidin-2-yl)piperazine,
1-(4,4-dimethylpentanoyl)-4-(4-methylpyridin-2-yl)piperazine,
1-(4,4-dimethylpentanoyl)-4-{4-[5-(methoxymethyl)-1,2,4-oxadiazol-3-yl]pyridin-2-yl}piperazine,
1-(4,4-dimethylpentanoyl)-4-[4-(5-methyl-1,2,4-oxadiazol-3-yl)pyridin-2-yl]piperazine,
1-(4,4-dimethylpentanoyl)-4-(4-{5-[(1S)-hydroxyethyl]-1,2,4-oxadiazol-3-yl}pyridin-2-yl)piperazine,
1-(4,4-dimethylpentanoyl)-4-(4-{5-[(1R)-hydroxyethyl]-1,2,4-oxadiazol-3-yl}pyridin-2-yl)piperazine,
1-(4,4-dimethylpentanoyl)-4-{4-[5-(hydroxymethyl)-1,2,4-oxadiazol-3-yl]pyridin-2-yl}piperazine,
1-(4,4-dimethylpentanoyl)-4-[4-(5-cyclopropyl-1,2,4-oxadiazol-3-yl)pyridin-2-yl]piperazine,
1-(4,4-dimethylpentanoyl)-4-{4-[5-(1-hydroxy-1-methylethyl)-1,2,4-oxadiazol-3-yl]pyridin-2-yl}piperazine,
1-(4,4-dimethylpentanoyl)-4-{4-[5-(difluoromethyl)-1,2,4-oxadiazol-3-yl]pyridin-2-yl}piperazine,
1-(4,4-dimethylpentanoyl)-4-[4-(5-cyclopropyl-1,2,4-oxadiazol-3-yl)pyrimidin-2-yl]piperazine,
1-(4,4-dimethylpentanoyl)-4-{4-[5-(methoxymethyl)-1,2,4-oxadiazol-3-yl]pyrimidin-2-yl}piperazine,
1-(4,4-dimethylpentanoyl)-4-[4-(5-methyl-1,2,4-oxadiazol-3-yl)pyrimidin-2-yl]piperazine,
1-(4,4-dimethylpentanoyl)-4-{4-[5-(1-hydroxycyclopropyl)-1,2,4-oxadiazol-3-yl]pyrimidin-2-yl}piperazine,
1-(4,4-dimethylpentanoyl)-4-{4-[5-(dimethylamino)-1,2,4-oxadiazol-3-yl]pyridin-2-yl}piperazine,
1-(4,4-dimethylpentanoyl)-4-{4-[5-(methylamino)-1,2,4-oxadiazol-3-yl]pyridin-2-yl}piperazine,
1-(4,4-dimethylpentanoyl)-4-[4-(1,2,4-oxadiazol-3-yl)pyridin-2-yl]piperazine, or
1-(4,4-dimethylpentanoyl)-4-[4-(5-amino-1,2,4-oxadiazol-3-yl)pyridin-2-yl]piperazine;

(12) An mGluR1 antagonist comprising, as the active ingredient thereof, a compound or its pharmaceutically acceptable salt of a formula (I):

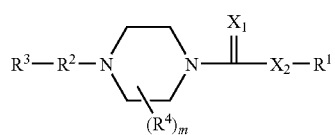

wherein:
$R^1$ represents a branched lower alkyl group having from 3 to 9 carbon atoms;
said branched alkyl groups may bond to each other to form a cycloalkyl group;
$R^2$ represents a 6-membered heteroaryl group having 1 or 2 nitrogen atoms, or represents a 5-membered heteroaryl group having, in the ring, from 1 to 3 hetero atoms selected from a group consisting of a nitrogen atom, a sulfur atom and an oxygen atom, in which at least one hetero atom is a nitrogen atom;
$R^3$ represents a hydrogen atom, an alkanoylamino group, a lower alkoxycarbonylamino group, a lower alkoxycarbonyl group, a carbamoyl group, a lower alkylsulfonylamino group, a nitro group, a lower alkyl group, a lower alkoxy group, an amino group, a halogen atom or a cyano group, said lower alkyl group may be substituted with a hydroxy group or a halogen atom; or represents a 6-membered heteroaryl group having 1 or 2 nitrogen atoms or a 5-membered heteroaryl group having, in the ring, from 1 to 4 hetero atoms selected from a group consisting of a nitrogen atom, a sulfur atom and an oxygen atom, which may optionally have a substituent selected from a substituent group α, or $R^2$ and $R^3$, taken together, represent a group of a formula (II):

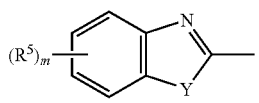

wherein:

Y represents a nitrogen atom, a sulfur atom or an oxygen atom;

$R^5$ represents a lower alkyl group, a lower alkoxy group or a halogen atom);

$R^4$ represents a hydrogen atom or a lower alkyl group;

said lower alkyl group may be substituted with a halogen atom;

$X_1$ represents an oxygen atom or a sulfur atom;

$X_2$ represents an oxygen atom or a single bond;

m indicates an integer of from 0 to 4;

substituent group α:

a lower alkoxycarbonyl group, a lower alkylsulfanyl group, a lower alkyl group optionally substituted with a halogen atom, a lower alkoxy group or a hydroxy group, a hydroxy group, a cycloalkyl group, an amino group, an oxo group, a mono-lower alkylamino group and a di-lower alkylamino group; said di-lower alkyl groups may bond to each other to form a 5- to 7-membered ring;

(13) The mGluR1 antagonist comprising, as the active ingredient thereof, a compound or its pharmaceutically acceptable salt of above (12), wherein $X_1$ is an oxygen atom;

(14) The mGluR1 antagonist comprising, as the active ingredient thereof, a compound or its pharmaceutically acceptable salt of above (13), wherein:

$R^2$ is a 6-membered heteroaryl group having 1 or 2 nitrogen atoms;

$R^3$ is a hydrogen atom, an alkanoylamino group, a lower alkoxycarbonylamino group, a lower alkoxycarbonyl group, a carbamoyl group, a lower alkylsulfonylamino group, a nitro group, a lower alkyl group, a lower alkoxy group, an amino group, a halogen atom or a cyano group;

said lower alkyl group may be substituted with a hydroxy group or a halogen atom; or represents a 5-membered heteroaryl group having, in the ring, from 1 to 4 hetero atoms selected from a group consisting of a nitrogen atom, a sulfur atom and an oxygen atom, which may have a substituent selected from the above-mentioned substituent group α;

(15) The mGluR1 antagonist comprising, as the active ingredient thereof, a compound or its pharmaceutically acceptable salt of above (13), wherein:

$R^2$ is a 6-membered heteroaryl group having 1 or 2 nitrogen atoms;

$R^3$ is a hydrogen atom, an alkanoylamino group, a lower alkoxycarbonylamino group, a lower alkoxycarbonyl group, a carbamoyl group, a lower alkylsulfonylamino group, a nitro group, a lower alkyl group, a lower alkoxy group, an amino group, a halogen atom or a cyano group;

said lower alkyl group may be substituted with a hydroxy group or a halogen atom;

(16) The mGluR1 antagonist comprising, as the active ingredient thereof, a compound or its pharmaceutically acceptable salt of above (13), wherein:

$R^2$ is a 6-membered heteroaryl group having 1 or 2 nitrogen atoms;

$R^3$ is a 5-membered heteroaryl group having, in the ring, from 1 to 4 hetero atoms selected from a group consisting of a nitrogen atom, a sulfur atom and an oxygen atom, which may have a substituent selected from the substituent group α;

(17) The mGluR1 antagonist comprising, as the active ingredient thereof, a compound or its pharmaceutically acceptable salt of above (13), wherein:

$R^2$ is a 6-membered heteroaryl group having 1 or 2 nitrogen atoms;

$R^3$ is an oxadiazolyl group, a thiadiazolyl group, a triazolyl group, a tetrazolyl group or a thiazolyl group, which may have a substituent selected from the substituent group α.

(18) The mGluR1 antagonist comprising, as the active ingredient thereof, a compound or its pharmaceutically acceptable salt of above (13), wherein:

$X_1$ is an oxygen atom, and $R^2$ and $R^3$, taken together, represent a group of a formula (II):

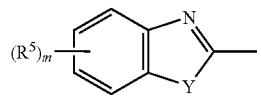

wherein:

Y represents a nitrogen atom, a sulfur atom or an oxygen atom;

$R^5$ represents a lower alkyl group, a lower alkoxy group or a halogen atom;

(19) The mGluR1 antagonist comprising, as the active ingredient thereof, a compound or its pharmaceutically acceptable salt of above (13), wherein the compound of formula (I-1) is:

2,2-dimethylpropyl 4-(4-methylpyridin-2-yl)-1-piperazinecarboxylate, 2,2-dimethylpropyl 4-(4-cyanopyridin-2-yl)-1-piperazinecarboxylate, 2,2-dimethylpropyl 4-(benzoxazol-2-yl)-1-piperazinecarboxylate, 2,2-dimethylpropyl 4-(6-chloropyrimidin-4-yl)-1-piperazinecarboxylate, 2,2-dimethylpropyl 4-[4-(methoxycarbonyl)pyridin-2-yl]-1-piperazinecarboxylate, 2,2-dimethylpropyl 4-(4-methoxypyridin-2-yl)-1-piperazinecarboxylate, 2,2-dimethylpropyl 4-(6-chloropyridazin-3-yl)-1-piperazinecarboxylate, 2,2-dimethylpropyl 4-(4-nitropyridin-2-yl)-1-piperazinecarboxylate, 2,2-dimethylpropyl 4-(5-chloropyridin-2-yl)-1-piperazinecarboxylate, 2,2-dimethylpropyl 4-(6-methylpyridin-2-yl)-1-piperazinecarboxylate, 2,2-dimethylpropyl 4-(6-methoxypyridin-2-yl)-1-piperazinecarboxylate, 2,2-dimethylpropyl 4-[4-(trifluoromethyl)pyridin-2-yl]-1-piperazinecarboxylate,
2,2-dimethylpropyl 4-(5-methylpyridin-2-yl)-1-piperazinecarboxylate,
2,2-dimethylpropyl 4-(4,6-dimethylpyrimidin-2-yl)-1-piperazinecarboxylate,
2,2-dimethylpropyl 4-(thiazol-2-yl)-1-piperazinecarboxylate,
2,2-dimethylpropyl 4-(6-chloropyridin-2-yl)-1-piperazinecarboxylate,
2,2-dimethylpropyl 4-(3-methylpyridin-2-yl)-1-piperazinecarboxylate,
2,2-dimethylpropyl 4-(pyridin-2-yl)-1-piperazinecarboxylate,
2,2-dimethylpropyl 4-(pyrimidin-2-yl)-1-piperazinecarboxylate,
2,2-dimethylpropyl 4-(4-aminopyridin-2-yl)-1-piperazinecarboxylate,
2,2-dimethylpropyl 4-[4-(acetylamino)pyridin-2-yl]-1-piperazinecarboxylate,
2,2-dimethylpropyl 4-{4-[(methoxycarbonyl)amino]pyridin-2-yl}-1-piperazinecarboxylate,
2,2-dimethylpropyl 4-[4-(propionylamino)pyridin-2-yl]-1-piperazinecarboxylate,
2,2-dimethylpropyl 4-[4-(hydroxymethyl)pyridin-2-yl]-1-piperazinecarboxylate
2,2-dimethylpropyl 4-(pyrimidin-4-yl)-1-piperazinecarboxylate,
2,2-dimethylpropyl 4-(4-{5-[(1S)-1-hydroxyethyl]-1,2,4-oxadiazol-3-yl}pyridin-2-yl)-1-piperazinecarboxylate,
2,2-dimethylpropyl 4-(4-{5-[(1R)-1-hydroxyethyl]-1,2,4-oxadiazol-3-yl}pyridin-2-yl)-1-piperazinecarboxylate,
2,2-dimethylpropyl 4-[4-(5-methyl-1,2,4-oxadiazol-3-yl)pyridin-2-yl]-1-piperazinecarboxylate,
2,2-dimethylpropyl 4-[4-(5-methoxy-1,2,4-oxadiazol-3-yl)pyridin-2-yl]-1-piperazinecarboxylate,
2,2-dimethylpropyl 4-[4-(5-cyclopropyl-1,2,4-oxadiazol-3-yl)pyridin-2-yl]-1-piperazinecarboxylate,
2,2-dimethylpropyl 4-{4-[5-(methoxycarbonyl)-1,2,4-oxadiazol-3-yl]pyridin-2-yl}-1-piperazinecarboxylate,
2,2-dimethylpropyl 4-{4-[5-(trichloromethyl)-1,2,4-oxadiazol-3-yl]pyridin-2-yl}-1-piperazinecarboxylate,
2,2-dimethylpropyl 4-{4-[5-(trifluoromethyl)-1,2,4-oxadiazol-3-yl]pyridin-2-yl}-1-piperazinecarboxylate,
2,2-dimethylpropyl 4-[4-(5-methoxy-1,2,4-oxadiazol-3-yl)pyridin-2-yl]-1-piperazinecarboxylate,
2,2-dimethylpropyl 4-[4-(1,2,4-oxadiazol-3-yl)pyridin-2-yl]-1-piperazinecarboxylate,
2,2-dimethylpropyl 4-[4-(5-carbamoyl-1,2,4-oxadiazol-3-yl)pyridin-2-yl]-1-piperazinecarboxylate,
2,2-dimethylpropyl 4-{4-[5-(dimethylamino)-1,2,4-oxadiazol-3-yl]pyridin-2-yl}-1-piperazinecarboxylate,
2,2-dimethylpropyl 4-[4-(5-amino-1,2,4-oxadiazol-3-yl)pyridin-2-yl]-1-piperazinecarboxy late,
2,2-dimethylpropyl 4-{4-[5-(methylamino)-1,2,4-oxadiazol-3-yl]pyridin-2-yl}-1-piperazinecarboxylate,
2,2-dimethylpropyl 4-[4-(5-piperidinyl-1,2,4-oxadiazol-3-yl)pyridin-2-yl]-1-piperazinecarboxylate,
2,2-dimethylpropyl 4-[4-(3-methyl-1,2,4-oxadiazol-5-yl)pyridin-2-yl]-1-piperazinecarboxylate,
2,2-dimethylpropyl 4-{4-[5-(methylamino)-1,2,4-thiadiazol-3-yl]pyridin-2-yl}-1-piperazinecarboxylate,
2,2-dimethylpropyl 4-[4-(5-methyl-1,2,4-triazol-3-yl)pyridin-2-yl]-1-piperazinecarboxylate,
2,2-dimethylpropyl 4-[4-(tetrazol-5-yl)pyridin-2-yl]-1-piperazinecarboxylate,
2,2-dimethylpropyl 4-{4-[5-(methylthio)-1,2,4-oxadiazol-3-yl]pyridin-2-yl}-1-piperazinecarboxylate,
2,2-dimethylpropyl 4-(2-methylthiazol-4-yl)-1-piperazinecarboxylate,
tert-butyl 4-(5-tert-butyl-1,2,4-oxadiazol-3-yl)-1-piperazinecarboxylate,
tert-butyl 4-(5-phenyl-1,2,4-oxadiazol-3-yl)-1-piperazinecarboxylate,
tert-butyl 4-[5-(2,2-dimethylpropyl)-1,2,4-oxadiazol-3-yl]-1-piperazinecarboxylate,
tert-butyl 4-[5-(2-chlorophenyl)-1,2,4-oxadiazol-3-yl]-1-piperazinecarboxylate,
tert-butyl 4-(5-tert-butyl-1,2,4-triazol-3-yl)-1-piperazinecarboxylate,
tert-butyl 4-[5-(pyridin-3-yl)-1,2,4-oxadiazol-3-yl]-1-piperazinecarboxylate,
1-(4,4-dimethylpentanoyl)-4-(4-cyanopyridin-2-yl)piperazine,
1-(4,4-dimethylpentanoyl)-4-(4-cyanopyrimidin-2-yl)piperazine,
1-(4,4-dimethylpentanoyl)-4-(4-methylpyridin-2-yl)piperazine,
1-(4,4-dimethylpentanoyl)-4-{4-[5-(methoxymethyl)-1,2,4-oxadiazol-3-yl]pyridin-2-yl}piperazine,
1-(4,4-dimethylpentanoyl)-4-[4-(5-methyl-1,2,4-oxadiazol-3-yl)pyridin-2-yl]piperazine,
1-(4,4-dimethylpentanoyl)-4-(4-{5-[(1S)-hydroxyethyl]-1,2,4-oxadiazol-3-yl}pyridin-2-yl)piperazine,
1-(4,4-dimethylpentanoyl)-4-(4-{5-[(1R)-hydroxyethyl]-1,2,4-oxadiazol-3-yl}pyridin-2-yl)piperazine,
1-(4,4-dimethylpentanoyl)-4-{4-[5-(hydroxymethyl)-1,2,4-oxadiazol-3-yl]pyridin-2-yl}piperazine,
1-(4,4-dimethylpentanoyl)-4-[4-(5-cyclopropyl-1,2,4-oxadiazol-3-yl)pyridin-2-yl]piperazine,
1-(4,4-dimethylpentanoyl)-4-{4-[5-(1-hydroxy-1-methylethyl)-1,2,4-oxadiazol-3-yl]pyridin-2-yl}piperazine,
1-(4,4-dimethylpentanoyl)-4-{4-[5-(difluoromethyl)-1,2,4-oxadiazol-3-yl]pyridin-2-yl}piperazine,
1-(4,4-dimethylpentanoyl)-4-[4-(5-cyclopropyl-1,2,4-oxadiazol-3-yl)pyrimidin-2-yl]piperazine,
1-(4,4-dimethylpentanoyl)-4-{4-[5-(methoxymethyl)-1,2,4-oxadiazol-3-yl]pyrimidin-2-yl}piperazine,
1-(4,4-dimethylpentanoyl)-4-[4-(5-methyl-1,2,4-oxadiazol-3-yl)pyrimidin-2-yl]piperazine,
1-(4,4-dimethylpentanoyl)-4-{4-[5-(1-hydroxycyclopropyl)-1,2,4-oxadiazol-3-yl]pyrimidin-2-yl}piperazine,
1-(4,4-dimethylpentanoyl)-4-{4-[5-(dimethylamino)-1,2,4-oxadiazol-3-yl]pyridin-2-yl}piperazine,
1-(4,4-dimethylpentanoyl)-4-{4-[5-(methylamino)-1,2,4-oxadiazol-3-yl]pyridin-2-yl}piperazine,
1-(4,4-dimethylpentanoyl)-4-[4-(1,2,4-oxadiazol-3-yl)pyridin-2-yl]piperazine, or
1-(4,4-dimethylpentanoyl)-4-[4-(5-amino-1,2,4-oxadiazol-3-yl)pyridin-2-yl]piperazine;

(20) A remedy and/or a preventive for brain disorders such as convulsion, acute pain, inflammatory pain, chronic pain, cerebral infraction or transient cerebral ischemic attack, mental dysfunctions such as schizophrenia, and diseases such as anxiety, drug addiction and/or Parkinson's disease, and gastrointestinal disorders, which comprises, as the active ingredient thereof, a compound or its pharmaceutically acceptable salt of any one of above (1) to (11).

BEST MODE FOR CARRYING OUT THE INVENTION

The meanings of the terms used in this description are described below, and the compounds of the invention are described in more detail hereinunder.

"Halogen atom" includes, for example, a fluorine atom, a chlorine atom, a bromine atom, iodine atom.

"Lower alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-2-methylpropyl group.

"Lower alkoxy group" means a hydroxyl group of which the hydrogen atom is substituted with the above-mentioned lower alkyl group, including, for example, a methoxy group, an ethoxy group, a propoxy group, an isopropoxy group, a butoxy group, a sec-butoxy group, a tert-butoxy group, a pentyloxy group, an isopentyloxy group, a hexyloxy group, an isohexyloxy group.

"Alkanoyl group" means a carbonyl group to which the above-mentioned lower alkyl group bonds, including, for example, a methylcarbonyl group, an ethylcarbonyl group, a propylcarbonyl group, an isopropylcarbonyl group.

"Lower alkylsulfonyl group" means a sulfonyl group to which the above-defined lower alkyl group bonds, including, for example, a methylsulfonyl group, an ethylsulfonyl group, a propylsulfonyl group, an isopropylsulfonyl group.

"Cycloalkyl group" means a cycloalkyl group having from 3 to 7 carbon atoms and concretely includes, for example, a cyclopropyl group, a cyclobutyl group, a cyclopentyl group, a cyclohexyl group, a cycloheptyl group.

For further disclosing the compounds of the invention of a formula (I):

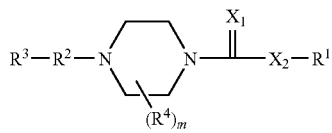

(I)

wherein:
the symbols are the same as above, and the symbols used in formula (I) are described below showing its examples.

The branched alkyl group having from 3 to 9 carbon atoms for $R^1$ includes, for example, an isopropyl group, an isobutyl group, a sec-butyl group, a tert-butyl group, an isoamyl group, a neopentyl group, an isopentyl group, a 1,1-dimethylpropyl group, a 1-methylbutyl group, a 2-methylbutyl group, a 1,2-dimethylpropyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-2-methylpropyl group. Of those, preferred are a tert-butyl group, a 2,2-dimethylpropyl group, an isopropyl group, a 3,3-dimethylbutyl group; and more preferred are a tert-butyl group and a 2,2-dimethylpropyl group.

$X_1$ represents an oxygen atom or a sulfur atom; and $X_1$ is preferably an oxygen atom.

$X_2$ represents an oxygen atom or a single bond.

$R^2$ represents a 6-membered heteroaryl group having 1 or 2 nitrogen atoms, or represents a 5-membered heteroaryl group having, in the ring, from 1 to 3 hetero atoms selected from a group consisting of a nitrogen atom, a sulfur atom and an oxygen atom, in which at least one hetero atom is a nitrogen atom.

"6-Membered heteroaryl group having 1 or 2 nitrogen atoms" for $R^2$ concretely includes, for example, a pyridyl group, a pyrimidinyl group and a pyrazinyl group.

"5-Membered heteroaryl group having, in the ring, from 1 to 3 hetero atoms selected from a group consisting of a nitrogen atom, a sulfur atom and an oxygen atom, in which at least one hetero atom is a nitrogen atom" for $R^2$ concretely includes, for example, an oxazolyl group, an oxadiazolyl group, a thiazolyl group, a thiadiazolyl group, a triazolyl group and a tetrazolyl group. Of those, preferred are an oxadiazolyl group, a thiadiazolyl group, a triazolyl group, a tetrazolyl group.

$R^3$ represents a hydrogen atom, an alkanoylamino group, a methoxycarbonylamino group, a methoxycarbonyl group, a carbamoyl group, a lower alkylsulfonylamino group, a nitro group, a lower alkyl group (the lower alkyl group may be substituted with a hydroxy group or a halogen atom), a lower alkoxy group, an amino group, a halogen atom or a cyano group, or represents a 6-membered heteroaryl group having 1 or 2 nitrogen atoms or a 5-membered heteroaryl group having, in the ring, from 1 to 3 hetero atoms selected from a group consisting of a nitrogen atom, a sulfur atom and an oxygen atom, which may optionally have 1 or 2 substituents selected from the above-mentioned substituent group α or $R^2$ and $R^3$, taken together, represent a group of a formula (II):

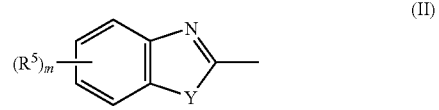

(II)

wherein the symbols are the same as above.

"Alkanoylamino group" for $R^3$ means an amino group to which the above-defined alkanoylamino group bonds, and concretely includes, for example, an acetylamino group, an ethylcarbonylamino group, an isopropylcarbonylamino group.

"Lower alkoxycarbonyl group" for $R^3$ means a carbonyl group to which the above-defined lower alkoxy group bonds, and concretely includes, for example, a methoxycarbonyl group, an ethoxycarbonyl group, an isopropylcarbonyl group.

"Lower alkoxycarbonylamino group" for $R^3$ means an amino group to which the above-mentioned lower alkoxycarbonyl group bonds, and concretely includes, for example, a methoxycarbonyl group, an ethoxycarbonyl group, an isopropylcarbonyl group.

"Lower alkylsulfonylamino group" for $R^3$ means an amino group to which the above-defined lower alkylsulfonyl group bonds, and concretely includes, for example, a methylsulfonylamino group, an ethylsulfonylamino group, an isopropylsulfonylamino group.

"Lower alkyl group" for $R^3$ means the same group as the above-defined lower alkyl group, or means the above-defined lower alkyl group in which from 1 to 3 hydrogen atoms are substituted with a hydroxy group or the above-defined halogen atom. Concretely, it includes, for example, a methyl group, an ethyl group, an isopropyl group, a propyl group, a tert-butyl group, a trifluoromethyl group, a difluoromethyl group, a hydroxymethyl group, and a hydroxyethyl group.

"Lower alkoxy group" for $R^3$ means the same group as the above-defined lower alkoxy group, and concretely includes, for example, a methoxy group, an ethoxy group, an isopropyloxy group.

"Halogen atom" for $R^3$ means the same group as the above-defined halogen atom, and concretely includes, for example, a fluorine atom, a chlorine atom, a bromine atom.

"6-Membered heteroaryl group having 1 or 2 nitrogen atoms" for $R^3$ concretely includes, for example, a pyridinyl group, a pyrimidinyl group, a pyridazinyl group, a pyrazinyl group.

"5-Membered heteroaryl group having, in the ring, from 1 to 3 hetero atoms selected from a group consisting of a nitrogen atom, a sulfur atom and an oxygen atom" for $R^3$ means a 5-membered heteroaryl group in which from 1 to 3 constitutive atoms are hetero atoms selected from a group consisting of a nitrogen atom, a sulfur atom and an oxygen atom, and this concretely includes, for example, an oxadiazolyl group, a thiadiazolyl group, a triazolyl group and a tetrazolyl group.

The 6-membered heteroaryl group having 1 or 2 nitrogen atoms, and the 5-membered heteroaryl group having, in the ring, from 1 to 3 hetero atoms selected from a group consisting of a nitrogen atom, a sulfur atom and an oxygen atom may have 1 or 2 substituents selected from the above-mentioned substituent group α. In case where the 6-membered heteroaryl group or the 5-membered heteroaryl group has 2 such substituents, then the substituents may be the same or different.

"Lower alkoxycarbonyl group" of the substituent means the same group as the above-mentioned lower alkoxycarbonyl group, including, for example, a methoxycarbonyl group, an ethoxycarbonyl group, an isopropylcarbonyl group.

"Lower alkylsulfanyl group" of the substituent means a sulfanyl group to which the above-defined lower alkyl group bonds, and concretely includes, for example, a methylsulfanyl group, an ethylsulfanyl group, an isopropylsulfanyl group.

"Lower alkyl group" of the substituent means the same group as the above-defined lower alkyl group, or means the above-defined lower alkyl group substituted with the above-defined halogen atom, lower alkoxy group or hydroxyl group, and concretely it includes, for example, a methyl group, an ethyl group, an isopropyl group, a trifluoromethyl group, a trichloromethyl group, a 1-hydroxyethyl group, a methoxymethyl group, an ethoxymethyl group, a 1-hydroxy-1-methylethyl group, a difluoromethyl group.

Cycloalkyl group of the substituent means the same cycloalkyl group of the above-defined cycloalkyl group, concretely including, for example, a cyclopropyl group, a cyclobutyl group, a cyclopentyl group. The cycloalkyl group may be substituted with a hydroxyl group.

"Mono-lower alkylamino group" of the substituent means an amino group in which one hydrogen atom is substituted with the above-defined lower alkyl group, concretely including, for example, a methylamino group, an ethylamino group, an isopropylamino group.

"Di-lower alkylamino group" of the substituent means an amino group in which two hydrogen atoms are substituted with the same or different, above-defined lower alkyl groups, and in which the same or different lower alkyl groups may bond to each other to form a 5- to 7-membered ring. Concretely, it includes, for example, a dimethylamino group, a diethylamino group, an ethylmethylamino group, a pyrrolidinyl group, a piperidinyl group, a homopiperidinyl group.

The formula (II):

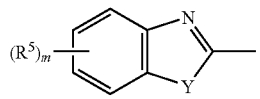

formed by $R^2$ and $R^3$ taken together is described.

Y represents a nitrogen atom, a sulfur atom or an oxygen atom, preferably an oxygen atom.

$R^5$ represents a lower alkyl group, a lower alkoxy group or a halogen atom.

"Lower alkyl group" for $R^5$ means the same group as the above-defined lower alkyl group, concretely including, for example, a methyl group, an ethyl group, a propyl group, an isopropyl group.

"Lower alkoxy group" for $R^5$ means the same group as the above-defined lower alkoxy group, concretely including, for example, a methoxy group, an ethoxy group, a propyloxy group, an isopropyloxy group.

"Halogen atom" for $R^5$ means the same group as the above-defined halogen atom, concretely including, for example, a fluorine atom, a chlorine atom, a bromine atom.

m indicates an integer of from 0 to 4. m is preferably 0 or 1.

Though falling within the scope of formula (I), 1-(3,3-dimethyl-1-oxobutyl)-4-(2-pyridinyl)-piperazine, 1-(3-methyl-1-oxobutyl)-4-(2-pyridinyl)-piperazine, 1-(3-methyl-1-oxobutyl)-4-(2-pyrimidinyl)-piperazine, 1-(3,3-dimethyl-1-oxobutyl)-4-(2-pyrimidinyl)-piperazine, 1-(3,3-dimethyl-1-oxobutyl)-4-[4-(trifluoromethyl)-2-pyridinyl]-piperazine, 1,1-dimethylethyl 4-[5-(hydroxymethyl)-1,2,4-oxadiazol-3-yl]-1-piperazinecarboxylate, 1,1-dimethylethyl 4-[5-(3-chloro-2-thienyl)-1,2,4-oxadiazol-3-yl]-1-piperazinecarboxylate, 1,1-dimethylethyl 4-[5-(3-bromo-2-furanyl)-1,2,4-oxadiazol-3-yl]-1-piperazinecarboxylate, and 1,1-dimethylethyl 4-[5-(chloromethyl)-1,2,4-oxadiazol-3-yl]-1-piperazinecarboxylate are excluded from the compounds (I) of the invention.

One embodiment of the compounds of the invention is the following case (A):

(A) Of the compounds of formula (I), 1-(3,3-dimethyl-1-oxobutyl)-4-(2-pyridinyl)-piperazine, 1-(3-methyl-1-oxobutyl)-4-(2-pyridinyl)-piperazine, 1-(3-methyl-1-oxobutyl)-4-(2-pyrimidinyl)-piperazine, 1-(3,3-dimethyl-1-oxobutyl)-4-(2-pyrimidinyl)-piperazine, 1-(3,3-dimethyl-1-oxobutyl)-4-[4-(trifluoromethyl)-2-pyridinyl]-piperazine, and those where $X_2$ is an oxygen atom and $R^1$ is a tert-butyl group are excluded.

Another preferred embodiment of the compounds of the invention is, for example, the above case (A) of formula (I) where $X_1$ is an oxygen atom.

Also preferred as the compounds of the invention is the above case (A) of formula (I) where $X_1$ is an oxygen atom, $R^2$ is a 6-membered heteroaryl group having 1 or 2 nitrogen atoms, $R^3$ is a hydrogen atom, an alkanoylamino group, a methoxycarbonylamino group, a methoxycarbonyl group, a carbamoyl group, a lower alkylsulfonylamino group, a nitro group, a lower alkyl group (the lower alkyl group may be substituted with a hydroxy group or a halogen atom), a lower alkoxy group, an amino group, a halogen atom or a cyano group, or represents a 5-membered heteroaryl group having, in the ring, from 1 to 4 hetero atoms selected from a group consisting of a nitrogen atom, a sulfur atom and an oxygen atom, which may have 1 or 2 substituents selected from the substituent group α.

Another preferred embodiment of the compounds of the invention is, for example, the above case (A) of formula (I) where $X_1$ is an oxygen atom, $R^2$ is a 6-membered heteroaryl group having 1 or 2 nitrogen atoms, $R^3$ is a hydrogen atom, an alkanoylamino group, a methoxycarbonylamino group, a methoxycarbonyl group, a carbamoyl group, a lower alkylsulfonylamino group, a nitro group, a lower alkyl group (the lower alkyl group may be substituted with a hydroxy group or a halogen atom), a lower alkoxy group, an amino group, a halogen atom or a cyano group.

Another preferred embodiment of the compounds of the invention is, for example, the above case (A) of formula (I) where $X_1$ is an oxygen atom, $R^2$ is a 6-membered heteroaryl group having 1 or 2 nitrogen atoms, $R^3$ is a 5-membered heteroaryl group having, in the ring, from 1 to 4 hetero atoms selected from a group consisting of a nitrogen atom, a sulfur atom and an oxygen atom, which may have 1 or 2 substituents selected from the substituent group α.

Another preferred embodiment of the compounds of the invention is, for example, a case where $X_1$ is an oxygen atom, $R^2$ is a 6-membered heteroaryl group having 1 or 2 nitrogen atoms, $R^3$ is an oxadiazolyl group, a thiadiazolyl group, a triazolyl group, a tetrazolyl group or a thiazolyl group, which may have 1 or 2 substituents selected from the substituent group α.

Another preferred embodiment of the compounds of the invention is, for example, the above case (A) of formula (I) where $X_1$ is an oxygen atom, and $R^2$ and $R^3$, taken together, represent a group of a formula (II):

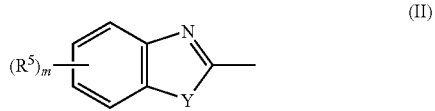

(II)

(wherein Y represents a nitrogen atom, a sulfur atom or an oxygen atom; $R^5$ represents a lower alkyl group, a lower alkoxy group or a halogen atom).

Another preferred embodiment of the compounds of the invention is, for example, the above case (A) of formula (I) where $X_1$ is an oxygen atom, and $R^3$ is a 5-membered heteroaryl group having, in the ring, from 1 to 4 hetero atoms selected from a group consisting of a nitrogen atom, a sulfur atom and an oxygen atom, in which at least one hetero atom is a nitrogen atom.

Another preferred embodiment of the compounds of the invention is, for example, the above case (A) of formula (I) where $X_1$ is an oxygen atom, and $R^3$ is an oxadiazolyl group, a triazolyl group or a pyridinyl group.

As one preferred embodiment thereof, the mGluR1 antagonist of the invention comprises a compound of formula (I) or its pharmaceutically acceptable salt.

Another preferred embodiment of the mGluR1 antagonist of the invention comprises, for example, a compound of formula (I) or its pharmaceutically acceptable salt where $X_1$ is an oxygen atom.

Another preferred embodiment of the mGluR1 antagonist of the invention comprises, for example, a compound of formula (I) or its pharmaceutically acceptable salt where $X_1$ is an oxygen atom, $R^2$ is a 6-membered heteroaryl group having 1 or 2 nitrogen atoms, $R^3$ is a hydrogen atom, an alkanoylamino group, a methoxycarbonylamino group, a methoxycarbonyl group, a carbamoyl group, a lower alkylsulfonylamino group, a nitro group, a lower alkyl group (the lower alkyl group may be substituted with a hydroxy group or a halogen atom), a lower alkoxy group, an amino group, a halogen atom or a cyano group, or represents a 5-membered heteroaryl group having, in the ring, from 1 to 4 hetero atoms selected from a group consisting of a nitrogen atom, a sulfur atom and an oxygen atom, which may have 1 or 2 substituents selected from the substituent group α.

Another preferred embodiment of the mGluR1 antagonist of the invention comprises, for example, a compound of formula (I) or its pharmaceutically acceptable salt where $X_1$ is an oxygen atom, $R^2$ is a 6-membered heteroaryl group having 1 or 2 nitrogen atoms, $R^3$ is a hydrogen atom, an alkanoylamino group, a methoxycarbonylamino group, a methoxycarbonyl group, a carbamoyl group, a lower alkylsulfonylamino group, a nitro group, a lower alkyl group (the lower alkyl group may be substituted with a hydroxy group or a halogen atom), a lower alkoxy group, an amino group, a halogen atom or a cyano group.

Another preferred embodiment of the mGluR1 antagonist of the invention comprises, for example, a compound of formula (I) or its pharmaceutically acceptable salt where $X_1$ is an oxygen atom, $R^2$ is a 6-membered heteroaryl group having 1 or 2 nitrogen atoms, $R^3$ is a 5-membered heteroaryl group having, in the ring, from 1 to 4 hetero atoms selected from a group consisting of a nitrogen atom, a sulfur atom and an oxygen atom, which may have 1 or 2 substituents selected from the substituent group α.

Another preferred embodiment of the mGluR1 antagonist of the invention comprises, for example, a compound of formula (I) or its pharmaceutically acceptable salt where $X_1$ is an oxygen atom, $R^2$ is a 6-membered heteroaryl group having 1 or 2 nitrogen atoms, $R^3$ is an oxadiazolyl group, a thiadiazolyl group, a triazolyl group, a tetrazolyl group or a thiazolyl group, which may have 1 or 2 substituents selected from the substituent group α.

Another preferred embodiment of the mGluR1 antagonist of the invention comprises, for example, a compound of formula (I) or its pharmaceutically acceptable salt where $X_1$ is an oxygen atom, and $R^2$ and $R^3$, taken together, represent a group of a formula (II):

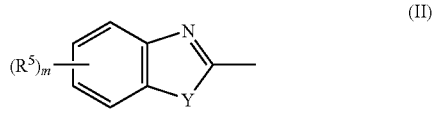

(II)

wherein:
Y represents a nitrogen atom, a sulfur atom or an oxygen atom;
$R^5$ represents a lower alkyl group, a lower alkoxy group or a halogen atom.

The compounds of the invention concretely include, for example, the following:
2,2-dimethylpropyl 4-(4-methylpyridin-2-yl)-1-piperazinecarboxylate,
2,2-dimethylpropyl 4-(4-cyanopyridin-2-yl)-1-piperazinecarboxylate,
2,2-dimethylpropyl 4-(benzoxazol-2-yl)-1-piperazinecarboxy late,
2,2-dimethylpropyl 4-(6-chloropyrimidin-4-yl)-1-piperazinecarboxylate,
2,2-dimethylpropyl 4-[4-(methoxycarbonyl)pyridin-2-yl]-1-piperazinecarboxylate,
2,2-dimethylpropyl 4-(4-methoxypyridin-2-yl)-1-piperazinecarboxylate, 2,2-dimethylpropyl 4-(6-chloropyridazin-3-yl)-1-piperazinecarboxylate,
2,2-dimethylpropyl 4-(4-nitropyridin-2-yl)-1-piperazinecarboxylate,
2,2-dimethylpropyl 4-(5-chloropyridin-2-yl)-1-piperazinecarboxylate,
2,2-dimethylpropyl 4-(6-methylpyridin-2-yl)-1-piperazinecarboxylate,
2,2-dimethylpropyl 4-(6-methoxypyridin-2-yl)-1-piperazinecarboxylate,
2,2-dimethylpropyl 4-[4-(trifluoromethyl)pyridin-2-yl]-1-piperazinecarboxylate,
2,2-dimethylpropyl 4-(5-methylpyridin-2-yl)-1-piperazinecarboxylate,
2,2-dimethylpropyl 4-(4,6-dimethylpyrimidin-2-yl)-1-piperazinecarboxylate,
2,2-dimethylpropyl 4-(thiazol-2-yl)-1-piperazinecarboxylate,
2,2-dimethylpropyl 4-(6-chloropyridin-2-yl)-1-piperazinecarboxylate,
2,2-dimethylpropyl 4-(3-methylpyridin-2-yl)-1-piperazinecarboxylate,
2,2-dimethylpropyl 4-(pyridin-2-yl)-1-piperazinecarboxylate,
2,2-dimethylpropyl 4-(pyrimidin-2-yl)-1-piperazinecarboxylate,
2,2-dimethylpropyl 4-(4-aminopyridin-2-yl)-1-piperazinecarboxylate,
2,2-dimethylpropyl 4-[4-(acetylamino)pyridin-2-yl]-1-piperazinecarboxylate,
2,2-dimethylpropyl 4-{4-[(methoxycarbonyl)amino]pyridin-2-yl}-1-piperazinecarboxylate,
2,2-dimethylpropyl 4-[4-(propionylamino)pyridin-2-yl]-1-piperazinecarboxylate,
2,2-dimethylpropyl 4-[4-(hydroxymethyl)pyridin-2-yl]-1-piperazinecarboxylate
2,2-dimethylpropyl 4-(pyrimidin-4-yl)-1-piperazinecarboxylate,
2,2-dimethylpropyl 4-(4-{5-[(1S)-1-hydroxyethyl]-1,2,4-oxadiazol-3-yl}pyridin-2-yl)-1-piperazinecarboxylate,
2,2-dimethylpropyl 4-(4-{5-[(1R)-1-hydroxyethyl]-1,2,4-oxadiazol-3-yl}pyridin-2-yl)-1-piperazinecarboxylate,
2,2-dimethylpropyl 4-[4-(5-methyl-1,2,4-oxadiazol-3-yl)pyridin-2-yl]-1-piperazinecarboxylate,
2,2-dimethylpropyl 4-[4-(5-methoxy-1,2,4-oxadiazol-3-yl)pyridin-2-yl]-1-piperazinecarboxylate,
2,2-dimethylpropyl 4-[4-(5-cyclopropyl-1,2,4-oxadiazol-3-yl)pyridin-2-yl]-1-piperazinecarboxylate,
2,2-dimethylpropyl 4-{4-[5-(methoxycarbonyl)-1,2,4-oxadiazol-3-yl]pyridin-2-yl}-1-piperazinecarboxylate,
2,2-dimethylpropyl 4-{4-[5-(trichloromethyl)-1,2,4-oxadiazol-3-yl]pyridin-2-yl}-1-piperazinecarboxylate,
2,2-dimethylpropyl 4-{4-[5-(trifluoromethyl)-1,2,4-oxadiazol-3-yl]pyridin-2-yl}-1-piperazinecarboxylate,
2,2-dimethylpropyl 4-[4-(5-methoxy-1,2,4-oxadiazol-3-yl)pyridin-2-yl]-1-piperazinecarboxylate,
2,2-dimethylpropyl 4-[4-(1,2,4-oxadiazol-3-yl)pyridin-2-yl]-1-piperazinecarboxylate,
2,2-dimethylpropyl 4-[4-(5-carbamoyl-1,2,4-oxadiazol-3-yl)pyridin-2-yl]-1-piperazinecarboxylate,
2,2-dimethylpropyl 4-{4-[5-(dimethylamino)-1,2,4-oxadiazol-3-yl]pyridin-2-yl}-1-piperazinecarboxylate,
2,2-dimethylpropyl 4-[4-(5-amino-1,2,4-oxadiazol-3-yl)pyridin-2-yl]-1-piperazinecarboxylate,
2,2-dimethylpropyl 4-{4-[5-(methylamino)-1,2,4-oxadiazol-3-yl]pyridin-2-yl}-1-piperazinecarboxylate,
2,2-dimethylpropyl 4-{4-[5-(pyrrolidin-1-yl)-1,2,4-oxadiazol-3-yl]pyridin-2-yl}-1-piperazinecarboxylate,
2,2-dimethylpropyl 4-[4-(3-methyl-1,2,4-oxadiazol-5-yl)pyridin-2-yl]-1-piperazinecarboxylate,
2,2-dimethylpropyl 4-{4-[5-(methylamino)-1,2,4-thiadiazol-3-yl]pyridin-2-yl}-1-piperazinecarboxylate,
2,2-dimethylpropyl 4-[4-(5-methyl-1,2,4-triazol-3-yl)pyridin-2-yl]-1-piperazinecarboxylate,
2,2-dimethylpropyl 4-[4-(tetrazol-5-yl)pyridin-2-yl]-1-piperazinecarboxylate,
2,2-dimethylpropyl 4-{4-[5-(methylthio)-1,2,4-oxadiazol-3-yl]pyridin-2-yl}-1-piperazinecarboxylate,
2,2-dimethylpropyl 4-(2-methylthiazol-4-yl)-1-piperazinecarboxylate,
tert-butyl 4-(5-tert-butyl-1,2,4-oxadiazol-3-yl)-1-piperazinecarboxylate,
tert-butyl 4-(5-phenyl-1,2,4-oxadiazol-3-yl)-1-piperazinecarboxylate,
tert-butyl 4-[5-(2,2-dimethylpropyl)-1,2,4-oxadiazol-3-yl]-1-piperazinecarboxylate,
tert-butyl 4-[5-(2-chlorophenyl)-1,2,4-oxadiazol-3-yl]-1-piperazinecarboxylate,
tert-butyl 4-(5-tert-butyl-1,2,4-triazol-3-yl)-1-piperazinecarboxylate,
tert-butyl 4-[5-(pyridin-3-yl)-1,2,4-oxadiazol-3-yl]-1-piperazinecarboxylate,
1-(4,4-dimethylpentanoyl)-4-(4-cyanopyridin-2-yl)piperazine,
1-(4,4-dimethylpentanoyl)-4-(4-cyanopyrimidin-2-yl)piperazine,
1-(4,4-dimethylpentanoyl)-4-(4-methylpyridin-2-yl)piperazine,
1-(4,4-dimethylpentanoyl)-4-{4-[5-(methoxymethyl)-1,2,4-oxadiazol-3-yl]pyridin-2-yl}piperazine,
1-(4,4-dimethylpentanoyl)-4-[4-(5-methyl-1,2,4-oxadiazol-3-yl)pyridin-2-yl]piperazine,
1-(4,4-dimethylpentanoyl)-4-(4-{5-[(1S)-hydroxyethyl]-1,2,4-oxadiazol-3-yl}pyridin-2-yl)piperazine,
1-(4,4-dimethylpentanoyl)-4-(4-{5-[(1R)-hydroxyethyl]-1,2,4-oxadiazol-3-yl}pyridin-2-yl)piperazine,
1-(4,4-dimethylpentanoyl)-4-{4-[5-(hydroxymethyl)-1,2,4-oxadiazol-3-yl]pyridin-2-yl}piperazine,
1-(4,4-dimethylpentanoyl)-4-[4-(5-cyclopropyl-1,2,4-oxadiazol-3-yl)pyridin-2-yl]piperazine,
1-(4,4-dimethylpentanoyl)-4-{4-[5-(1-hydroxy-1-methylethyl)-1,2,4-oxadiazol-3-yl]pyridin-2-yl}piperazine,
1-(4,4-dimethylpentanoyl)-4-{4-[5-(difluoromethyl)-1,2,4-oxadiazol-3-yl]pyridin-2-yl}piperazine,
1-(4,4-dimethylpentanoyl)-4-[4-(5-cyclopropyl-1,2,4-oxadiazol-3-yl)pyrimidin-2-yl]piperazine,
1-(4,4-dimethylpentanoyl)-4-{4-[5-(methoxymethyl)-1,2,4-oxadiazol-3-yl]pyrimidin-2-yl}piperazine,
1-(4,4-dimethylpentanoyl)-4-[4-(5-methyl-1,2,4-oxadiazol-3-yl)pyrimidin-2-yl]piperazine,
1-(4,4-dimethylpentanoyl)-4-{4-[5-(1-hydroxycyclopropyl)-1,2,4-oxadiazol-3-yl]pyrimidin-2-yl}piperazine,
1-(4,4-dimethylpentanoyl)-4-{4-[5-(dimethylamino)-1,2,4-oxadiazol-3-yl]pyridin-2-yl}piperazine,
1-(4,4-dimethylpentanoyl)-4-{4-[5-(methylamino)-1,2,4-oxadiazol-3-yl]pyridin-2-yl}piperazine,
1-(4,4-dimethylpentanoyl)-4-[4-(1,2,4-oxadiazol-3-yl)pyridin-2-yl]piperazine,
1-(4,4-dimethylpentanoyl)-4-[4-(5-amino-1,2,4-oxadiazol-3-yl)pyridin-2-yl]piperazine.

Production methods for the compounds of the invention are described below.

Compounds (I-1):

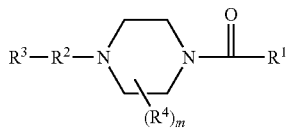

wherein the symbols are the same as above, and the compounds (I-1) may be produced, for example, according to the following method:

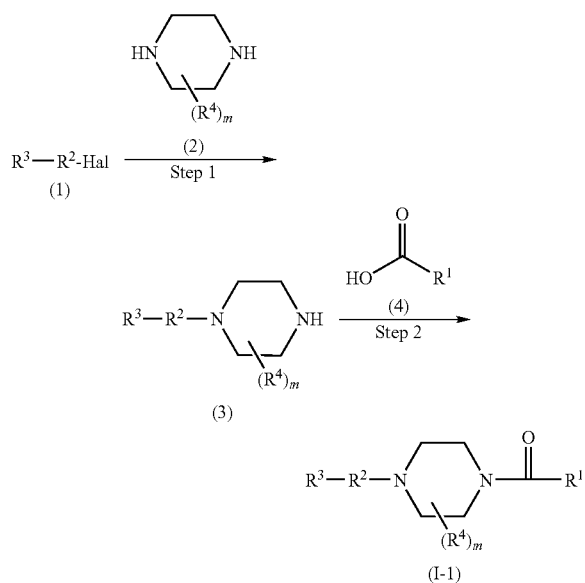

wherein Hal represents a halogen atom, and the other symbols are the same as above.]

(Step 1)

his step is a process for producing a compound (3) by reacting a compound (1) with a piperazine derivative (2).

Hal in the compound (1) represents a halogen atom, concretely including, for example, a fluorine atom, a chlorine atom, a bromine atom.

The compounds (1) and (2) may be commercial products, or may be produced from commercial products according to a method well known to those skilled in the art, or according to a method similar to it, or according to a combination of the method and an ordinary method.

The compound (1) includes, for example, 2-fluoro-4-methylpyridine, 2-chloro-4-cyanopyridine, 2-chlorobenzoxazole, 4,6-dichloropyrimidine, methyl 2-chloroisonicotinate, 2-chloro-4-methoxypyridine, 3,6-dichloropyridazine, 2-chloro-4-nitropyridine, 2,5-dichloropyridine, 2-chloro-6-methylpyridine, 2-chloro-6-methoxypyridine, 2-chloro-4-(trifluoromethyl)pyridine, 2-chloro-5-methylpyridine, 2-chloro-4,6-dimethylpyridine, 2-bromothiazole, 2,6-dichloropyridine, 2-chloro-3-methylpyridine, 2-chloro-4-cyanopyrimidine.

The amount of the compound (2) to be used in this step may be generally from 2 to 10 equivalents relative to one equivalent of the compound (1), preferably from 2 to 5 equivalents.

The reaction solvent may be absent, or not specifically defined, it may be any one not interfering with the reaction. For example, it includes dimethyl sulfoxide, dimethylformamide, ethanol, pyridine.

The reaction temperature may be generally from room temperature to 200° C., preferably from 100° C. to 150° C.

The reaction time may be generally from 1 to 10 hours, preferably from 1 to 4 hours.

Thus obtained, the compound (3) may be subjected to the next step, after isolated and purified in any known isolation and purification method of, for example, concentration, concentration under reduced pressure, reprecipitation, solvent extraction, crystallization or chromatography, or not isolated.

(Step 2)

This step is a process for producing a compound (I-1) of the invention by reacting the compound (3) obtained in the above step 1 and a compound (4).

The reaction in this step is ordinary amidation that may be effected according to a method described in publications (e.g., Bases and Experiments of Peptide Synthesis, Nobuo Izumiya et al., Maruzen, 1983; Comprehensive Organic Synthesis, Vol. 6, Pergamon Press, 1991), or a method similar to the method, or a combination of the method and any other ordinary method. Concretely, for example, a condensing agent that is well known to those skilled in the art is used for the reaction; or the reaction may be effected in an ester activation method, a mixed acid anhydride method, an acid chloride method or a carbodiimide method that may be carried out by anyone skilled in the art. The amidation reagent includes, for example, thionyl chloride, oxalyl chloride, N,N-dicyclohexylcarbodiimide, 1-methyl-2-bromopyridinium iodide, N,N'-carbonyldiimidazole, diphenylphosphoryl chloride, diphenylphosphoryl azide, N,N'-disuccinimidyl carbonate, N,N'-disuccinimidyl oxalate, 1-ethyl-3-(3-dimethylaminopropyl)carbodiimide hydrochloride, ethyl chloroformate, isobutyl chloroformate, benzotriazol-1-yloxy-tris(dimethylamino)phosphonium hexafluorophosphate. Of those, preferred are thionyl chloride, 1-ethyl-3-(3-dimethylaminopropyl)carbodiimide hydrochloride, N,N-dicyclohexylcarbodiimide, benzotriazol-1-yloxy-tris(dimethylamino)phosphonium hexafluorophosphate. In the amidation, a base and a condensing promoter may also be used along with the above amidation reagent.

The usable base includes, for example, tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU), 15-azabicyclo[4.3.0]non-5-ene (DBN); and aromatic amines such as pyridine, 4-dimethylaminopyridine, picoline, lutidine, quinoline, isoquinoline. Of those, for example, preferred are tertiary aliphatic amines; and more preferred are triethylamine, N,N-diisopropylethylamine or pyridine.

The usable condensing promoter includes, for example, N-hydroxybenzotriazole hydrate, n-hydroxysuccinimide, N-hydroxy-5-norbornene-2,3-dicarboxyimide, 3-hydroxy-3,4-dihydro-4-oxo-1,2,3-benzotriazole. Of those, preferred is, for example, N-hydroxybenzotriazole.

The amount of the compound (4) or its reactive derivative to be used herein may differ, depending on the type of the compound and the solvent to be used and on the other reaction conditions, but may be generally from 1 to 50 equivalents relative to one equivalent of the compound (4), more preferably from 2 to 10 equivalents.

The compound (4) may be a commercial product, or may be produced from commercial products according to a method well known to those skilled in the art, or according to a method similar to it.

The compound (4) includes, for example, 3-cyclohexylpropionic acid, 3-cyclopentylpropionic acid, 3-noradamantane-carboxylic acid, 2,2,3,3-tetramethylcyclopropane-carboxylic acid, 4-methylpentanoic acid, cyclohexylcarboxylic acid, 3,3-dimethylbutyric acid, 4,4-dimethylvaleric acid.

The amount of the amidation reagent to be used may vary, depending on the type of the compound and the solvent to be used and on the other reaction conditions, but in general, it may be from 1 to 50 equivalents relative to 1 equivalent of the compound (3), preferably from 2 to 10 equivalents.

The amount of the condensation promoter to be used may vary, depending on the type of the compound and the solvent to be used and on the other reaction conditions, but in general, it may be from 1 to 50 equivalents relative to 1 equivalent of the compound (3), preferably from 2 to 10 equivalents.

The amount of the base to be used may vary, depending on the type of the compound and the solvent to be used and on the other reaction conditions, but in general, it may be from 1 to 50 equivalents relative to 1 equivalent of the compound (3), preferably from 2 to 5 equivalents.

Not specifically defined, the reaction solvent to be used in this step includes, for example, chloroform, methylene chloride, pyridine, tetrahydrofuran, diethyl ether, dimethylformamide, N-methylpyrrolidone, dioxane, toluene, benzene, xylene. Of those, preferred are pyridine, chloroform, tetrahydrofuran.

The reaction temperature in this step may be generally from −78° C. to 150° C., preferably from 0° C. to 50° C.

The reaction time in this step may be generally from 30 minutes to 7 days, preferably from 30 minutes to 12 hours.

For the base, the amidation reagent and the condensation promoter to be used in this step, one or more compounds may be used either singly or as combined.

Thus obtained, the compound (I-1) may be isolated and purified in any known isolation and purification method of, for example, concentration, concentration under reduced pressure, crystallization, solvent extraction, reprecipitation or chromatography.

A compound (I-10):

$$R^3-R^2-N\underset{(R^4)_m}{\overset{}{\bigcirc}}N-\overset{O}{\overset{\|}{C}}-O-R^1 \quad (I\text{-}10)$$

wherein the symbols are the same as above, and the compound of the invention may be produced, for example, according to the following method:

$$R^3-R^2-N\underset{(R^4)_m}{\overset{}{\bigcirc}}NH + Cl-\overset{O}{\overset{\|}{C}}-O-R^1 \xrightarrow[\text{Step 3-1}]{(4\text{-}1)}$$
(3)

$$R^3-R^2-N\underset{(R^4)_m}{\overset{}{\bigcirc}}N-\overset{O}{\overset{\|}{C}}-O-R^1$$
(I-10)

wherein the symbols are the same as above.

(Step 3-1)

This step is a process for producing a compound (I-10) of the invention by reacting a compound (4-1) and the compound (3) obtained in the above step 1.

The compound (4-1) to be used in this step concretely includes, for example, neopentyl chloroformate, pentyl chloroformate, 2-methylpropyl chloroformate, butyl chloroformate.

The compound (4-1) may be a commercial product, or may be produced from commercial products according to a method well known to those skilled in the art.

The amount of the compound (4-1) to be used may be generally from 1 to 10 equivalents relative to 1 equivalent of the compound (3), preferably from 1 to 5 equivalents.

The reaction in this step may be attained in the presence of a base.

The usable base includes, for example, tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU), 1,5-azabicyclo[4.3.0]non-5-ene (DBN); and aromatic amines such as pyridine, 4-dimethylaminopyridine, picoline, lutidine, quinoline, isoquinoline. Of those, preferred are pyridine, triethylamine.

Not specifically defined, the reaction solvent may be any one not interfering with the reaction, and, for example, it includes chloroform, methylene chloride, pyridine, acetonitrile, tetrahydrofuran, diethyl ether, dimethylformamide, N-methylpyrrolidone, dioxane, toluene, benzene, xylene. Of those, preferred is chloroform.

The reaction temperature may be generally from −78° C. to 150° C., preferably from 0° C. to 50° C.

The reaction time may be generally from 30 minutes to 48 hours, preferably from 6 hours to 24 hours.

Thus obtained, the compound (I-10) of the invention may be isolated and purified in any known isolation and purification method of, for example, concentration, concentration under reduced pressure, crystallization, solvent extraction, reprecipitation or chromatography.

A compound (I-2)

$$ \text{(I-2)} $$

wherein Y represents a nitrogen atom or CH; and the other symbols are the same as above, and the compound of the invention may be produced, for example, according to the following method:

$$ \text{(Ia)} \xrightarrow[\text{Step 3}]{\text{NH}_2\text{OH·HCl}} $$

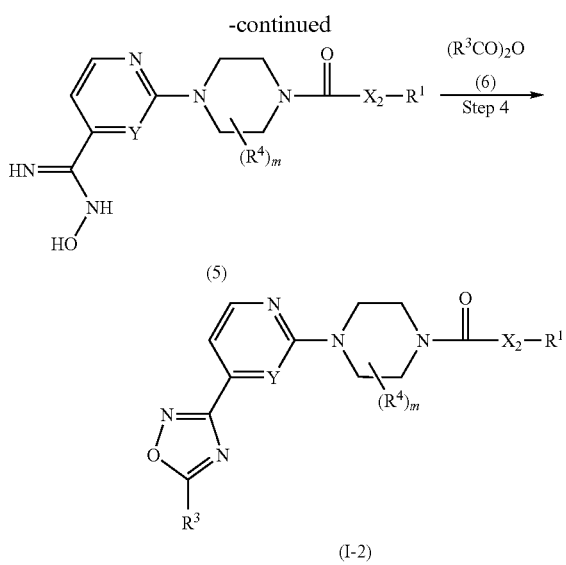

wherein the symbols are the same as above.

(Step 3)

This step is a process for producing a compound (5) by reacting a compound (Ia), which falls within the scope of the compound (I-1) obtained in the above step 2 or the compound (I-10) obtained in the above step 3-1, and hydroxyamine hydrochloride in the presence of a base.

The base to be used in this step includes, for example, potassium carbonate, sodium carbonate, sodium hydroxide, sodium methoxide, sodium ethoxide, triethylamine.

The amount of the base to be used may be generally from 1 to 5 equivalents relative to 1 equivalent of hydroxyamine hydrochloride, preferably from 1 to 2 equivalents.

The amount of hydroxyamine hydrochloride to be used may be generally from 1 to 5 equivalents relative to 1 equivalent of the compound (Ia), preferably from 1 to 2 equivalents.

Not specifically defined, the reaction solvent may be any one not interfering with the reaction, and includes, for example, ethanol, methanol.

The reaction temperature may be generally from −20° C. to the boiling point of the solvent, preferably from room temperature to the boiling point of the solvent.

The reaction time may be generally from 1 hour to 48 hours, preferably from 2 hours to 5 hours.

Thus obtained, the compound (5) may be subjected to the next step, after isolated and purified in any known isolation and purification method of, for example, concentration, concentration under reduced pressure, reprecipitation, solvent extraction, crystallization or chromatography, or not isolated.

(Step 4)

This step is a process for producing a compound (I-2) of the invention by reacting the compound (5) obtained in the above step 3 and a compound (6).

The amount of the compound (6) to be used in this step may be generally from 2 to 50 equivalents relative to 1 equivalent of the compound (5).

The compound (6) includes, for example, acetic anhydride, trichloroacetic anhydride, trifluoroacetic anhydride, propionic anhydride.

The reaction solvent may be absent, or not specifically defined, it may be any one not interfering with the reaction. For example, it includes tetrahydrofuran, pyridine, toluene.

The reaction temperature may be generally from 0° C. to the boiling point of the solvent, preferably from room temperature to the boiling point of the solvent.

The reaction time may be generally from 1 hour to 48 hours, preferably from 2 hours to 5 hours.

In this step, a compound (6-1) $R^3C(O)Cl$ may be used in place of the compound (6).

The amount of the compound (6-1) to be used in this step may be generally from 1 to 10 equivalents relative to 1 equivalent of the compound (5), preferably from 1 to 3 equivalents.

Not specifically defined, the reaction solvent may be any one not interfering with the reaction, and includes, for example, pyridine, triethylamine, toluene.

The reaction temperature may be generally from 0° C. to the boiling point of the solvent, preferably from room temperature to the boiling point of the solvent.

The reaction time may be generally from 1 hour to 48 hours, preferably from 1 hour to 5 hours.

In this step, a compound (6-2) $R^3C(O)OMe$ may be used in place of the compound (6) or the compound (6-1).

The amount of the compound (6-2) to be used in this step may be generally from 1 to 5 equivalents relative to 1 equivalent of the compound (5), preferably from 1 to 2 equivalents.

In the reaction with the compound (6-2), a base may be added to the reaction system.

The amount of the base may be generally from 1 to 3 equivalents relative to 1 equivalent of the compound (5), preferably from 1 to 1.5 equivalents.

The base includes, for example, sodium hydride, potassium hydride.

Not specifically defined, the reaction solvent may be any one not interfering with the reaction, and includes, for example, tetrahydrofuran, diethyl ether, dioxane.

The reaction temperature may be generally from 0° C. to the boiling point of the solvent, preferably from room temperature to the boiling point of the solvent.

The reaction time may be generally from 0.5 hours to 5 hours, preferably from 0.5 hours to 2 hours.

Thus obtained, the compound (I-2) of the invention may be isolated in any known isolation and purification method of, for example, concentration, concentration under reduced pressure, reprecipitation, solvent extraction, crystallization or chromatography.

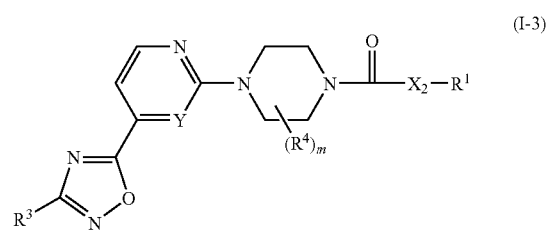

of the invention may be produced, for example, according to the following method:

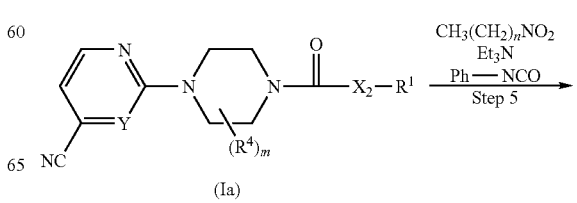

-continued

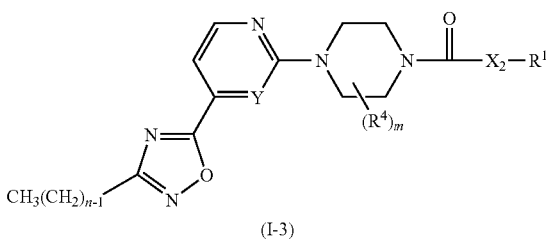
(I-3)

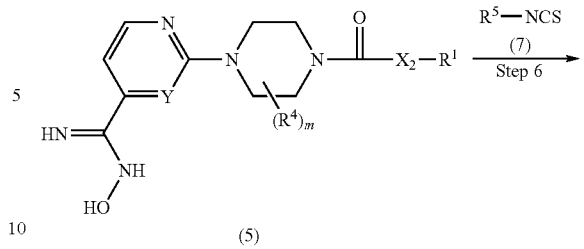
(5)

wherein n indicates an integer of from 1 to 3; and the other symbols are the same as above.

(Step 5)

This step is a process for producing a compound (I-3) of the invention by reacting the above compound (Ia) with a nitroalkane and phenyl isocyanate in the presence of triethylamine.

The amount of the nitroalkane to be used in this step may be generally from 1 to 5 equivalents relative to 1 equivalent of the compound (Ia), preferably from 1 to 2 equivalents.

The amount of phenyl isocyanate to be used in this step may be generally from 2 to 10 equivalents relative to 1 equivalent of the compound (Ia), preferably from 2 to 4 equivalents.

The amount of triethylamine to be used in this step may be generally from 0.01 to 0.5 equivalents relative to 1 equivalent of the compound (Ia), preferably from 0.01 to 0.1 equivalents.

Not specifically defined, the reaction solvent may be any one not interfering with the reaction, and includes, for example, toluene, benzene, xylene.

The reaction temperature may be generally from room temperature to the boiling point of the solvent, preferably the boiling point of the solvent.

The reaction time may be generally from 1 to 24 hours, preferably from 2 to 5 hours.

Thus obtained, the compound (I-3) of the invention may be isolated in any known isolation and purification method of, for example, concentration, concentration under reduced pressure, reprecipitation, solvent extraction, crystallization or chromatography.

A compound (I-4):

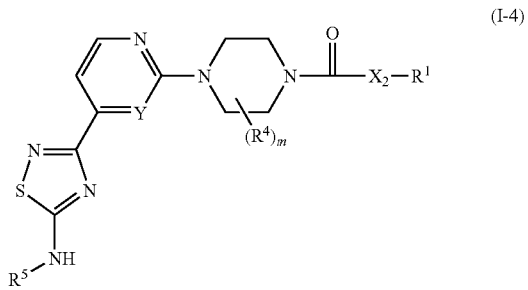
(I-4)

of the invention may be produced, for example, according to the following method:

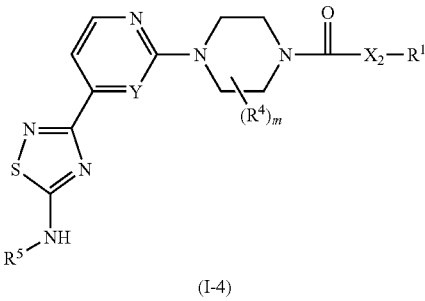
(I-4)

(Step 6)

This step is a process for producing a compound of formula (I-4) by reacting the compound (5) obtained in the above step 3 and a compound (7).

The compound (7) to be used in this step includes methyl isothiocyanate, ethyl isothiocyanate, propyl isothiocyanate.

The amount of the compound (7) to be used may be generally from 1 to 3 equivalents relative to 1 equivalent of the compound (5), preferably from 1 to 2 equivalents.

Not specifically defined, the reaction solvent may be any one not interfering with the reaction, and includes, for example, dimethylformamide, acetonitrile.

The reaction temperature may be generally from room temperature to 150° C., preferably from 80 to 120° C.

The reaction time may be generally from 1 to 10 hours, preferably from 1 to 5 hours.

Thus obtained, the compound (I-4) of the invention may be isolated in any known isolation and purification method of, for example, concentration, concentration under reduced pressure, reprecipitation, solvent extraction, crystallization or chromatography.

A compound (I-5):

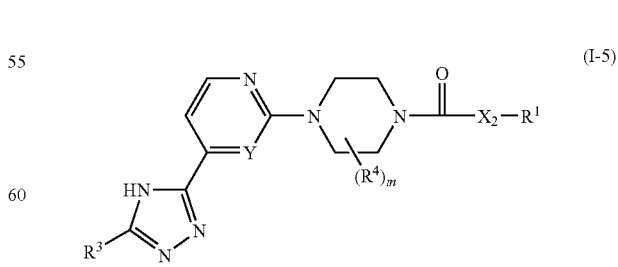
(I-5)

wherein the symbols are the same as above, and the compound of the invention may be produced, fro example, according to the following method:

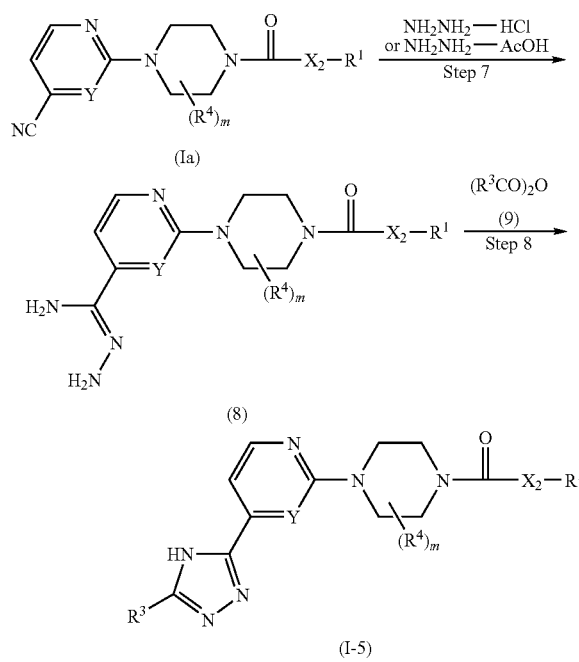

(Step 7)

This step is a process for producing a compound (8) by reacting the above compound (Ia) and hydrazine hydrochloride or hydrazine acetate in the presence of a base.

The base to be used in this step includes, for example, sodium carbonate, potassium carbonate, sodium hydroxide.

The amount of the base to be used may be generally from 1 to 10 equivalents relative to 1 equivalent of the compound (Ia), preferably from 1 to 3 equivalents.

The amount of hydrazine hydrochloride to be used may be generally from 1 to 10 equivalents relative to 1 equivalent of the compound (Ia), preferably from 1 to 3 equivalents.

Not specifically defined, the reaction solvent may be any one not interfering with the reaction, and includes, for example, ethanol, methanol.

The reaction temperature may be generally from −20° C. to the boiling point of the solvent, preferably from room temperature to the boiling point of the solvent.

The reaction time may be generally from 1 to 48 hours, preferably from 2 to 5 hours.

Thus obtained, the compound (8) may be isolated in any known isolation and purification method of, for example, concentration, concentration under reduced pressure, crystallization, solvent extraction, reprecipitation or chromatography.

(Step 8)

This step is a process for producing a compound (I-5) of the invention by reacting the compound (8) obtained in the above step 7 and a compound (9).

The amount of the compound (9) to be used in this step may be generally from 2 to 50 equivalents relative to 1 equivalent of the compound (8).

The compound (9) includes, for example, acetic anhydride, trichloroacetic anhydride, trifluoroacetic anhydride, propionic anhydride.

Not specifically defined, the reaction solvent may be any one not interfering with the reaction, and includes, for example, tetrahydrofuran, pyridine, toluene.

The reaction temperature may be generally from 0° C. to the boiling point of the solvent, preferably from room temperature to the boiling point of the solvent.

The reaction time may be generally from 1 to 48 hours, preferably from 2 to 5 hours.

Thus obtained, the compound (I-5) of the invention may be isolated in any known isolation and purification method of, for example, concentration, concentration under reduced pressure, crystallization, solvent extraction, reprecipitation or chromatography.

A compound (I-6):

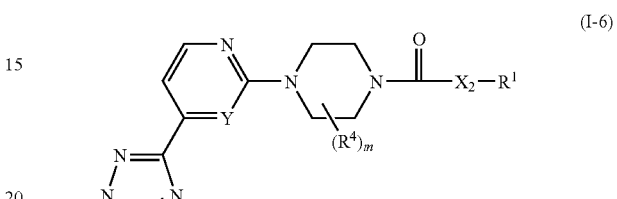

wherein the symbols are the same as above, and the compound of the invention may be produced, for example, according to the following method:

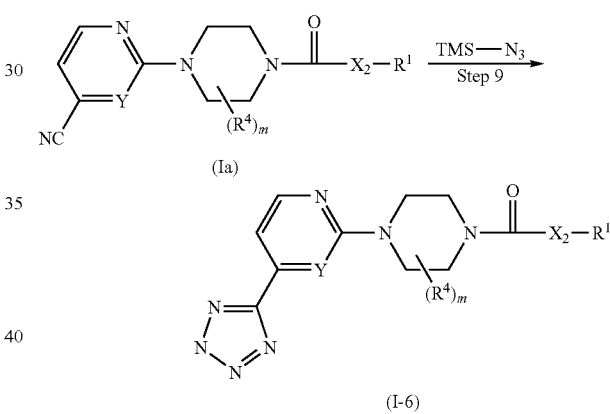

wherein TMS represents a trimethylsilyl group; and the other symbols are the same as above.

(Step 9)

This step is a process for producing a compound (I-6) of the invention by reacting the above compound (Ia) and trimethylsilylazide in the presence of a catalytic amount of dibutyltin (IV) oxide.

The amount of trimethylsilylazide to be used in this step may be generally from 1 to 5 equivalents relative to 1 equivalent of the compound (Ia), preferably from 2 to 3 equivalents.

Not specifically defined, the reaction solvent may be any one not interfering with the reaction, and includes, for example, toluene, xylene.

The reaction temperature may be generally from room temperature to the boiling point of the solvent, preferably from 80° C. to the boiling point of the solvent.

The reaction time may be generally from 1 to 80 hours, preferably from 5 to 24 hours.

Thus obtained, the compound (I-6) of the invention may be isolated in any known isolation and purification method of, for example, concentration, concentration under reduced pressure, crystallization, solvent extraction, reprecipitation or chromatography.

The piperazine compound of the invention may exist as its pharmaceutically acceptable salt; and the salt may be produced according to an ordinary method, using a compound of formula (I) or a compound of (Ia), (I-10), (I-1), (I-2), (I-3), (I-4), (I-5) or (I-6) falling within the scope of formula (I).

The acid-addition salt includes, for example, hydrohalides such as hydrochloride, hydrofluoride, hydrobromide, hydroiodide; inorganic acid salts such as nitrate, perchlorate, sulfate, phosphate, carbonate; lower alkylsulfonates such as methanesulfonate, trifluoromethanesulfonate, ethanesulfonate; arylsulfonates such as benzenesulfonate, p-toluenesulfonate; organic acid salts such as fumarate, succinate, citrate, tartrate, oxalate, maleate; acid addition salts with an organic acid such as an amino acid, e.g., glutamate, aspartate.

In case where the compound of the invention has an acid group in the molecule, for example, when the compound has a carboxyl group, then the compound may be processed with a base to convert it into the corresponding pharmaceutically acceptable salt. The base addition salt includes, for example, alkali metal salts with sodium, potassium, etc.; alkaline earth metal salts with calcium, magnesium, etc.; ammonium salts; salts with an organic base such as guanidine, triethylamine, dicyclohexylamine, etc.

The compound of the invention may also exist as a hydrate or solvate of the free compound or its salt.

On the contrary, salts or esters may be converted into free compounds in an ordinary manner.

Depending on the substituent therein, the compound of the invention may include stereoisomers or tautomeric isomers such as optical isomers, diastereomeric isomers and geometric isomers. Needless-to-say, these isomers are all within the scope of the compound of the invention. Further needless-to-say, mixtures of these isomers are also within the scope of the compound of the invention.

The compound of the invention may be used as its radio-labeled compound by converting the aromatic hydrogen in the compound into tritium, the methyl group therein into $^{3}H_3C$, $^{14}CH_3$ or $^{11}CH_3$, the fluorine atom therein into $^{18}F$, or the carbon atom of the carbonyl group therein into $^{11}C$ or the like isotope.

The compound of the invention has an mGluR1 inhibitory effect. The "mGluR1 inhibitory effect" as referred to herein is meant to indicate any one having a function of inhibiting mGluR1, and it includes, for example, those having an mGluR1 antagonistic effect, and those having a non-competitive, mGluR1 receptor antagonistic effect.

The compound of formula (I) may be administered orally or parenterally. Formulated into a pharmaceutical preparation suitable to such administration, the invention provides a remedy and/or a preventive comprising the compound, for brain disorders such as convulsion, acute pain, inflammatory pain, chronic pain, cerebral infraction or transient cerebral ischemic attack, mental dysfunctions such as schizophrenia, and diseases such as anxiety, drug addiction, Parkinson's disease or gastrointestinal disorders.

In clinical use of the compound of the invention, pharmaceutically acceptable additives may be added to the compound in accordance with its administration mode, thereby formulated into various pharmaceutical preparations, and the preparation may be administered. Various additives known in the filed of pharmaceutics, including, for example, gelatin, lactose, white sugar, titanium oxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic anhydride, talc, vegetable oil, benzyl alcohol, gum arabic, propylene glycol, polyalkylene glycol, cyclodextrin, hydroxypropylcyclodextrin.

Regarding their form, the preparations that are formulated along with these additives may take any form of, for example, solid preparations such as tablets, capsules, granules, powders or suppositories; or liquid preparations such as syrups, elixirs or injections. These may be formulated in any ordinary method known in the field of pharmaceutics. The liquid preparations may be prepared through dissolution or suspension in water or in any other suitable medium just before use. Especially for injections, the ingredients may be dissolved or suspended in physiological saline or sucrose solution, and if desired, buffer and preservative may be added thereto.

These preparations may contain the compound of the invention in a ratio of from 1.0 to 100% by weight, preferably from 1.0 to 60% by weight of the overall amount of the preparation. The preparations may contain any other therapeutically effective compound.

In its use, the compound of the invention may be combined with any other agent effective for treatment of metabolic disorders and/or dietary disorders. The individual ingredients to be combined may be administered at different times or at the same time during treatment, either as one preparation or as divided different preparations. Accordingly, it should be so interpreted that the invention encompasses any and every administration at the same time or at different times, and the administration as referred to in the invention should be so interpreted.

The compound of the invention may be combined with a drug effective for brain disorders such as convulsion, acute pain, inflammatory pain, chronic pain, cerebral infraction or transient cerebral ischemic attack, mental dysfunctions such as schizophrenia, and also anxiety, drug addiction, Parkinson's disease or gastrointestinal disorders (the drug may be hereinafter referred to as "co-drug"). The drugs may be administered at the same time or at different times or successively in order in prevention or treatment of the above-mentioned disorders. When the compound of the invention is used simultaneously with one or more co-drugs, then it may be in a pharmaceutical composition for one-dose administration. However, in combination therapy, the composition containing the compound of the invention and the co-drug may be administered to subjects simultaneously, or separately or successively. The composition and the co-drug may be packed separately. They may be administered at different times.

The dose of the co-drug may depend on the clinical use thereof, and may be suitably determined in accordance with the administration subject, the administration route, the diseases and the combination. The form of the co-drug for administration is not specifically defined, and it may be combined with the compound of the invention when they are administered. The administration mode includes, for example, the following: (1) The compound of the invention is combined with a co-drug to give a single preparation for single administration; (2) the compound of the invention and a co-drug are separately formulated into different two preparations, and the two preparations are simultaneously administered in one administration route; (3) the compound of the invention and a co-drug are separately formulated into different two preparations, and they are administered at different times in one and the same administration route; (4) the compound of the invention and a co-drug are separately formulated into different two preparations, and they are administered at the same time in two different administration routes;

(5) the compound of the invention and a co-drug are separately formulated into different two preparations, and they are administered at different times in different administration routes (for example, the compound of the invention and a co-drug are administered in that order, or in an order contrary to this). The blend ratio of the compound of the invention and the co-drug may be suitably determined depending on the administration subject, the administration route, and the disease for the administration.

In case where the compound of the invention is used, for example, in the field of clinics, the dose and the administration frequency thereof will vary, depending on the sex, the age, the body weight and the condition of the cases to which it is administered and on the type and the scope of the intended treatment. In oral administration, in general, the dose may be from 0.01 to 100 mg/kg-adult/day, preferably from 0.03 to 1 mg/kg-adult/day, and it may be administered all at a time or may be administered in a few times as divided into a few portions. In parenteral administration, its dose may be from 0.001 to 10 mg/kg-adult/day, preferably from 0.001 to 0.1 mg/kg-adult/day, and it may be administered all at a time or may be administered in a few times as divided into a few portions.

EXAMPLES

The invention is described more concretely with reference to the following Formulation Examples, Examples and Reference Examples, which, however, are not intended to restrict the scope of the invention.

Formulation Example 1

10 parts of the compound of Example 1, 15 parts of heavy magnesium oxide and 75 parts of lactose were uniformly mixed to prepare a powdery or granular preparation having a particle size of at most 350 μm. The preparation was encapsulated to give capsules.

Formulation Example 2

45 parts of the compound of Example 1, 15 parts of starch, 16 parts of lactose, 21 parts of crystalline cellulose, 3 parts of polyvinyl alcohol and 30 parts of distilled water were uniformly mixed, then ground, granulated and dried, and then sieved to give a granular preparation having a particle diameter of from 1410 to 177 μm.

Formulation Example 3

A granular preparation was prepared in the same manner as in Formulation Example 2. 96 parts of the granular preparation was mixed with 3 parts of calcium stearate, and shaped under compression into tablets having a diameter of 10 mm.

Formulation Example 4

90 parts of the granular preparation obtained according to the method of Formulation Example 2 was mixed with 10 parts of crystalline cellulose and 3 parts of calcium stearate, and shaped under compression into tablets having a diameter of 8 mm. These were coated with a mixed suspension of syrup gelatin and precipitated calcium carbonate to give sugar-coated tablets.

In silica gel column chromatography in Examples, used was Wako Pure Chemicals' Wakogel™ C-300 or Biotage's KP-Sil™ silica prepacked column. In partitioning thin-layer chromatography, used was Merck's Kieselgel™ 60F$_{254}$, Art. 5744. In basic silica gel column chromatography, used was Fuji Silysia's Chromatorex™ NH (100-250 mesh or 200-350 mesh).

In $^1$H-NMR, used was Varian's Gemini (200 MHz, 300 MHz), Mercury (400 MHz) or Inova (400 MHz), using tetramethylsilane as a standard substance. In mass spectrometry, used was Waters' Micromass ZQ according to an electrospray ionization (ESI) method or an atmospheric chemical ionization (APCI) method.

The meanings of the abbreviations in the following Examples are shown below.
i-Bu: isobutyl group
n-Bu: n-butyl group
t-Bu: t-butyl group
Boc: tert-butoxycarbonyl group
Me: methyl group
Et: ethyl group
Ph: phenyl group
i-Pr: isopropyl group
n-Pr: n-propyl group
CDCl$_3$: heavy chloroform
CD$_3$OD: heavy methanol
DMSO-d$_6$: heavy dimethyl sulfoxide The meanings of the abbreviations in magnetic nuclear resonance spectrometry are shown below.
s: singlet
d: doublet
dd: double-doublet
dt: double-triplet
ddd: double-double-doublet
Sept: septet
t: triplet
m: multiplet
br: broad
brs: broad singlet
q: quartet
J: coupling constant
Hz: hertz Example 1

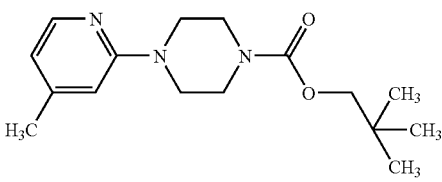

2,2-Dimethylpropyl
4-(4-methylpyridin-2-yl)-1-piperazinecarboxylate

2-Fluoro-4-methylpyridine (645 mg) and piperazine (1.77 g) were dissolved in dimethyl sulfoxide (6 mL), stirred at 100° C. for 14 hours, and then the reaction liquid was diluted with ethyl acetate, washed with water and then with saturated saline water, and dried with anhydrous sodium sulfate. The solvent was evaporated away, and the resulting residue was dissolved in pyridine (3 mL), then neopentyl chloroformate (0.144 mL) was added thereto, stirred at room temperature for 1 hour, and the reaction liquid was diluted with ethyl acetate, washed with 1 N hydrochloric acid, aqueous saturated sodium hydrogen carbonate solution and saturated saline water, and dried with anhydrous sodium sulfate. The solvent was evaporated away, and the resulting residue was isolated and purified through thin-layer silica gel column chromatography (ethyl acetate/hexane=7/3) to obtain 118 mg of the entitled compound as a colorless oil.

¹HNMR (300 MHz, CDCl₃, δ ppm): 0.96 (9H, s), 2.27 (3H, s), 3.52-3.963 (8H, m), 3.82 (2H, s), 6.48 (1H, s), 6.51 (1H, d, J=5.0 Hz), 8.06 (1H, d, J=5.0 Hz)

ESI-MS (m/e): 292.2 [M+H]⁺

Example 2

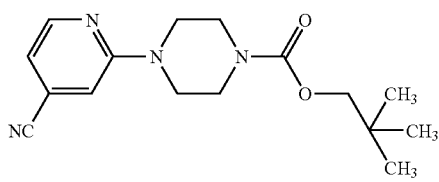

2,2-Dimethylpropyl 4-(4-cyanopyridin-2-yl)-1-piperazinecarboxylate

The entitled compound was obtained as a colorless solid according to the same method as in Example 1 but using 2-chloro-4-cyanopyridine in place of 2-fluoro-4-methylpyridine.

¹HNMR (300 MHz, CDCl₃, δ ppm): 0.97 (9H, s), 3.62 (8H, s), 3.83 (2H, s), 6.80 (1H, d, J=5.0 Hz), 6.81 (1H, s), 8.29 (1H, d, J=5.0 Hz)

ESI-MS (m/e): 303.3 [M+H]+

Example 3

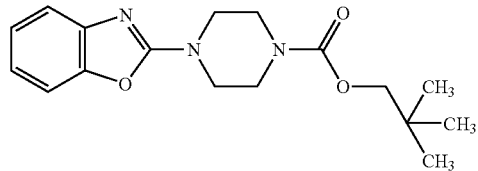

2,2-Dimethylpropyl 4-(benzoxazol-2-yl)-1-piperazinecarboxylate

The entitled compound was obtained as a colorless solid according to the same method as in Example 1 but using 2-chlorobenzoxazole in place of 2-fluoro-4-methylpyridine.

¹HNMR (300 MHz, CDCl₃, δ ppm): 0.97 (9H, s), 3.63-3.72 (8H, m), 3.84 (2H, s), 7.02-7.07 (1H, m), 7.16-7.21 (1H, m), 7.27 (1H, d, J=7.2 Hz), 7.37 (1H, d, J=7.9 Hz)

ESI-MS (m/e): 318.3 [M+H]+

Example 4

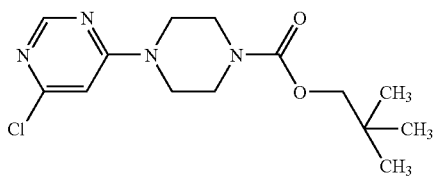

2,2-Dimethylpropyl 4-(6-chloropyrimidin-4-yl)-1-piperazinecarboxylate

The entitled compound was obtained as a colorless solid according to the same method as in Example 1 but using 4,6-dichloropyrimidine in place of 2-fluoro-4-methylpyridine.

¹HNMR (300 MHz, CDCl₃, δ ppm): 0.96 (9H, s), 3.59-3.69 (8H, m), 3.83 (2H, s), 6.51 (1H, s), 8.40 (1H, s)

ESI-MS (m/e): 313.3 [M+H]+

Example 5

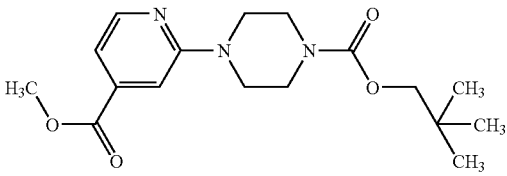

2,2-Dimethylpropyl 4-[4-(methoxycarbonyl)pyridin-2-yl]-1-piperazinecarboxylate

The entitled compound was obtained as a colorless oil according to the same method as in Example 1 but using 2-chloroisonicotinic acid in place of 2-fluoro-4-methylpyridine.

¹HNMR (300 MHz, CDCl₃, δ ppm): 0.97 (9H, s), 3.53 (8H, s), 3.83 (2H, s), 3.93 (3H, s), 7.16 (1H, d, J=5.2 Hz), 7.24 (1H, s), 8.30 (1H, d, J=5.2 Hz)

ESI-MS (m/e): 336.2 [M+H]+

Example 6

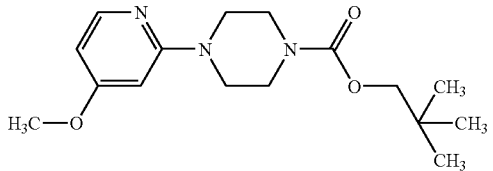

2,2-Dimethylpropyl 4-(4-methoxypyridin-2-yl)-1-piperazinecarboxylate

The entitled compound was obtained as a colorless oil according to the same method as in Example 1 but using 2-chloro-4-methoxypyridine in place of 2-fluoro-4-methylpyridine.

¹HNMR (300 MHz, CDCl₃, δ ppm): 0.96 (9H, s), 3.51-3.55 (4H, m), 3.60-3.63 (4H, m), 3.82 (3H, s), 6.11 (1H, d, J=2.0 Hz), 6.29 (1H, dd, J=2.0 and 5.8 Hz), 8.04 (1H, d, J=5.8 Hz)

ESI-MS (m/e): 308.1 [M+H]+

Example 7

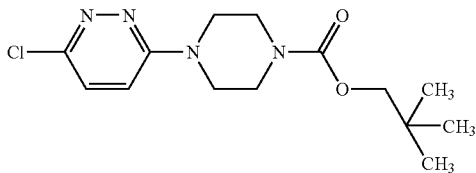

2,2-Dimethylpropyl 4-(6-chloropyridazin-3-yl)-1-piperazinecarboxylate

The entitled compound was obtained as a colorless solid according to the same method as in Example 1 but using 3,6-dichloropyridazine in place of 2-fluoro-4-methylpyridine.

$^1$HNMR (300 MHz, CDCl$_3$, δ ppm): 0.96 (9H, s), 3.65 (8H, s), 3.83 (2H, s), 6.91 (1H, d, J=9.6 Hz), 7.25 (1H, d, J=9.6 Hz)
ESI-MS (m/e): 313.3 [M+H]+

Example 8

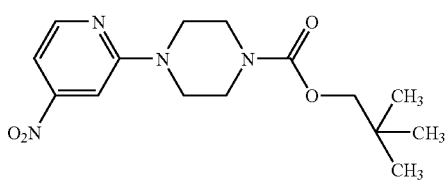

2,2-Dimethylpropyl 4-(4-nitropyridin-2-yl)-1-piperazinecarboxylate

The entitled compound was obtained as a yellow solid according to the same method as in Example 1 but using 2-chloro-4-nitropyridine in place of 2-fluoro-4-methylpyridine.

$^1$HNMR (300 MHz, CDCl$_3$, δ ppm): 0.97 (9H, s), 3.62-3.71 (8H, m), 3.84 (2H, s), 7.29 (1H, d, J=5.3 Hz), 7.32 (1H, s), 8.39 (1H, d, J=5.3 Hz)
ESI-MS (m/e): 323.3 [M+H]+

Example 9

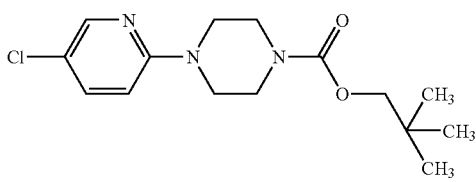

2,2-Dimethylpropyl 4-(5-chloropyridin-2-yl)-1-piperazinecarboxylate

The entitled compound was obtained as a colorless oil according to the same method as in Example 1 but using 2,5-dichloropyridine in place of 2-fluoro-4-methylpyridine.

$^1$HNMR (300 MHz, CDCl$_3$, δ ppm): 0.96 (9H, s), 3.51-3.54 (4H, m), 3.60-3.63 (4H, m), 3.82 (2H, s), 6.59 (1H, d, J=8.9 Hz), 7.44 (1H, dd, J=2.6 and 8.9 Hz), 8.12 (1H, d, J=2.6 Hz)
ESI-MS (m/e): 312.1 [M+H]+

Example 10

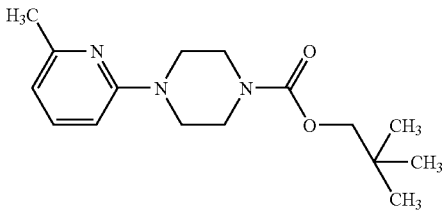

2,2-Dimethylpropyl 4-(6-methylpyridin-2-yl)-1-piperazinecarboxylate

The entitled compound was obtained as a colorless oil according to the same method as in Example 1 but using 2-chloro-6-methylpyridine in place of 2-fluoro-4-methylpyridine.

$^1$HNMR (300 MHz, CDCl$_3$, δ ppm): 0.96 (9H, s), 2.40 (3H, s), 3.49-3.63 (8H, m), 3.82 (2H, s), 6.44 (1H, d, J=8.5 Hz), 6.52 (1H, d, J=7.4 Hz), 7.37-7.42 (1H, m)
ESI-MS (m/e): 292.1 [M+H]+

Example 11

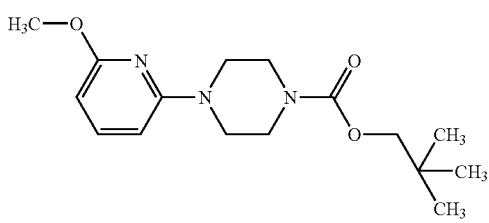

2,2-Dimethylpropyl 4-(6-methoxypyridin-2-yl)-1-piperazinecarboxylate

The entitled compound was obtained as a colorless oil according to the same method as in Example 1 but using 2-chloro-6-methoxypyridine in place of 2-fluoro-4-methylpyridine.

$^1$HNMR (300 MHz, CDCl$_3$, δ ppm): 0.96 (9H, s), 3.52-3.63 (8H, m), 3.82 (2H, s), 3.87 (3H, s), 6.10-6.18 (2H, m), 7.39-7.44 (1H, m)
ESI-MS (m/e): 308.2 [M+H]+

Example 12

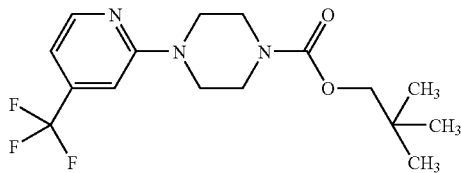

2,2-Dimethylpropyl 4-[4-(trifluoromethyl)pyridin-2-yl]-1-piperazinecarboxylate

The entitled compound was obtained as a colorless solid according to the same method as in Example 1 but using 2-chloro-4-trifluoromethylpyridine in place of 2-fluoro-4-methylpyridine.

$^1$HNMR (300 MHz, CDCl$_3$, δ ppm): 0.97 (9H, s), 3.63 (8H, s), 3.83 (2H, s), 6.80 (1H, s), 6.81 (1H, d, J=5.0 Hz), 8.31 (1H, d, J=5.0 Hz)

ESI-MS (m/e): 346.3 [M+H]+

Example 13

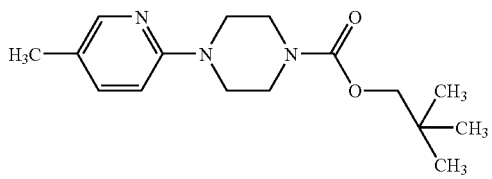

2,2-Dimethylpropyl 4-(5-methylpyridin-2-yl)-1-piperazinecarboxylate

The entitled compound was obtained as a colorless oil according to the same method as in Example 1 but using 2-chloro-5-methylpyridine in place of 2-fluoro-4-methylpyridine.

$^1$HNMR (300 MHz, CDCl$_3$, δ ppm): 0.96 (9H, s), 2.20 (3H, s), 3.46-3.50 (4H, m), 3.60-3.63 (4H, m), 3.82 (2H, s), 6.60 (1H, d, J=8.6 Hz), 7.34 (1H, dd, J=2.3 and 8.6 Hz), 8.03 (1H, s)

ESI-MS (m/e): 292.1 [M+H]+

Example 14

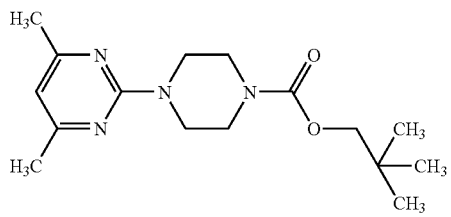

2,2-Dimethylpropyl 4-(4,6-dimethylpyrimidin-2-yl)-1-piperazinecarboxylate

The entitled compound was obtained as a colorless solid according to the same method as in Example 1 but using 2-chloro-4,6-dimethylpyrimidine in place of 2-fluoro-4-methylpyridine.

$^1$HNMR (300 MHz, CDCl$_3$, δ ppm): 0.96 (9H, s), 2.29 (6H, s), 3.53-3.56 (4H, m), 3.82 (2H, s), 3.83-3.89 (4H, m), 6.30 (1H, s)

ESI-MS (m/e): 307.2 [M+H]+

Example 15

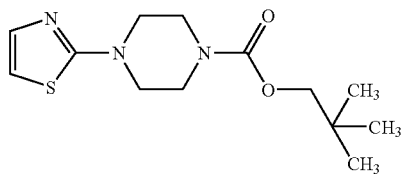

2,2-Dimethylpropyl 4-(thiazol-2-yl)-1-piperazinecarboxylate

The entitled compound was obtained as a colorless solid according to the same method as in Example 1 but using 2-bromothiazole in place of 2-fluoro-4-methylpyridine.

$^1$HNMR (300 MHz, CDCl$_3$, δ ppm): 0.96 (9H, s), 3.48-3.52 (4H, m), 3.62-3.66 (4H, m), 3.82 (2H, s), 6.61 (1H, d, J=3.6 Hz), 7.21 (1H, d, J=3.6 Hz)

ESI-MS (m/e): 284.1 [M+H]+

Example 16

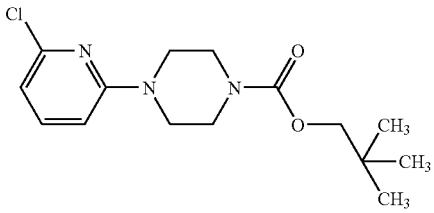

2,2-Dimethylpropyl 4-(6-chloropyridin-2-yl)-1-piperazinecarboxylate

The entitled compound was obtained as a colorless solid according to the same method as in Example 1 but using 2,6-dichloropyridine in place of 2-fluoro-4-methylpyridine.

$^1$HNMR (300 MHz, CDCl$_3$, δ ppm): 0.96 (9H, s), 3.58-3.63 (8H, m), 3.82 (2H, s), 6.50 (1H, d, J=8.4 Hz), 6.63 (1H, d, J=7.6 Hz), 7.39-7.44 (1H, m)

ESI-MS (m/e): 312.3 [M+H]+

Example 17

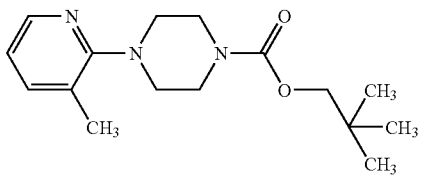

2,2-Dimethylpropyl
4-(3-methylpyridin-2-yl)-1-piperazinecarboxylate

The entitled compound was obtained as a colorless oil according to the same method as in Example 1 but using 2-chloro-3-methylpyridine in place of 2-fluoro-4-methylpyridine.

$^1$HNMR (300 MHz, CDCl$_3$, δ ppm): 0.96 (9H, s), 2.29 (3H, s), 3.10-3.14 (4H, m), 3.63-3.66 (4H, m), 3.82 (2H, s), 6.86-6.80 (1H, m), 7.42 (1H, d, J=7.3 Hz), 8.16 (1H, d, J=5.0 Hz)

ESI-MS (m/e): 292.1 [M+H]+

Example 18

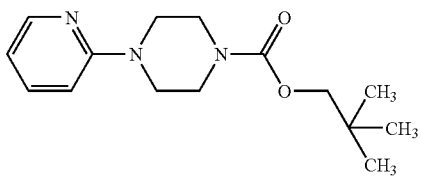

2,2-Dimethylpropyl
4-(pyridin-2-yl)-1-piperazinecarboxylate 1-(2-Pyridyl)piperazine (106 m) was dissolved in chloroform (2 mL), and neopentyl chloroformate (0.10 mL) and triethylamine (0.135 mL) were added thereto and stirred at room temperature for 5 hours, and the reaction liquid was diluted with ethyl acetate, washed with water and saturated saline water and dried with anhydrous sodium sulfate. The solvent was evaporated away, and the resulting residue was isolated and purified through thin-layer silica gel chromatography (chloroform/methanol=19/1) to obtain 177 mg of the entitled compound as a colorless solid.

$^1$HNMR (200 MHz, CDCl$_3$, δ ppm): 0.96 (9H, s), 3.52-3.66 (8H, m), 3.82 (2H, s), 6.63-6.69 (2H, m), 7.46-7.55 (1H, m), 8.18-8.22 (1H, m)

ESI-MS (m/e): 278.1 [M+H]+

Example 19

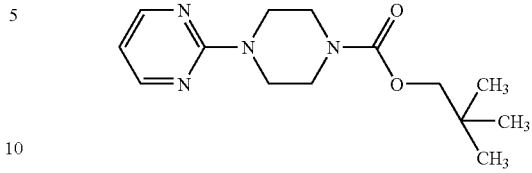

2,2-Dimethylpropyl
4-(pyrimidin-2-yl)-1-piperazinecarboxylate

The entitled compound was obtained as a colorless solid according to the same method as in Example 18 but using 1-(2-pyrimidyl)piperazine in place of 1-(2-pyridyl)piperazine.

$^1$HNMR (300 MHz, CDCl$_3$, δ ppm): 0.97 (9H, s), 3.55-3.59 (4H, m), 3.82-3.85 (6H, m), 6.51-6.54 (2H, m), 8.32 (1H, d, J=4.7 Hz)

ESI-MS (m/e): 279.1 [M+H]+

Example 20

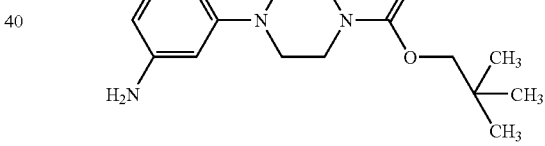

2,2-Dimethylpropyl
4-(4-aminopyridin-2-yl)-1-piperazinecarboxylate 2,2-Dimethylpropyl 4-(4-nitropyridin-2-yl)-1-piperazinecarboxylate (482 mg) obtained in Example 8 was dissolved in methanol (10 mL), and a catalytic amount of palladium hydroxide-carbon was added thereto, stirred in a hydrogen atmosphere at room temperature for 2 hours, and the reaction liquid was filtered. The filtrate was evaporated, and the resulting residue was isolated and purified through thin-layer silica gel chromatography (chloroform/methanol=19/1) to obtain 48 mg of the entitled compound as an oil.

$^1$HNMR (300 MHz, CDCl$_3$, δ ppm): 0.96 (9H, s), 3.49-3.62 (8H, m), 3.81 (2H, s), 4.04 (2H, br s), 5.87 (1H, d, J=1.8 Hz), 6.04 (1H, dd, J=1.8 and 5.8 Hz), 7.88 (1H, d, J=5.8 Hz)

ESI-MS (m/e): 293.2 [M+H]+

Example 21

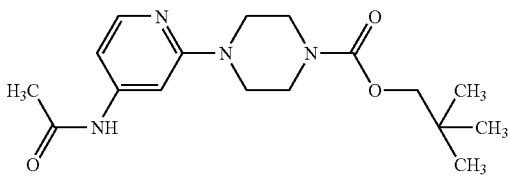

2,2-Dimethylpropyl 4-[4-(acetylamino)pyridin-2-yl]-1-piperazinecarboxylate 2,2-Dimethylpropyl 4-(4-aminopyridin-2-yl)-1-piperazinecarboxylate (105 mg) obtained in Example 20 was dissolved in pyridine (2 mL), acetic anhydride (0.1 mL) was added thereto, and stirred at room temperature for 3 hours, and the reaction liquid was diluted with chloroform, washed with saturated sodium hydrogencarbonate and saturated saline water, and dried with anhydrous sodium sulfate. The solvent was evaporated away, and the resulting residue was isolated and purified through thin-layer silica gel chromatography (chloroform/methanol=19/1) to obtain 52 mg of the entitled compound as a colorless oil.

$^1$HNMR (300 MHz, CDCl$_3$, δ ppm): 0.96 (9H, s), 2.19 (3H, s), 3.55-3.61 (8H, m), 3.82 (2H, s), 6.51-6.54 (1H, m), 7.23 (1H, s), 7.35 (1H, br s), 8.06 (1H, d, J=5.5 Hz)

ESI-MS (m/e): 335.2 [M+H]+

Example 22

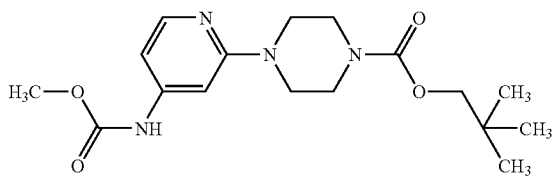

2,2-Dimethylpropyl 4-{4-[(methoxycarbonyl)amino]pyridin-2-yl}-1-piperazinecarboxylate The entitled compound was obtained as a colorless oil according to the same method as in Example 21 but using methyl chloroformate in place of acetic anhydride.

$^1$HNMR (300 MHz, CDCl$_3$, δ ppm): 0.96 (9H, s), 3.54-3.61 (8H, m), 3.79 (3H, s), 3.82 (2H, s), 6.46-6.49 (1H, m), 6.68 (1H, br s), 7.00 (1H, s), 8.04 (1H, d, J=5.6 Hz)

ESI-MS (m/e): 351.2 [M+H]+

Example 23

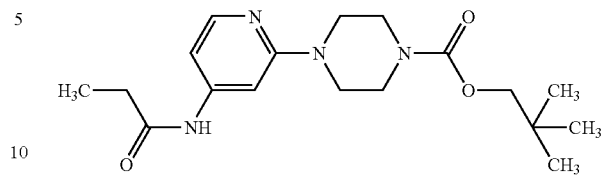

2,2-Dimethylpropyl 4-[4-(propionylamino)pyridin-2-yl]-1-piperazinecarboxylate

The entitled compound was obtained as a colorless oil according to the same method as in Example 21 but using propionyl chloride in place of acetic anhydride.

$^1$HNMR (300 MHz, CDCl$_3$, δ ppm): 0.96 (9H, s), 1.24 (3H, t, J=7.5 Hz), 2.41 (2H, q, J=7.5 Hz), 3.54-3.61 (8H, m), 3.82 (2H, s), 6.49 (1H, d, J=5.6 Hz), 7.22 (1H, br s), 7.31 (1H, s), 8.06 (1H, d, J=5.6 Hz)

ESI-MS (m/e): 349.2 [M+H]+

Example 24

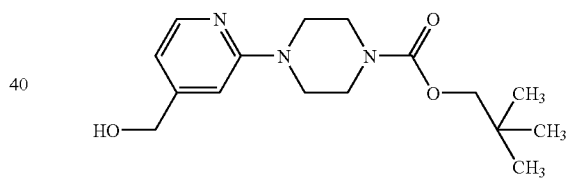

2,2-Dimethylpropyl 4-[4-(hydroxymethyl)pyridin-2-yl]-1-piperazinecarboxylate 2,2-Dimethylpropyl 4-[4-(methoxycarbonyl)pyridin-2-yl]-1-piperazinecarboxylate (365 mg) obtained in Example 5 was dissolved in tetrahydrofuran (5 mL), and lithium tetrahydroborate (30 mg) was added thereto, stirred at room temperature for 30 minutes, and then 1 N sodium hydroxide was added thereto and stirred at room temperature for 30 minutes. The reaction liquid was diluted with ethyl acetate, washed with water and saturated saline water, and dried with anhydrous sodium sulfate. The solvent was evaporated away, and the resulting residue was isolated and purified through thin-layer silica gel chromatography (hexane/ethyl acetate=1/1) to obtain 11 mg of the entitled compound as a colorless oil.

$^1$HNMR (300 MHz, CDCl$_3$, δ ppm): 0.96 (9H, s), 3.56-3.63 (8H, m), 3.82 (2H, s), 4.66 (2H, s), 6.62 (1H, d, J=5.0 Hz), 6.69 (1H, s), 8.15 (1H, d, J=5.0 Hz)

ESI-MS (m/e): 308.2 [M+H]+

Example 25

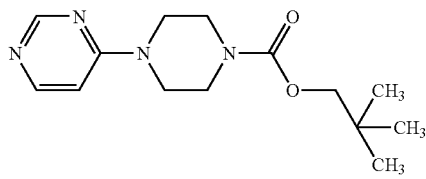

2,2-Dimethylpropyl 4-(pyrimidin-4-yl)-1-piperazinecarboxylate 2,2-Dimethylpropyl 4-(6-chloropyrimidin-4-yl)-1-piperazinecarboxylate (68 mg) obtained in Example 4 was dissolved in methanol (3 mL), and 0.5 ml of aqueous ammonia and a catalytic amount of palladium hydroxide-carbon were added thereto, and stirred in a hydrogen atmosphere at room temperature for 2 hours, and the reaction liquid was filtered. The filtrate was evaporated, and the resulting residue was diluted with ethyl acetate, washed with water and saturated saline water, and dried with anhydrous sodium sulfate. The solvent was evaporated away and the resulting residue was isolated and purified through thin-layer silica gel chromatography (hexane/ethyl acetate=1/1) to obtain 20 mg of the entitled compound as an oil.

$^1$HNMR (300 MHz, CDCl$_3$, δ ppm): 0.96 (9H, s), 3.59-3.69 (8H, m), 3.83 (2H, s), 6.51 (1H, d, J=6.3 Hz), 8.24 (1H, d, J=6.3 Hz), 8.62 (1H, s)

ESI-MS (m/e): 279.1 [M+H]+ and potassium carbonate (3.11 g) were added thereto, heated under reflux for 2 hours, and the solvent was evaporated away, the resulting residue was diluted with ethyl acetate, washed with water and saturated saline water, and dried with anhydrous sodium sulfate. The solvent was evaporated away to obtain 2.04 g of the entitled compound.

2) Production of 2,2-dimethylpropyl 4-(4-[5-[(1S)-1-hydroxyethyl]-1,2,4-oxadiazol-3-yl]pyridin-2-yl)-1-piperazinecarboxylate 2,2-Dimethylpropyl 4-{4-[amino(hydroxyimino)methyl]pyridin-2-yl}-1-piperazinecarboxylate (657 mg) was dissolved in tetrahydrofuran (10 mL), oily sodium hydride (82.6 mg) was added thereto and stirred at 60° C. for 15 minutes, then methyl (S)-lactate (0.333 mL) was added thereto and heated under reflux for 1 hour. Aqueous saturated ammonium chloride solution was added to the reaction liquid, and extracted with ethyl acetate. The organic layer was washed with saturated saline water, and dried with anhydrous sodium sulfate. The solvent was evaporated away, and the resulting residue was isolated and purified through silica gel column chromatography (hexane/ethyl acetate=1/1) to obtain 402 mg of the entitled compound as a colorless solid.

$^1$HNMR (300 MHz, CDCl$_3$, δ ppm): 0.97 (9H, s), 1.73 (3H, d, J=6.7 Hz), 3.65 (8H, s), 3.83 (2H, s), 5.13-5.22 (1H, m), 7.27 (1H, d, J=5.0 Hz), 7.32 (1H, s), 8.32 (1H, d, J=5.0 Hz)

APCI-MS (m/e): 390.1 [M+H]+

Example 26

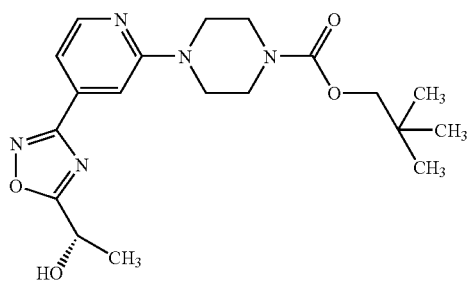

2,2-Dimethylpropyl 4-(4-{5-[(1S)-1-hydroxyethyl]-1,2,4-oxadiazol-3-yl}pyridin-2-yl)-1-piperazinecarboxylate 1) Production of 2,2-dimethylpropyl 4-{4-[amino(hydroxyimino)methyl]pyridin-2-yl}-1-piperazinecarboxylate 2,2-Dimethylpropyl 4-(4-cyanopyridin-2-yl)piperazine-1-carboxylate (1.67 g) obtained in Example 2 was dissolved in ethanol (10 mL), and hydroxyamine hydrochloride (1.17 g)

Example 27

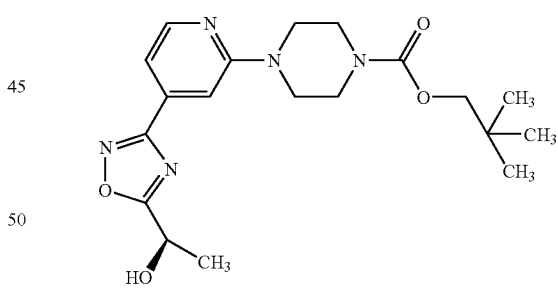

2,2-Dimethylpropyl 4-(4-{5-[(1R)-1-hydroxyethyl]-1,2,4-oxadiazol-3-yl}pyridin-2-yl)-1-piperazinecarboxylate The entitled compound was obtained as a colorless solid according to the same method as in Example 26 but using methyl (R)-lactate in place of methyl (S)-lactate.

$^1$HNMR (300 MHz, CDCl$_3$, δ ppm): 0.97 (9H, s), 1.73 (3H, d, J=6.8 Hz), 3.65 (8H, s), 3.83 (2H, s), 5.13-5.22 (1H, m), 7.27 (1H, d, J=5.2 Hz), 7.31 (1H, s), 8.32 (1H, d, J=5.2 Hz)

APCI-MS (m/e): 390.1 [M+H]+

Example 28

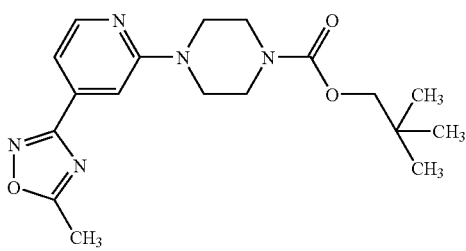

2,2-Dimethylpropyl 4-[4-(5-methyl-1,2,4-oxadiazol-3-yl)pyridin-2-yl]-1-piperazinecarboxylate Acetic anhydride (3 mL) was added to 2,2-dimethylpropyl 4-{4-[amino(hydroxyimino)methyl]pyridin-2-yl}piperazine-1-carboxylate (215 mg) obtained in Example 26-1), and heated under reflux for 2 hours, then the excess acetic anhydride was evaporated away, the residue was diluted with ethyl acetate, washed with aqueous saturated sodium hydrogencarbonate solution and saturated saline water, and dried with anhydrous sodium sulfate. The solvent was evaporated away, and the resulting residue was isolated and purified through silica gel column chromatography (hexane/ethyl acetate=7/3) to obtain 36 mg of the entitled compound as a colorless solid.

$^1$HNMR (300 MHz, CDCl$_3$, δ ppm): 0.97 (9H, s), 2.67 (3H, s), 3.65 (8H, s), 3.83 (2H, s), 7.26 (1H, d, J=5.0 Hz), 7.30 (1H, s), 8.31 (1H, d, J=5.0 Hz)

ESI-MS (m/e): 360.2 [M+H]+

Example 29

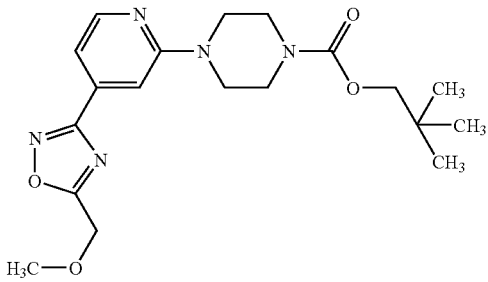

2,2-Dimethylpropyl 4-[4-(5-methoxy-1,2,4-oxadiazol-3-yl)pyridin-2-yl]-1-piperazinecarboxylate 2,2-Dimethylpropyl 4-{4-[amino(hydroxyimino)methyl]pyridin-2-yl}piperazine-1-carboxylate (84 mg) obtained in Example 26-1) was dissolved in pyridine (2 mL), and methoxyacetyl chloride (0.035 mL) was added thereto and heated under reflux for 90 minutes. The reaction liquid was diluted with ethyl acetate, washed with 1 N hydrochloric acid, aqueous saturated sodium hydrogencarbonate solution and saturated saline water, and dried with anhydrous sodium sulfate. The solvent was evaporated away, and the resulting residue was isolated and purified through silica gel column chromatography (hexane/ethyl acetate=7/3) to obtain 54 mg of the entitled compound as a colorless oil.

$^1$HNMR (300 MHz, CDCl$_3$, δ ppm): 0.97 (9H, s), 3.57 (3H, s), 3.65 (8H, s), 3.83 (2H, s), 4.77 (2H, s), 7.30 (1H, d, J=5.2 Hz), 7.34 (1H, s), 8.32 (1H, d, J=5.2 Hz)

APCI-MS (m/e): 390.1 [M+H]+

Example 30

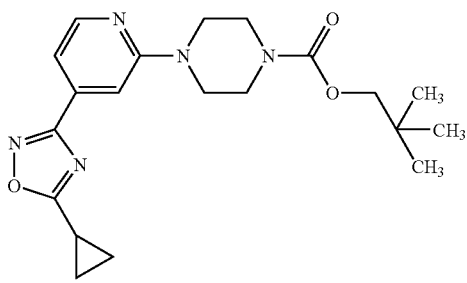

2,2-Dimethylpropyl 4-[4-(5-cyclopropyl-1,2,4-oxadiazol-3-yl)pyridin-2-yl]-1-piperazinecarboxylate The entitled compound was obtained as a colorless solid according to the same method as in Example 29 but using cyclopropanecarbonyl chloride in place of methoxyacetyl chloride.

$^1$HNMR (300 MHz, CDCl$_3$, δ ppm): 0.97 (9H, s), 1.26-1.33 (4H, m), 2.22-2.31 (1H, m), 3.64 (8H, s), 3.83 (2H, s), 7.24 (1H, d, J=5.2 Hz), 7.27 (1H, s), 8.29 (1H, d, J=5.2 Hz)

APCI-MS (m/e): 386.1 [M+H]+

Example 31

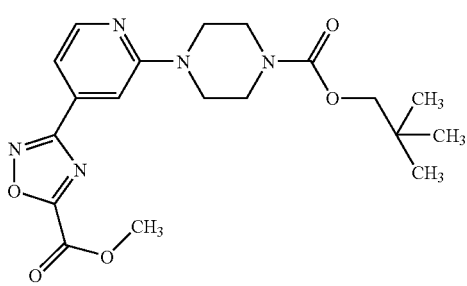

2,2-Dimethylpropyl 4-{4-[5-(methoxycarbonyl)-1,2,4-oxadiazol-3-yl]pyridin-2-yl}-1-piperazinecarboxylate The entitled compound was obtained as a colorless oil according to the same method as in Example 29 but using methyl chloroglyoxalate in place of methoxyacetyl chloride.

$^1$HNMR (300 MHz, CDCl$_3$, δ ppm): 0.97 (9H, s), 3.62-3.69 (8H, m), 3.83 (2H, s), 4.13 (3H, s), 7.32 (1H, d, J=5.1 Hz), 7.36 (1H, s), 8.34 (1H, d, J=5.1 Hz)

ESI-MS (m/e): 404.1 [M+H]+

Example 32

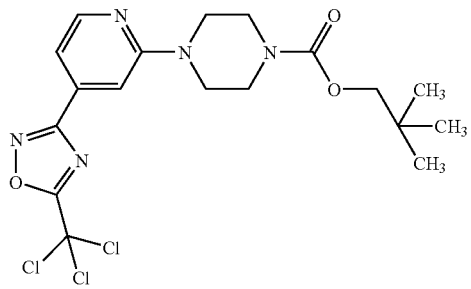

2,2-Dimethylpropyl 4-{4-[5-(trichloromethyl)-1,2,4-oxadiazol-3-yl]pyridin-2-yl}-1-piperazinecarboxylate The entitled compound was obtained as a yellow oil according to the same method as in Example 28 but using trichloroacetic anhydride in place of acetic anhydride.

$^1$HNMR (300 MHz, CDCl$_3$, δ ppm): 0.97 (9H, s), 3.63-3.70 (8H, m), 3.83 (2H, s), 7.30 (1H, d, J=5.0 Hz), 7.32 (1H, s), 8.35 (1H, d, J=5.0 Hz)

ESI-MS (m/e): 464.1 [M+H]+

Example 33

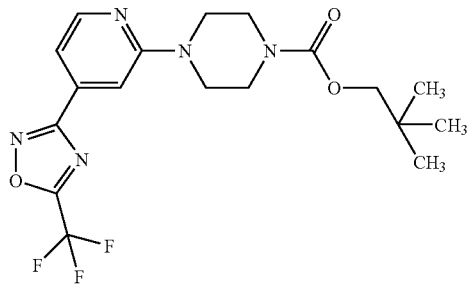

2,2-Dimethylpropyl 4-[4-[5-(trifluoromethyl)-1,2,4-oxadiazol-3-yl]pyridin-2-yl]-1-piperazinecarboxylate The entitled compound was obtained as a yellow oil according to the same method as in Example 28 but using trifluoroacetic anhydride in place of acetic anhydride.

$^1$HNMR (300 MHz, CDCl$_3$, δ ppm): 0.97 (9H, s), 3.63-3.70 (8H, m), 3.83 (2H, s), 7.29 (1H, d, J=5.2 Hz), 7.32 (1H, s), 8.36 (1H, d, J=5.2 Hz)

ESI-MS (m/e): 414.2 [M+H]+

Example 34

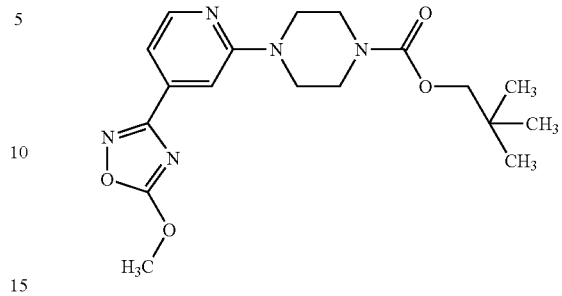

2,2-Dimethylpropyl 4-[4-(5-methoxy-1,2,4-oxadiazol-3-yl)pyridin-2-yl]-1-piperazinecarboxylate 2,2-Dimethylpropyl 4-[4-(5-trichloromethyl-1,2,4-oxadiazol-3-yl)pyridin-2-yl]-1-piperazinecarboxylate (106 mg) obtained in Example 32 was dissolved in methanol (2 mL), and oily sodium hydride (10 mg) was added thereto and stirred at room temperature for 15 minutes, and then aqueous saturated ammonium chloride solution was added to it and extracted with ethyl acetate. The organic layer was washed with saturated saline water, and dried with anhydrous sodium sulfate. The solvent was evaporated away, and the resulting residue was isolated and purified through thin-layer silica gel chromatography (hexane/ethyl acetate=1/1) to obtain 2.5 mg of the entitled compound as a colorless oil.

$^1$HNMR (300 MHz, CDCl$_3$, δ ppm): 0.97 (9H, s), 3.64 (8H, s), 3.83 (2H, s), 4.28 (3H, s), 7.21 (1H, d, J=5.2 Hz), 7.23 (1H, s), 8.30 (1H, d, J=5.2 Hz)

ESI-MS (m/e): 376.1 [M+H]+

Example 35

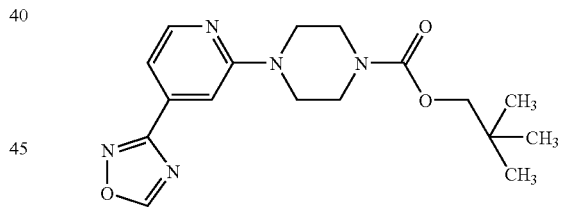

2,2-Dimethylpropyl 4-[4-(1,2,4-oxadiazol-3-yl)pyridin-2-yl]-1-piperazinecarboxylate 2,2-Dimethylpropyl 4-[4-(5-trichloromethyl-1,2,4-oxadiazol-3-yl)pyridin-2-yl]-1-piperazinecarboxylate (23.1 mg) obtained in Example 32 was dissolved in methanol (2 mL), and sodium borohydride (10 mg) was added thereto and stirred at room temperature for 10 minutes. Then, the reaction liquid was diluted with ethyl acetate, washed with water and saturated saline water, and dried with anhydrous sodium sulfate. The solvent was evaporated away, and the resulting residue was isolated and purified through thin-layer silica gel chromatography (hexane/ethyl acetate=7/3) to obtain 9.1 mg of the entitled compound as a colorless oil.

$^1$HNMR (300 MHz, CDCl$_3$, δ ppm): 0.97 (9H, s), 3.65 (8H, s), 3.83 (2H, s), 7.30-7.35 (2H, m), 8.34 (1H, d, J=4.9 Hz), 8.80 (1H, s)

ESI-MS (m/e): 346.2 [M+H]+

Example 36

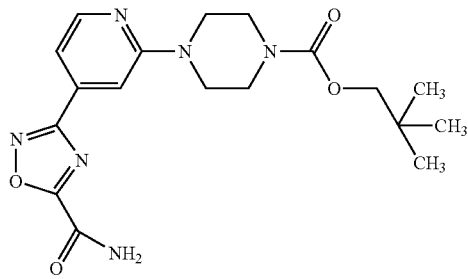

2,2-Dimethylpropyl 4-[4-(5-carbamoyl-1,2,4-oxadiazol-3-yl)pyridin-2-yl]-1-piperazinecarboxylate 2,2-Dimethylpropyl 4-{4-[5-(methoxycarbonyl)-1,2,4-oxadiazol-3-yl]pyridin-2-yl}-1-piperazinecarboxylate (86.5 mg) obtained in Example 31 was dissolved in toluene (1 mL), and aqueous ammonia (0.3 mL) was added thereto and stirred at room temperature for 4 hours. Then, the solvent was evaporated away, and the resulting residue was isolated and purified through thin-layer silica gel chromatography (chloroform/methanol=97/3) to obtain 40 mg of the entitled compound as a colorless solid.
$^1$HNMR (300 MHz, CDCl$_3$, δ ppm): 0.97 (9H, s), 3.66 (8H, s), 3.83 (2H, s), 6.28 (1H, br s), 7.03 (1H, br s), 7.29 (1H, d, J=5.0 Hz), 7.33 (1H, s), 8.35 (1H, d, J=5.0 Hz)
ESI-MS (m/e): 389.1 [M+H]+

Example 37

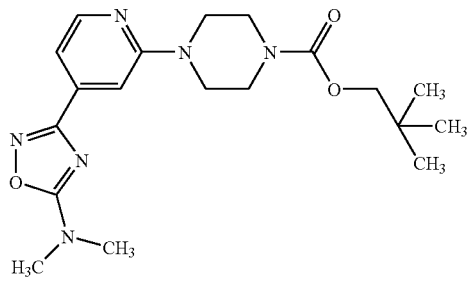

2,2-Dimethylpropyl 4-{4-[5-(dimethylamino)-1,2,4-oxadiazol-3-yl]pyridin-2-yl}-1-piperazinecarboxylate 2,2-Dimethylpropyl 4-{4-[5-(trichloromethyl)-1,2,4-oxadiazol-3-yl]pyridin-2-yl}-1-piperazinecarboxylate (133 mg) obtained in Example 32 was dissolved in ethanol (4 mL), and aqueous 50% dimethylamine solution (1 mL) was added thereto, and stirred at room temperature for 3 hours. Then, the solvent was evaporated away and the resulting residue was isolated and purified through thin-layer silica gel chromatography (hexane/ethyl acetate=1/1) to obtain 49.1 mg of the entitled compound as a colorless oil.
$^1$HNMR (300 MHz, CDCl$_3$, δ ppm): 0.96 (9H, s), 3.21 (6H, s), 3.63 (8H, s), 3.83 (2H, s), 7.20 (1H, d, J=5.1 Hz), 7.24 (1H, s), 8.27 (1H, d, J=5.1 Hz)
ESI-MS (m/e): 389.2 [M+H]+

Example 38

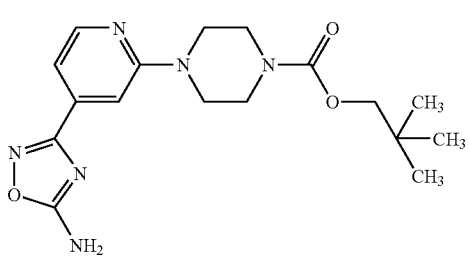

2,2-Dimethylpropyl 4-[4-(5-amino-1,2,4-oxadiazol-3-yl)pyridin-2-yl]-1-piperazinecarboxylate The entitled compound was obtained as a colorless solid according to the same method as in Example 37 but using aqueous ammonia in place of aqueous 50% dimethylamine solution.
$^1$HNMR (300 MHz, CDCl$_3$, δ ppm): 0.96 (9H, s), 3.63 (8H, s), 3.82 (2H, s), 5.40 (2H, br s), 7.17 (1H, d, J=5.2 Hz), 7.20 (1H, s), 7.28 (1H, d, J=5.2 Hz)
ESI-MS (m/e): 361.2 [M+H]+

Example 39

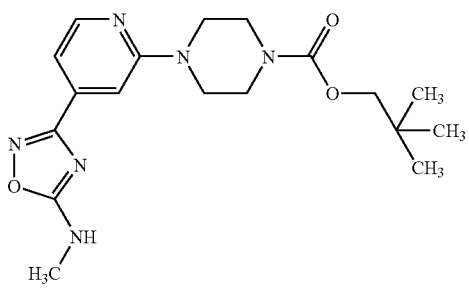

2,2-Dimethylpropyl 4-{4-[5-(methylamino)-1,2,4-oxadiazol-3-yl]pyridin-2-yl}-1-piperazinecarboxylate The entitled compound was obtained as a colorless solid according to the same method as in Example 37 but using 40% methylamine/methanol solution in place of aqueous 50% dimethylamine solution.
$^1$HNMR (300 MHz, CDCl$_3$, δ ppm): 0.97 (9H, s), 3.14 (3H, d, J=5.0 Hz), 3.63 (8H, s), 3.83 (2H, s), 7.20 (1H, d, J=5.3 Hz), 7.23 (1H, s), 8.28 (1H, d, J=5.3 Hz)
ESI-MS (m/e): 375.2 [M+H]+

Example 40

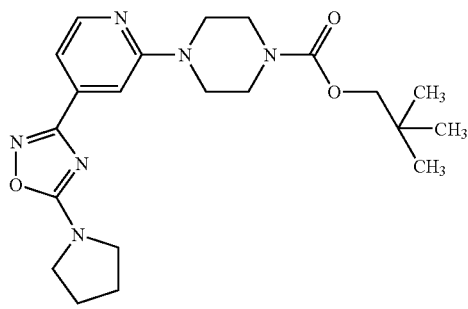

2,2-Dimethylpropyl 4-{4-[5-(pyrrolidin-1-yl)-1,2,4-oxadiazol-3-yl]pyridin-2-yl}-1-piperazinecarboxylate The entitled compound was obtained as a colorless solid according to the same method as in Example 37 but using pyrrolidine in place of aqueous 50% dimethylamine solution.

$^1$HNMR (300 MHz, CDCl$_3$, δ ppm): 0.97 (9H, s), 2.03-2.28 (4H, m), 3.62-3.66 (12H, m), 3.83 (2H, s), 7.20-7.27 (2H, m), 8.27 (1H, d, J=5.2 Hz)

ESI-MS (m/e): 415.3 [M+H]+

Example 41

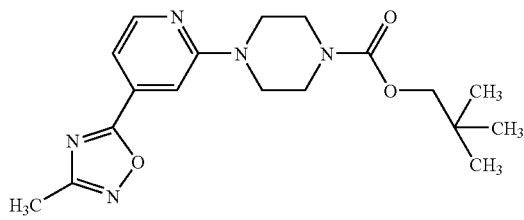

2,2-Dimethylpropyl 4-[4-(3-methyl-1,2,4-oxadiazol-5-yl)pyridin-2-yl]-1-piperazinecarboxylate 2,2-Dimethylpropyl 4-(4-cyanopyridin-2-yl)piperazine-1-carboxylate (301 mg) obtained in Example 2 was dissolved in toluene (5 mL), and nitroethane (82.6 mg), triethylamine (one drop) and phenyl isocyanate (0.238 mL) were added thereto, stirred at room temperature for 1 hour, and then heated under reflux for 2 hours. The reaction liquid was filtered, the filtrate was evaporated, and the resulting residue was isolated and purified through thin-layer silica gel chromatography (hexane/ethyl acetate=1/1) to obtain 114 mg of the entitled compound as a yellow solid.

$^1$HNMR (300 MHz, CDCl$_3$, δ ppm): 0.97 (9H, s), 2.49 (3H, s), 3.62-3.69 (8H, m), 3.83 (2H, s), 7.26 (1H, d, J=5.3 Hz), 7.30 (1H, s), 8.36 (1H, d, J=5.3 Hz)

ESI-MS (m/e): 360.4 [M+H]+

Example 42

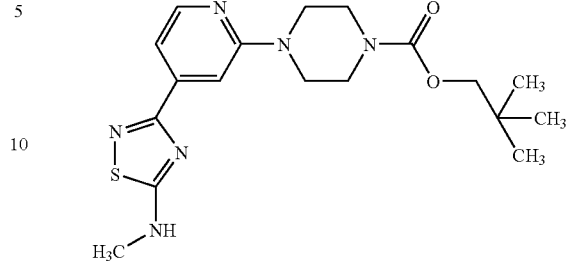

2,2-Dimethylpropyl 4-{4-[5-(methylamino)-1,2,4-thiadiazol-3-yl]pyridin-2-yl}-1-piperazinecarboxylate 2,2-Dimethylpropyl 4-{4-[amino(hydroxyimino)methyl]pyridin-2-yl}piperazine-1-carboxylate (122 mg) obtained in Example 26-1) was dissolved in dimethylformamide (1 mL), and methyl isothiocyanate (41 mg) was added thereto and stirred at 100° C. for 1 hour. The reaction liquid was diluted with ethyl acetate, washed with water and saturated saline water, and dried with anhydrous sodium sulfate. The solvent was evaporated away, and the resulting residue was isolated and purified through thin-layer silica gel chromatography (hexane/ethyl acetate=1/1) to obtain 31.3 mg of the entitled compound as a colorless solid.

$^1$HNMR (300 MHz, CDCl$_3$, δ ppm): 0.96 (9H, s), 3.08 (3H, d, J=4.2 Hz), 3.64 (8H, s), 3.83 (2H, s), 5.94 (1H, br s), 7.37 (1H, d, J=5.1 Hz), 7.42 (1H, s), 8.27 (1H, d, J=5.1 Hz)

ESI-MS (m/e): 391.3 [M+H]+

Example 43

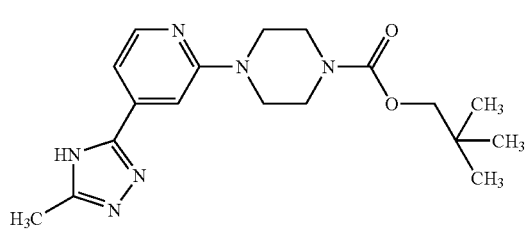

2,2-Dimethylpropyl 4-[4-(5-methyl-1,2,4-triazol-3-yl)pyridin-2-yl]-1-piperazinecarboxylate 2,2-Dimethylpropyl 4-(4-cyanopyridin-2-yl)piperazine-1-carboxylate (143 mg) obtained in Example 2 was dissolved in ethanol (5 mL), and hydrazine acetate (140 mg) and potassium carbonate (328 mg) were added thereto and heated under reflux for 5 hours, then the reaction liquid was evaporated. Acetic anhydride (3 mL) was added to the resulting residue, and heated under reflux for 2 hours, then the reaction liquid was diluted with ethyl acetate, washed with water and saturated saline water, and dried with anhydrous sodium sulfate. The solvent was evaporated away, and the resulting residue was isolated and purified through thin-layer silica gel chromatography (chloroform/methanol=9/1) to obtain 7.6 mg of the entitled compound as a colorless oil.

$^1$HNMR (300 MHz, CDCl$_3$, δ ppm): 0.97 (9H, s), 2.56 (3H, s), 3.64 (8H, s), 3.83 (2H, s), 7.30 (1H, d, J=5.3 Hz), 7.36 (1H, s), 8.27 (1H, d, J=5.3 Hz)
ESI-MS (m/e): 359.2 [M+H]+

Example 44

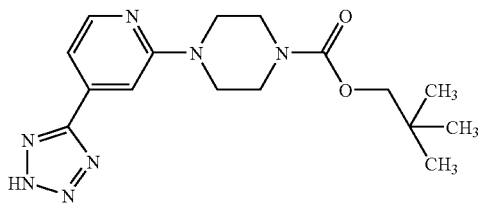

2,2-Dimethylpropyl 4-[4-(tetrazol-5-yl)pyridin-2-yl]-1-piperazinecarboxylate 2,2-Dimethylpropyl 4-(4-cyanopyridin-2-yl)piperazine-1-carboxylate (120 mg) obtained in Example 2 was dissolved in toluene (5 mL), and trimethylsilylazide (0.105 mL) and a catalytic amount of dibutyltin (IV) oxide were added thereto and heated under reflux for 8 hours. The solvent was evaporated away, and the resulting residue was isolated and purified through thin-layer silica gel chromatography (chloroform/methanol=9/1) to obtain 16.5 mg of the entitled compound as a colorless solid.
$^1$HNMR (300 MHz, CD$_3$OD, δ ppm): 0.98 (9H, s), 3.69 (8H, s), 3.82 (2H, s), 7.34 (1H, d, J=5.3 Hz), 7.56 (1H, s), 8.22 (1H, d, J=5.3 Hz)
ESI-MS (m/e): 346.2 [M+H]+

Example 45

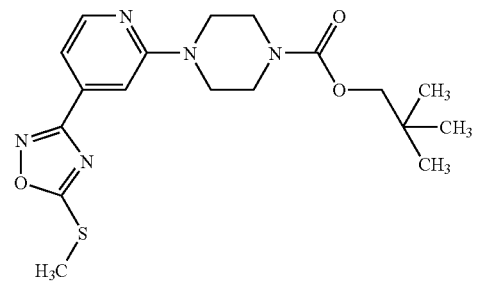

2,2-Dimethylpropyl 4-{4-[5-(methylthio)-1,2,4-oxadiazol-3-yl]pyridin-2-yl}-1-piperazinecarboxylate 2,2-Dimethylpropyl 4-{4-[amino(hydroxyimino)methyl]pyridin-2-yl}piperazine-1-carboxylate (340 mg) obtained in Example 26-1) was dissolved in acetonitrile (2 mL), and 1,1'-thiocarbonyldiimidazole (231 mg) was added thereto and stirred at room temperature for 2 hours. The reaction liquid was diluted with ethyl acetate, washed with water and saturated saline water, and dried with anhydrous sodium sulfate. The solvent was evaporated away, and the resulting residue was dissolved in dimethylformamide (2 mL), and methyl iodide (0.080 mL) and potassium carbonate (198 mg) were added thereto and stirred at room temperature for 1 hour. The reaction liquid was diluted with ethyl acetate, washed with water and saturated saline water, and dried with anhydrous sodium sulfate. The solvent was evaporated away, and the resulting residue was isolated and purified through thin-layer silica gel chromatography (hexane/ethyl acetate=7/3) to obtain 25.2 mg of the entitled compound as a colorless oil.
$^1$HNMR (300 MHz, CDCl$_3$, δ ppm): 0.97 (9H, s), 2.80 (3H, s), 3.64 (8H, s), 3.83 (2H, s), 7.25 (1H, d, J=5.2 Hz), 7.28 (1H, s), 8.31 (1H, d, J=5.2 Hz)
ESI-MS (m/e): 392.1 [M+H]+

Example 46

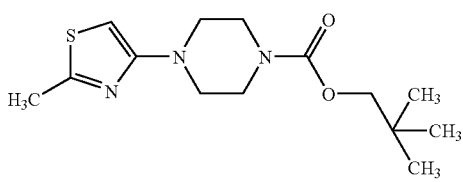

2,2-Dimethylpropyl 4-(2-methylthiazol-4-yl)-1-piperazinecarboxylate

1) Production of tert-butyl 4-(bromoacetyl)piperazinecarboxylate

With cooling with ice, bromoacetyl bromide (680 μL) was added to a chloroform (10 ml) solution of 1-tert-butyloxycarbonylpiperazine (1 g) and triethylamine (2.2 mL). At that temperature, this was stirred for 0.5 hours, and then at room temperature for further 0.5 hours. The reaction liquid was diluted with ethyl acetate, washed with water and saturated saline water, and dried with anhydrous sodium sulfate. The solvent was evaporated away under reduced pressure, and the resulting residue was purified through silica gel column chromatography (hexane/ethyl acetate=7/3) to obtain 340 mg of the entitled compound.
$^1$HNMR (300 MHz, CDCl$_3$) δ: 1.46 (9H, s), 3.41-3.64 (8H, m), 3.86 (2H, s)

2) Production of tert-butyl 4-(2-methylthiazol-4-yl)-1-piperazinecarboxylate

Thioacetamide (120 mg) was added to an ethanol (6 mL) solution of tert-butyl 4-(bromoacetyl)piperazinecarboxylate (340 mg) obtained in the above 1), and heated under reflux for 3 hours. The reaction liquid was restored to room temperature, then the solvent was evaporated away under reduced pressure, and the resulting residue was purified through silica gel column chromatography (hexane/ethyl acetate=7/3) to obtain 7 mg of the entitled compound.
$^1$HNMR (300 MHz, CDCl$_3$) δ: 1.48 (9H, s), 2.62 (3H, s), 3.20 (4H, t, J=5.4 Hz), 3.56 (4H, t, J=5.4 Hz), 5.74 (1H, s)
ESI-MS Found: m/z 284.2 [M+H]+

3) Production of 2,2-dimethylpropyl 4-(2-methylthiazol-4-yl)-1-piperazinecarboxylate 1-(1-Tert-butyloxycarbonyl)-4-(2-methyl-4-thiazolyl)piperazine (7 mg) obtained in the above 3) was dissolved in formic acid (1 mL), and stirred overnight at room temperature. The reaction liquid was concentrated under reduced pressure, and the resulting residue was dissolved in pyridine (1 mL), and neopentyl chloroformate (15 μL) was added thereto at room temperature. This was stirred for 0.5 hours, then the reaction liquid was diluted with ethyl acetate, washed with water and saturated saline water, and dried with anhydrous sodium sulfate. The solvent was evaporated away under reduced pressure, and the resulting residue was purified through partitioning thin-layer silica gel chromatography (ethyl acetate/hexane=1/1) to obtain 4 mg of the entitled compound as a colorless solid.

$^1$HNMR (300 MHz, CDCl$_3$, δ ppm): 0.96 (9H, s), 2.63 (3H, s), 3.23 (4H, t, J=5.1 Hz), 3.64 (4H, t, J=5.1 Hz), 3.81 (2H, s), 5.76 (1H, s)

ESI-MS (m/e): 298.3 [M+H]+

Example 47

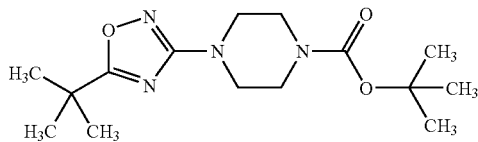

Tert-butyl 4-(5-tert-butyl-1,2,4-oxadiazol-3-yl)-1-piperazinecarboxylate

Tert-butyl 4-[(hydroxyamino)iminomethyl]piperazine-1-carboxylate (1.34 g) was dissolved in toluene (10 mL), and pivalic anhydride (5 mL) was added thereto and heated under reflux for 1 hour. Then, the reaction liquid was diluted with ethyl acetate, washed with saturated sodium hydrogencarbonate and saturated saline water, and dried with anhydrous sodium sulfate. The solvent was evaporated away, and the resulting residue was isolated and purified through thin-layer silica gel chromatography (ethyl acetate/hexane=7/3) to obtain 214 mg of the entitled compound as a colorless solid.

$^1$HNMR (300 MHz, CDCl$_3$, δ ppm): 1.38 (9H, s), 1.48 (9H, s), 3.39-3.42 (4H, m), 3.50-3.53 (4H, m)

ESI-MS (m/e): 255.2 [M-Bu]+

Example 48

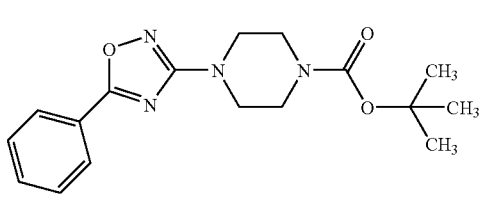

Tert-butyl 4-(5-phenyl-1,2,4-oxadiazol-3-yl)-1-piperazinecarboxylate

The entitled compound was obtained as a colorless solid according to the same method as in Example 47 but using benzoic anhydride in place of pivalic anhydride.

$^1$HNMR (300 MHz, CDCl$_3$, δ ppm): 1.49 (9H, s), 3.53-3.55 (8H, m), 7.47-7.57 (3H, m), 8.07 (2H, d, J=7.1 Hz)

ESI-MS (m/e): 231.2 [M-Boc]+

Example 49

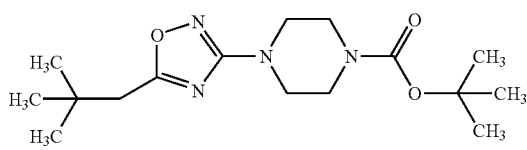

Tert-butyl 4-[5-(2,2-dimethylpropyl)-1,2,4-oxadiazol-3-yl]-1-piperazinecarboxylate Tert-butyl 4-[(4-hydroxyamino)iminomethyl]piperazine-1-carboxylate (192 mg) was dissolved in pyridine (3 mL), and tert-butylacetyl chloride (0.5 mL) was added thereto, heated under reflux for 2 hours, then the reaction liquid was diluted with diethyl ether, washed with water, 1 N hydrochloric acid, saturated sodium hydrogencarbonate and saturated saline water, and dried with anhydrous magnesium sulfate. The solvent was evaporated away, and the resulting residue was isolated and purified through thin-layer silica gel chromatography (ethyl acetate/hexane=7/3) to obtain 43.8 mg of the entitled compound as a colorless solid.

$^1$HNMR (300 MHz, CDCl$_3$, δ ppm): 1.04 (9H, s), 1.48 (9H, s), 2.65 (2H, s), 3.41-3.43 (4H, m), 3.50-3.54 (4H, m)

ESI-MS (m/e): 325.2 [M+H]+

Example 50

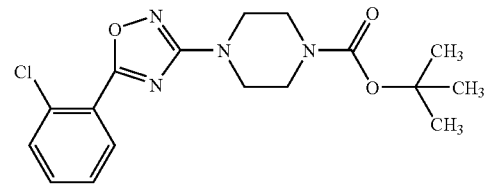

Tert-butyl 4-[5-(2-chlorophenyl)-1,2,4-oxadiazol-3-yl]-1-piperazinecarboxylate

The entitled compound was obtained as a colorless solid according to the same method as in Example 49 but using o-chlorobenzoyl chloride in place of tert-butylacetyl chloride.

$^1$HNMR (300 MHz, CDCl$_3$, δ ppm): 1.49 (9H, s), 3.53-3.55 (8H, m), 7.36-7.56 (3H, m), 8.00 (1H, dd, J=1.4 and 7.8 Hz)

ESI-MS (m/e): 265.1 [M-Boc]+

Example 51

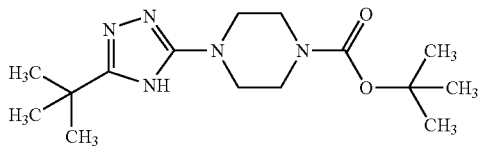

Tert-butyl 4-(5-tert-butyl-1,2,4-triazol-3-yl)-1-piperazinecarboxylate

Tert-butyl 4-cyanopiperazine-1-carboxylate (694 mg) was dissolved in ethanol (20 mL), and hydrazine hydrochloride (0.95 g) and potassium carbonate (1.85 g) were added thereto and heated under reflux for 2 hours, then the reaction liquid was filtered. The filtrate was evaporated, the resulting residue was dissolved in pyridine (5 mL), the pivalic anhydride (1 mL) was added thereto and stirred at 120° C. for 2 hours. Them, the reaction liquid was diluted with ethyl acetate, washed with water, 1 N hydrochloric acid, saturated sodium hydrogencarbonate, and saturated saline water, and then dried with anhydrous sodium sulfate. The solvent was evaporated away, and the resulting residue was isolated and purified through silica gel column chromatography (ethyl acetate/hexane=1/1) to obtain 246 mg of the entitled compound as a colorless solid.

$^1$HNMR (300 MHz, CDCl$_3$, δ ppm): 1.35 (9H, s), 1.48 (9H, s), 3.35-3.38 (4H, m), 3.51-3.55 (4H, m)

APCI-MS (m/e): 310.3 [M+H]+

Example 52

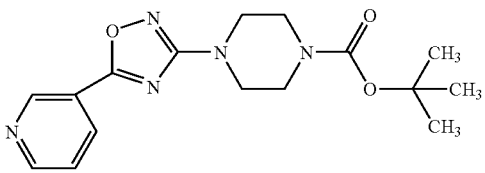

Tert-butyl 4-[5-(pyridin-3-yl)-1,2,4-oxadiazol-3-yl]-1-piperazinecarboxylate

The entitled compound was obtained as a colorless solid according to the same method as in Example 49 but using nicotinoyl chloride hydrochloride in place of tert-butylacetyl chloride.

$^1$HNMR (300 MHz, CDCl$_3$, δ ppm): 1.49 (9H, s), 3.53-3.58 (8H, m), 7.43-7.48 (1H, m), 8.31-8.35 (1H, m), 8.79-8.81 (1H, m), 9.30 (1H, d, J=1.4 Hz)

ESI-MS (m/e): 332.3 [M+H]+

Example 53

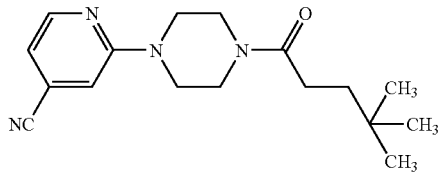

1-(4,4-Dimethylpentanoyl)-4-(4-cyanopyridin-2-yl)piperazine

2-Chloro-4-cyanopyridine (735 mg) and piperazine (1.8 sg) were dissolved in dimethyl sulfoxide (10 mL), and stirred at 120° C. for 2 hours, then the reaction liquid was diluted with ethyl acetate, washed with water and then with saturated saline water, and dried with anhydrous sodium sulfate. The solvent was evaporated away, the resulting residue was dissolved in pyridine (7 mL), and 4,4-dimethylvaleric acid (527 mg) and 1-ethyl-3-(3-dimethylaminopropyl)carbodiimide hydrochloride (1.05 g) were added thereto, stirred at room temperature for 3 hours, then the reaction liquid was diluted with ethyl acetate, washed with water, 1 N hydrochloric acid, aqueous saturated sodium hydrogencarbonate solution and saturated saline water, and dried with anhydrous sodium sulfate. The solvent was evaporated away, and the resulting residue was isolated and purified through silica gel column chromatography (ethyl acetate/hexane=7/3) to obtain 786 mg of the entitled compound as a colorless solid.

$^1$HNMR (300 MHz, CDCl$_3$, δ ppm): 0.94 (9H, s), 1.54-1.62 (2H, m), 2.32-2.37 (2H, m), 3.55-3.76 (8H, m), 6.51-6.82 (2H, m), 8.30 (1H, d, J=5.5 Hz)

ESI-MS (m/e): 301.3 [M+H]+

Example 54

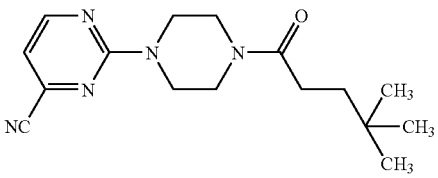

1-(4,4-Dimethylpentanoyl)-4-(4-cyanopyrimidin-2-yl)piperazine

The entitled compound was obtained as a yellow solid according to the same method as in Example 53 but using 2-chloro-4-cyanopyrimidine in place of 2-chloro-4-cyanopyridine.

$^1$HNMR (300 MHz, CDCl$_3$, δ ppm): 0.94 (9H, s), 1.54-1.60 (2H, m), 2.32-2.38 (2H, m), 3.54-3.89 (8H, m), 6.81 (1H, d, J=4.7 Hz), 8.48 (1H, d, J=4.7 Hz)

ESI-MS (m/e): 302.2 [M+H]+

Example 55

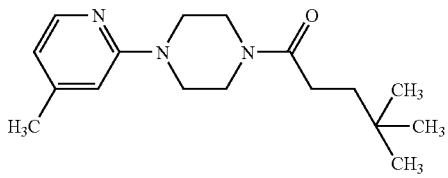

1-(4,4-Dimethylpentanoyl)-4-(4-methylpyridin-2-yl)piperazine

The entitled compound was obtained as a colorless solid according to the same method as in Example 53 but using 2-fluoro-4-methylpyridine in place of 2-chloro-4-cyanopyridine.

$^1$HNMR (300 MHz, CDCl$_3$, δ ppm): 0.93 (9H, s), 1.53-1.59 (2H, m), 2.28 (3H, s), 2.31-2.37 (2H, m), 3.46-3.50 (2H, m), 3.60-3.62 (4H, m), 3.73-3.76 (2H, m), 6.48 (1H, s), 6.52 (1H, d, J=5.2 Hz), 8.06 (1H, d, J=5.2 Hz)

ESI-MS (m/e): 290.2 [M+H]+

Example 56

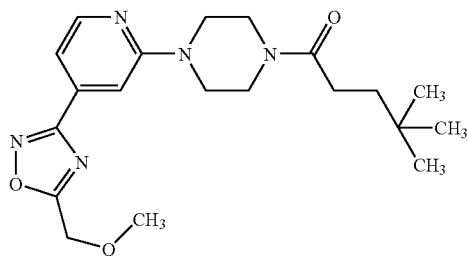

1-(4,4-Dimethylpentanoyl)-4-{4-[5-(methoxymethyl)-1,2,4-oxadiazol-3-yl]pyridin-2-yl}piperazine 1) Production of 1-{4-[amino(hydroxyimino)methyl]pyridin-2-yl}-4-(4,4-dimethylpentanoyl)piperazine 1-(4,4-Dimethylpentanoyl)-4-(4-cyanopyridin-2-yl)piperazine (2.91 g) obtained in Example 53 was dissolved in ethanol (20 mL), and hydroxyamine hydrochloride (2.16 g) and potassium carbonate (5.38 g) were added thereto and heated under reflux for 2 hours. Then, the solvent was evaporated away, and the resulting residue was diluted with ethyl acetate, washed with water and saturated saline water, and dried with anhydrous sodium sulfate. The solvent was evaporated away to obtain 2.04 g of the entitled compound.

2) Production of 1-(4,4-dimethylpentanoyl)-4-{4-[5-(methoxymethyl)-1,2,4-oxadiazol-3-yl]pyridin-2-yl}piperazine 1-{4-[Amino(hydroxyimino)methyl]pyridin-2-yl}-4-(4,4-dimethylpentanoyl)piperazine (62 mg) was dissolved in tetrahydrofuran (2 mL), then oily sodium hydride (13 mg) was added thereto, stirred at 60° C. for 20 minutes, and methyl methoxyacetate (0.028 mL) was added thereto and heated under reflux for 1 hour. The reaction liquid was diluted with ethyl acetate, washed with water and saturated saline water, and dried with anhydrous sodium sulfate. The solvent was evaporated away, and the resulting residue was isolated and purified through thin-layer silica gel chromatography (hexane/ethyl acetate=1/1) to obtain 44.3 mg of the entitled compound as a colorless solid.

$^1$HNMR (300 MHz, CDCl$_3$, δ ppm): 0.94 (9H, s), 1.54-1.63 (2H, m), 2.33-2.38 (2H, m), 3.57 (3H, s), 3.60-3.79 (8H, m), 4.77 (2H, s), 7.30-7.34 (2H, m), 8.32 (1H, d, J=5.2 Hz)

ESI-MS (m/e): 388.2 [M+H]+

Example 57

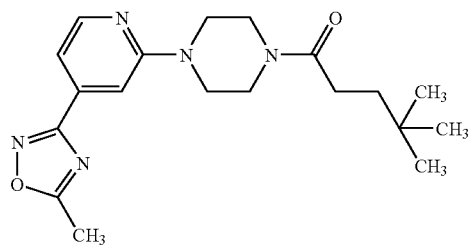

1-(4,4-Dimethylpentanoyl)-4-[4-(5-methyl-1,2,4-oxadiazol-3-yl)pyridin-2-yl]piperazine Acetic anhydride (2 mL) was added to 1-{4-[amino(hydroxyimino)methyl]pyridin-2-yl}-4-(4,4-dimethylpentanoyl)piperazine (104 mg) obtained in Example 56-1), heated under reflux for 2 hours, then the excess acetic anhydride was evaporated away, the residue was diluted with ethyl acetate, washed with aqueous saturated sodium hydrogencarbonate solution and saturated saline water, and dried with anhydrous sodium sulfate. The solvent was evaporated away, and the resulting residue was isolated and purified through thin-layer silica gel chromatography (hexane/ethyl acetate=1/1) to obtain 14.5 mg of the entitled compound as a yellow solid.

$^1$HNMR (300 MHz, CDCl$_3$, δ ppm): 0.94 (9H, s), 1.54-1.60 (2H, m), 2.32-2.38 (2H, m), 2.68 (3H, s), 3.61-3.63 (4H, m), 3.71-3.77 (4H, m), 7.28-7.30 (2H, m), 8.31-8.33 (1H, m)

ESI-MS (m/e): 358.2 [M+H]+

Example 58

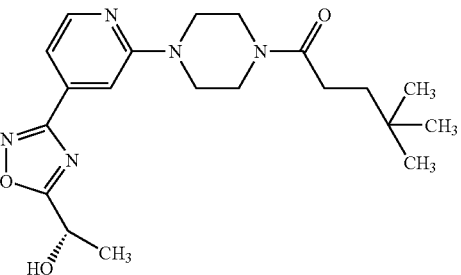

1-(4,4-Dimethylpentanoyl)-4-(4-{5-[(1S)-hydroxy-
ethyl]-1,2,4-oxadiazol-3-yl}pyridin-2-yl)piperazine The entitled compound was obtained as a yellow solid according to the same method as in Example 56 but using methyl (S)-lactate in place of methyl methoxyacetate.
¹HNMR (300 MHz, CDCl₃, δ ppm): 0.94 (9H, s), 1.54-1.66 (2H, m), 1.73 (3H, d, J=6.7 Hz), 2.32-2.38 (2H, m), 3.16 (1H, br s), 3.58-3.78 (8H, m), 5.12-5.22 (1H, m), 7.28-7.31 (2H, m), 8.32 (1H, d, J=5.1 Hz)
ESI-MS (m/e): 388.3 [M+H]+

Example 59

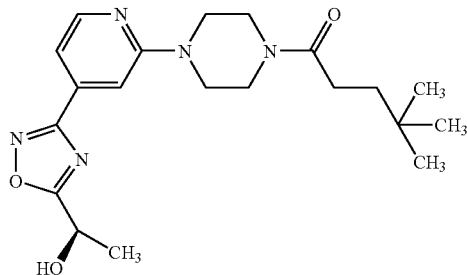

1-(4,4-Dimethylpentanoyl)-4-(4-{5-[(1R)-hydroxy-
ethyl]-1,2,4-oxadiazol-3-yl}pyridin-2-yl)piperazine The entitled compound was obtained as a yellow solid according to the same method as in Example 56 but using methyl (R)-lactate in place of methyl methoxyacetate.
¹HNMR (300 MHz, CDCl₃, δ ppm): 0.94 (9H, s), 1.54-1.60 (2H, m), 1.73 (3H, d, J=6.9 Hz), 2.32-2.38 (2H, m), 2.91 (1H, br s), 3.61-3.78 (8H, m), 5.14-5.22 (1H, m), 7.27-7.32 (2H, m), 8.32 (1H, d, J=5.2 Hz)
APCI-MS (m/e): 388.1 [M+H]+

Example 60

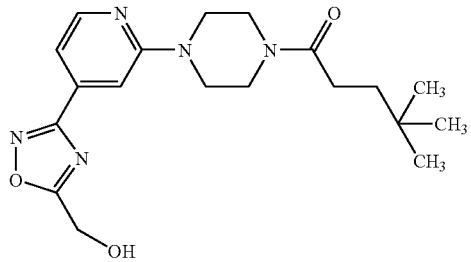

1-(4,4-Dimethylpentanoyl)-4-{4-[5-(hydroxym-
ethyl)-1,2,4-oxadiazol-3-yl]pyridin-2-yl}piperazine The entitled compound was obtained as a colorless solid according to the same method as in Example 56 but using methyl hydroxyacetate in place of methyl methoxyacetate.
¹HNMR (300 MHz, CDCl₃, δ ppm): 0.94 (9H, s), 1.54-1.59 (2H, m), 2.32-2.38 (2H, m), 3.60-3.76 (8H, m), 4.98 (2H, d, J=6.0 Hz), 7.28-7.32 (2H, m), 8.33 (1H, d, J=4.9 Hz)
APCI-MS (m/e): 374.2 [M+H]+

Example 61

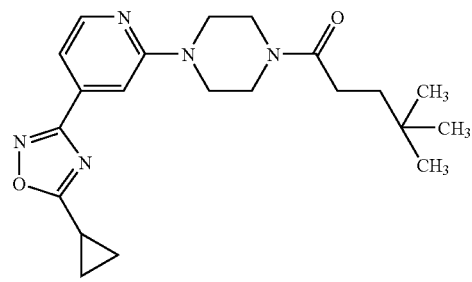

1-(4,4-Dimethylpentanoyl)-4-[4-(5-cyclopropyl-1,2,
4-oxadiazol-3-yl)pyridin-2-yl]piperazine 1-{4-[Amino(hydroxyimino)methyl]pyridin-2-yl}-4-(4,
4-dimethylpentanoyl)piperazine (235 mg) obtained in Example 56-1) was dissolved in pyridine (1 mL), then cyclopropanecarbonyl chloride (0.065 mL) was added thereto and heated under reflux for 90 minutes. The reaction liquid was diluted with ethyl acetate, washed with water, aqueous saturated sodium hydrogencarbonate solution and saturated saline water, and dried with anhydrous sodium sulfate. The solvent was evaporated away, and the resulting residue was isolated and purified through thin-layer silica gel chromatography (hexane/ethyl acetate=1/1) to obtain 187 mg of the entitled compound as a colorless solid.
¹HNMR (300 MHz, CDCl₃, δ ppm): 0.94 (9H, s), 1.24-1.34 (4H, m), 1.54-1.60 (2H, m), 2.23-2.38 (3H, m), 3.61-3.79 (8H, m), 7.24-7.27 (2H, m), 8.30 (1H, d, J=5.2 Hz)
ESI-MS (m/e): 384.2 [M+H]+

Example 62

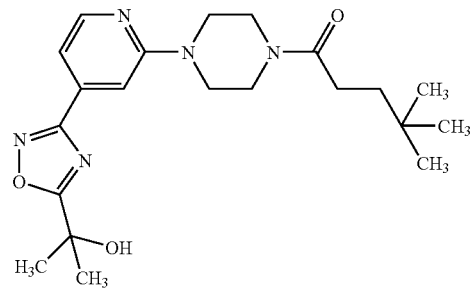

1-(4,4-Dimethylpentanoyl)-4-{4-[5-(1-hydroxy-1-
methylethyl)-1,2,4-oxadiazol-3-yl]pyridin-2-
yl}piperazine The entitled compound was obtained as a colorless solid according to the same method as in Example 56 but using ethyl 2-hydroxyisobutyrate in place of methyl methoxyacetate.
¹HNMR (300 MHz, CDCl₃, δ ppm): 0.94 (9H, s), 1.54-1.59 (2H, m), 1.76 (6H, s), 2.32-2.38 (2H, m), 3.62-3.79 (8H, m), 7.28-7.32 (2H, m), 8.32 (1H, d, J=5.3 Hz)
ESI-MS (m/e): 402.2 [M+H]+

Example 63

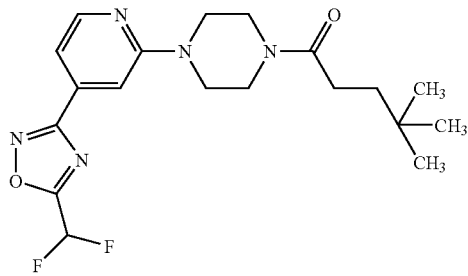

1-(4,4-Dimethylpentanoyl)-4-{4-[5-(difluoromethyl)-1,2,4-oxadiazol-3-yl]pyridin-2-yl}piperazine The entitled compound was obtained as a colorless oil according to the same method as in Example 56 but using methyl difluoroacetate in place of methyl methoxyacetate.

$^1$HNMR (300 MHz, CDCl$_3$, δ ppm): 0.94 (9H, s), 1.55-1.60 (2H, m), 2.33-2.38 (2H, m), 3.61-3.80 (8H, m), 6.88 (1H, t, J=52.2 Hz), 7.29-7.33 (2H, m), 8.36 (1H, d, J=5.1 Hz)
ESI-MS (m/e): 394.2 [M+H]+

Example 64

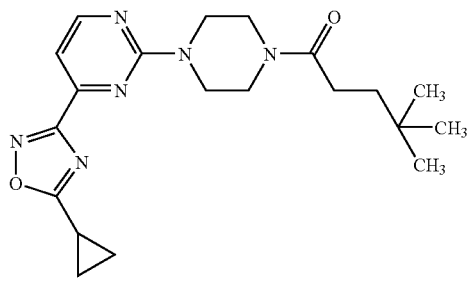

1-(4,4-Dimethylpentanoyl)-4-[4-(5-cyclopropyl-1,2,4-oxadiazol-3-yl)pyrimidin-2-yl]piperazine 1) Production of 1-{4-[amino(hydroxyimino)methyl]pyrimidin-2-yl}-4-(4,4-dimethylpentanoyl)piperazine 1-(4,4-Dimethylpentanoyl)-4-(4-cyanopyrimidin-2-yl)piperazine (540 mg) obtained in Example 54 was dissolved in ethanol (5 mL), and hydroxyamine hydrochloride (386 mg) and potassium carbonate (995 mg) were added thereto and heated under reflux for 2 hours. Then, the solvent was evaporated away, and the resulting residue was diluted with ethyl acetate, washed with water and saturated saline water, and dried with anhydrous sodium sulfate. The solvent was evaporated away to obtain 476 mg of the entitled compound.

2) Production of 1-(4,4-dimethylpentanoyl)-4-[4-(5-cyclopropyl-1,2,4-oxadiazol-3-yl)pyrimidin-2-yl]piperazine 1-{4-[Amino(hydroxyimino)methyl]pyrimidin-2-yl}-4-(4,4-dimethylpentanoyl)piperazine (59.5 mg) was dissolved in pyridine (1 mL), and cyclopropanecarbonyl chloride (0.020 mL) was added thereto and heated under reflux for 3 hours. The reaction liquid was diluted with ethyl acetate, washed with aqueous saturated ammonium chloride solution, aqueous saturated sodium hydrogencarbonate solution and saturated saline water, and dried with anhydrous sodium sulfate. The solvent was evaporated away, and the resulting residue was isolated and purified through thin-layer silica gel chromatography (hexane/ethyl acetate=3/2) to obtain 31.9 mg of the entitled compound as a colorless solid.

$^1$HNMR (300 MHz, CDCl$_3$, δ ppm): 0.94 (9H, s), 1.26-1.35 (4H, m), 1.54-1.60 (2H, m), 2.27-2.38 (3H, m), 3.55-3.58 (2H, m), 3.71-3.73 (2H, m), 3.89-3.96 (4H, m), 7.21 (1H, d, J=4.7 Hz), 8.49 (1H, d, J=4.7 Hz)
ESI-MS (m/e): 385.2 [M+H]+

Example 65

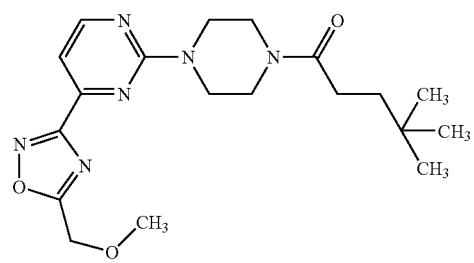

1-(4,4-Dimethylpentanoyl)-4-{4-[5-(methoxymethyl)-1,2,4-oxadiazol-3-yl]pyrimidin-2-yl}piperazine The entitled compound was obtained as a colorless oil according to the same method as in Example 64 but using methoxyacetyl chloride in place of cyclopropanecarbonyl chloride.

$^1$HNMR (300 MHz, CDCl$_3$, δ ppm): 0.94 (9H, s), 1.54-1.60 (2H, m), 2.33-2.38 (2H, m), 3.56 (3H, s), 3.56-3.59 (2H, m), 3.71-3.75 (2H, m), 3.90-3.97 (4H, m), 4.79 (2H, s), 7.29 (1H, d, J=4.9 Hz), 8.53 (1H, d, J=4.9 Hz)
ESI-MS (m/e): 389.3 [M+H]+

Example 66

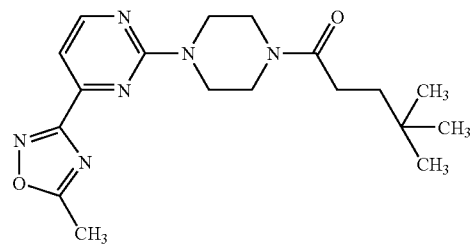

1-(4,4-Dimethylpentanoyl)-4-[4-(5-methyl-1,2,4-oxadiazol-3-yl)pyrimidin-2-yl]piperazine 1-{4-[Amino(hydroxyimino)methyl]pyrimidin-2-yl}-4-(4,4-dimethylpentanoyl)piperazine (186 mg) obtained in Example 64-1) was dissolved in tetrahydrofuran (3 mL), and oily sodium hydroxide (25 mg) was added thereto and stirred at 60° C. for 20 minutes. Then, ethyl acetate (0.082 ml) was added to it and heated under reflux for 1 hour. The reaction liquid was diluted with ethyl acetate, washed with water and saturated saline water, and dried with anhydrous sodium sulfate. The solvent was evaporated away, and the resulting residue was isolated and purified through thin-layer silica gel chromatography (chloroform/methanol=19/1) to obtain 53.4 mg of the entitled compound as a colorless solid.

$^1$HNMR (300 MHz, CDCl$_3$, δ ppm): 0.94 (9H, s), 1.54-1.60 (2H, m), 2.32-2.38 (2H, m), 2.70 (3H, s), 3.55-3.59 (2H, m), 3.71-3.74 (2H, m), 3.90-3.99 (4H, m), 7.25 (1H, d, J=4.9 Hz), 8.51 (1H, d, J=4.9 Hz)

ESI-MS (m/e): 359.2 [M+H]+

Example 67

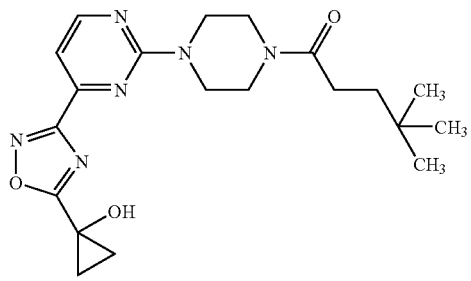

1-(4,4-Dimethylpentanoyl)-4-{4-[5-(1-hydroxycyclopropyl)-1,2,4-oxadiazol-3-yl]pyrimidin-2-yl}piperazine The entitled compound was obtained as a colorless oil according to the same method as in Example 66 but using methyl 1-hydroxycyclopropanecarboxylate in place of ethyl acetate.

$^1$HNMR (300 MHz, CDCl$_3$, δ ppm): 0.93 (9H, s), 1.54-2.60 (6H, m), 2.33-2.38 (2H, m), 3.56-3.96 (8H, m), 7.24 (1H, d, J=4.9 Hz), 8.51 (1H, d, J=4.9 Hz)

ESI-MS (m/e): 401.2 [M+H]+

Example 68

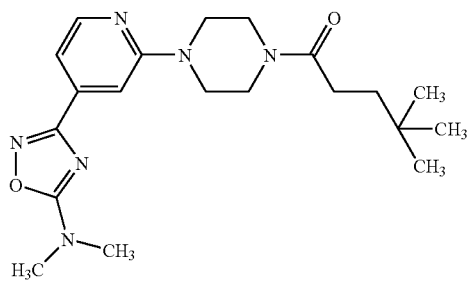

1-(4,4-Dimethylpentanoyl)-4-{4-[5-(dimethylamino)-1,2,4-oxadiazol-3-yl]pyridin-2-yl}piperazine 1) Production of 1-(4,4-dimethylpentanoyl)-4-{4-[5-(trichloromethyl)-1,2,4-oxadiazol-3-yl]pyridin-2-yl}piperazine The entitled compound was obtained according to the same method as in Example 57 but using trichloroacetic anhydride in place of acetic anhydride.

ESI-MS Found: m/z 460.1 [M+H]+

2) Production of 1-(4,4-dimethylpentanoyl)-4-{4-[5-(dimethylamino)-1,2,4-oxadiazol-3-yl]pyridin-2-yl}piperazine 1-(4,4-Dimethylpentanoyl)-4-{4-[5-(trichloromethyl)-1,2,4-oxadiazol-3-yl]pyridin-2-yl}piperazine (48.1 mg) was dissolved in methanol (2 mL), and 2.0 M dimethylamine/methanol solution (1 mL) was added thereto and stirred at room temperature for 2 hours. Then, the solvent was evaporated away and the resulting residue was isolated and purified through thin-layer silica gel chromatography (hexane/ethyl acetate=1/1) to obtain 17.5 mg of the entitled compound as a yellow oil.

$^1$HNMR (300 MHz, CDCl$_3$, δ ppm): 0.94 (9H, s), 1.54-1.60 (2H, m), 2.32-2.38 (2H, m), 3.22 (6H, s), 3.57-3.78 (8H, m), 7.22 (1H, d, J=5.0 Hz), 7.24 (1H, s), 8.27 (1H, d, J=5.0 Hz)

ESI-MS (m/e): 387.2 [M+H]+

Example 69

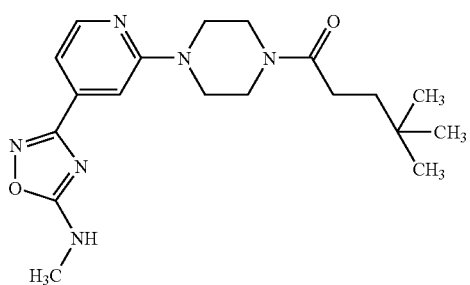

1-(4,4-Dimethylpentanoyl)-4-{4-[5-(methylamino-1,2,4-oxadiazol-3-yl]pyridin-2-yl}piperazine The entitled compound was obtained as a yellow solid according to the same method as in Example 68 but using 40% methylamine/methanol solution in place of 2.0 M dimethylamine/methanol solution.

$^1$HNMR (300 MHz, CDCl$_3$, δ ppm): 0.94 (9H, s), 1.54-1.60 (2H, m), 2.32-2.38 (2H, m), 3.15 (3H, d, J=5.0 Hz), 3.58-3.78 (8H, m), 5.39 (1H, br), 7.21 (1H, d, J=5.1 Hz), 7.24 (1H, s), 8.28 (1H, d, J=5.1 Hz)

ESI-MS (m/e): 373.2 [M+H]+

Example 70

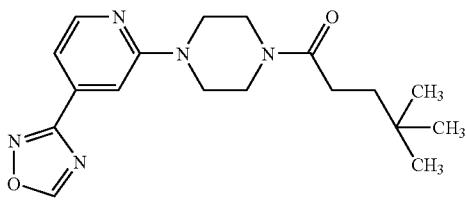

1-(4,4-Dimethylpentanoyl)-4-[4-(1,2,4-oxadiazol-3-yl)pyridin-2-yl]piperazine 1-(4,4-Dimethylpentanoyl)-4-{4-[5-(trichloromethyl)-1,2,4-oxadiazol-3-yl]pyridin-2-yl}piperazine (43 mg) obtained in Example 68-1) was dissolved in methanol (3 mL), and sodium borohydride (46 mg) was added thereto and stirred at room temperature for 1 hour. Then, the solvent was evaporated away, and the resulting residue was isolated and purified through thin-layer silica gel chromatography (hexane/ethyl acetate=1/1) to obtain 7.4 mg of the entitled compound as a colorless oil.

$^1$HNMR (300 MHz, CDCl$_3$, δ ppm): 0.94 (9H, s), 1.55-1.62 (2H, m), 2.33-2.38 (2H, m), 3.61-3.80 (8H, m), 7.32-7.35 (2H, m), 8.34 (1H, d, J=5.2 Hz), 8.81 (1H, s)

ESI-MS (m/e): 344.1 [M+H]+

Example 71

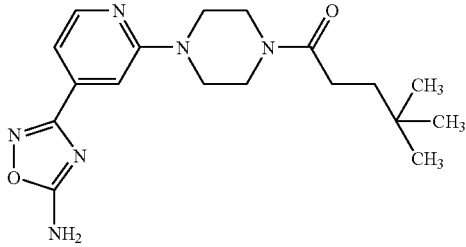

1-(4,4-Dimethylpentanoyl)-4-[4-(5-amino-1,2,4-oxadiazol-3-yl)pyridin-2-yl]piperazine The entitled compound was obtained as a yellow solid according to the same method as in Example 68 but using 2 M ammonia/methanol solution in place of 2.0 M dimethylamine/methanol solution.

$^1$HNMR (300 MHz, CDCl$_3$, δ ppm): 0.93 (9H, s), 1.54-1.57 (2H, m), 2.32-2.38 (2H, m), 3.57-3.79 (8H, m), 5.40 (2H, br s), 7.18 (1H, d, J=5.1 Hz), 7.21 (1H, s), 8.29 (1H, d, J=5.1 Hz)

ESI-MS (m/e): 359.2 [M+H]+

The usefulness of the compounds of formulae (I), (I-1), (I-2), (I-3), (I-4), (I-5) and (I-6) are verified, for example, in the following Test Examples.

The usefulness of the compounds of the invention as medicines was evaluated according to the methods described in the following Pharmaceutical Test Examples.

Using LIPOFECTAMINE (BY Gibco BRL), CHO cells were transfected with a cDNA of a human metabotropic glutamic acid receptor 1a (mGluR1a), thereby obtaining an mGluR1a stable expression strain. The mGluR1a-expressing CHO cells were incubated in a DMEM medium containing 10% dialyzed fetal calf serum, 1% proline, 100 units/ml penicillin, 0.1 mg/ml streptomycin sulfate, and 2 mM glutamine.

Pharmacological Test Example 1

Measurement of Intracellular Calcium Concentration

On the day before the test day, the mGluR1a-expressing CHO cells that had been plated in a 96-well black plate (View Plate by Packard) at 50000 cells/plate with 4 μM Fluo-3 were incubated in a CO$_2$ incubator for 1 hour. Next, the cells were washed four times with an HBSS solution containing 20 mM HEPES and 2.5 mM Probenecid, and then the intracellular calcium concentration was measured using Fluorescence Imaging Plate Reader (FLIPR by Molecular Device). The test compound and glutamic acid were conditioned with an HBSS solution containing 20 mM HEPES and 2.5 mM Probenecid. The test compound was added to the system before 5 minutes of agonist stimulation, and 10 μM glutamic acid was used as the agonist.

As a result of the above test, the compounds of Example 1, Example 3, Example 27, Example 39 and Example 58 showed no agonistic effect to mGluR1 to 10 μM. The compounds dose-dependently inhibited the calcium increase caused by 10 μM glutamic acid, and their IC$_{50}$ values are shown in Table 1 below.

TABLE 1

| Example No. | IC50 (nM) |
|---|---|
| Example 1 | 6.9 |
| Example 3 | 33 |
| Example 27 | 9.6 |
| Example 39 | 13 |
| Example 58 | 16 |

Pharmacological Test Example 2

Inhibitory Effect of Compound to Mouse Action Increased by Methamphetamine

Male ICR (CD-1) mice (20-40 g) were used. Using a motion watcher (by Neuroscience) for watching animal movement with an IR sensor, the motion of the mice was determined. A compound or a suitable solvent was administered to each mouse, and after 30 minutes, physiological saline water or methamphetamine was administered thereto. Immediately after that, the motion of the mice was watched for 60 minutes. Based on the difference between the motion of the methamphetamine-administered group and the solvent-administered group during the test term, 100%, the motion of the test compound-administered group is computed and expressed as inhibition %. 60 minutes after subcutaneous administration of methamphetamine (2 mg/kg) to the mice, their motion significantly increased. Intraabdominal administration of the mGluR1-inhibitory compound of the invention (30 mg/kg) before 30 minutes of the methamphetamine administration obviously inhibited the motion increase caused by methamphetamine. The results are shown in Table 2.

The results confirmed the potent antagonistic effect of compounds of the invention to methamphetamine.

TABLE 2

| Example No. | Motion (inhibition %) |
|---|---|
| Example 1 | >50 |
| Example 27 | >50 |

TABLE 2-continued

| Example No. | Motion (inhibition %) |
|---|---|
| Example 39 | >50 |
| Example 58 | >50 |

INDUSTRIAL APPLICABILITY

The compounds and their pharmaceutically acceptable salts of the invention have a potent mGluR1-inhibitory effect, and are useful for treatment and/or prevention for brain disorders such as convulsion, acute pain, inflammatory pain, chronic pain, cerebral infraction or transient cerebral ischemic attack, mental dysfunctions such as schizophrenia, as well as anxiety, drug addiction, Parkinson's disease and gastrointestinal disorders.

What is claimed is:

1. A compound of the formula (I):

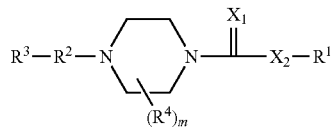

(I)

wherein:
$R^1$ represents a branched lower alkyl group having from 3 to 9 carbon atoms;
$R^2$ represents pyridyl;
$R^3$ is a 5-membered heteroaryl group having, in the ring, from 1 to 4 hetero atoms selected from a group consisting of a nitrogen atom, a sulfur atom and an oxygen atom, in which at least one hetero atom is a nitrogen atom, which is unsubstituted or substituted with a substituent selected from a substituent group α;
$R^4$ represents a hydrogen atom or a lower alkyl group, wherein the lower alkyl group may be substituted with a halogen atom;
$X_1$ is an oxygen atom;
$X_2$ represents an oxygen atom or a single bond;
m indicates an integer of from 0 to 4;
substituent group α is selected from:
a lower alkoxycarbonyl group, a lower alkylsulfanyl group, a lower alkyl group optionally substituted with a halogen atom, a lower alkoxy group or a hydroxy group, a hydroxy group, a cycloalkyl group, an amino group, an oxo group, a mono-lower alkylamino group and a di-lower alkylamino group;
or a pharmaceutically acceptable salt thereof.

2. The compound of claim 1 wherein $R^4$ is a hydrogen atom.

3. The compound of claim 1 wherein $R^3$ is an oxadiazolyl group, a thiadiazolyl group, a triazolyl group, a tetrazolyl group or a thiazolyl group, which is unsubstituted or substituted with a substituent selected from the substituent group α.

4. The compound of claim 1 wherein $R^3$ is an oxadiazolyl group or a triazolyl group group.

5. A compound which is selected from the group consisting of:
2,2-dimethylpropyl 4-(4-[5-[(1S)-1-hydroxyethyl]-1,2,4-oxadiazol-3-yl]pyridin-2-yl)-1-piperazinecarboxylate,
2,2-dimethylpropyl 4-(4-{5-[(1R)-1-hydroxyethyl]-1,2,4-oxadiazol-3-yl}pyridin-2-yl)-1-piperazinecarboxylate,
2,2-dimethylpropyl 4-[4-(5-methyl-1,2,4-oxadiazol-3-yl)pyridin-2-yl]-1-piperazinecarboxylate,
2,2-dimethylpropyl 4-[4-(5-methoxy-1,2,4-oxadiazol-3-yl)pyridin-2-yl]-1-piperazinecarboxylate,
2,2-dimethylpropyl 4-[4-(5-cyclopropyl-1,2,4-oxadiazol-3-yl)pyridin-2-yl]-1-piperazinecarboxylate,
2,2-dimethylpropyl 4-[4-[5-(methoxycarbonyl)-1,2,4-oxadiazol-3-yl]pyridin-2-yl]-1-piperazinecarboxylate,
2,2-dimethylpropyl 4-[4-[5-(trichloromethyl)-1,2,4-oxadiazol-3-yl]pyridin-2-yl]-1-piperazinecarboxylate,
2,2-dimethylpropyl 4-[4-[5-(trifluoromethyl)-1,2,4-oxadiazol-3-yl]pyridin-2-yl]-1-piperazinecarboxylate,
2,2-dimethylpropyl 4-[4-(5-methoxy-1,2,4-oxadiazol-3-yl)pyridin-2-yl]-1-piperazinecarboxylate,
2,2-dimethylpropyl 4-[4-(1,2,4-oxadiazol-3-yl)pyridin-2-yl]-1-piperazinecarboxylate,
2,2-dimethylpropyl 4-[4-(5-carbamoyl-1,2,4-oxadiazol-3-yl)pyridin-2-yl]-1-piperazinecarboxylate,
2,2-dimethylpropyl 4-{4-[5-(dimethylamino)-1,2,4-oxadiazol-3-yl]pyridin-2-yl}-1-piperazinecarboxylate,
2,2-dimethylpropyl 4-[4-(5-amino-1,2,4-oxadiazol-3-yl)pyridin-2-yl]-1-piperazinecarboxylate,
2,2-dimethylpropyl 4-{4-[5-(methylamino)-1,2,4-oxadiazol-3-yl]pyridin-2-yl}-1-piperazinecarboxylate,
2,2-dimethylpropyl 4-[4-(5-piperidinyl-1,2,4-oxadiazol-3-yl)pyridin-2-yl]-1-piperazinecarboxylate,
2,2-dimethylpropyl 4-[4-(3-methyl-1,2,4-oxadiazol-5-yl)pyridin-2-yl]-1-piperazinecarboxylate,
2,2-dimethylpropyl 4-{4-[5-(methylamino)-1,2,4-thiadiazol-3-yl]pyridin-2-yl}-1-piperazinecarboxylate,
2,2-dimethylpropyl 4-[4-(5-methyl-1,2,4-triazol-3-yl)pyridin-2-yl]-1-piperazinecarboxylate,
2,2-dimethylpropyl 4-[4-(tetrazol-5-yl)pyridin-2-yl]-1-piperazinecarboxylate,
2,2-dimethylpropyl 4-{4-[5-(methylthio)-1,2,4-oxadiazol-3-yl]pyridin-2-yl}-1-piperazinecarboxylate,
1-(4,4-dimethylpentanoyl)-4-{4-[5-(methoxymethyl)-1,2,4-oxadiazol-3-yl]pyridin-2-yl}piperazine,
1-(4,4-dimethylpentanoyl)-4-[4-(5-methyl-1,2,4-oxadiazol-3-yl)pyridin-2-yl]piperazine,
1-(4,4-dimethylpentanoyl)-4-(4-{5-[(1S)-hydroxyethyl]-1,2,4-oxadiazol-3-yl}pyridin-2-yl)piperazine,
1-(4,4-dimethylpentanoyl)-4-(4-{5-[(1R)-hydroxyethyl]-1,2,4-oxadiazol-3-yl}pyridin-2-yl)piperazine,
1-(4,4-dimethylpentanoyl)-4-{4-[5-(hydroxymethyl)-1,2,4-oxadiazol-3-yl]pyridin-2-yl}piperazine,
1-(4,4-dimethylpentanoyl)-4-[4-(5-cyclopropyl-1,2,4-oxadiazol-3-yl)pyridin-2-yl]piperazine,
1-(4,4-dimethylpentanoyl)-4-{4-[5-(1-hydroxy-1-methylethyl)-1,2,4-oxadiazol-3-yl]pyridin-2-yl}piperazine,
1-(4,4-dimethylpentanoyl)-4-{4-[5-(difluoromethyl)-1,2,4-oxadiazol-3-yl]pyridin-2-yl}piperazine,
1-(4,4-dimethylpentanoyl)-4-{4-[5-(dimethylamino)-1,2,4-oxadiazol-3-yl]pyridin-2-yl}piperazine,
1-(4,4-dimethylpentanoyl)-4-{4-[5-(methylamino)-1,2,4-oxadiazol-3-yl]pyridin-2-yl}piperazine,
1-(4,4-dimethylpentanoyl)-4-[4-(1,2,4-oxadiazol-3-yl)pyridin-2-yl]piperazine, or
1-(4,4-dimethylpentanoyl)-4-[4-(5-amino-1,2,4-oxadiazol-3-yl)pyridin-2-yl]piperazine; or a pharmaceutically acceptable salt thereof.

6. A pharmaceutical composition which comprises an inert carrier and a compound of claim 1, or a pharmaceutically acceptable salt thereof.

* * * * *